(12) United States Patent
Gee et al.

(10) Patent No.: US 7,129,346 B2
(45) Date of Patent: Oct. 31, 2006

(54) CROWN ETHER DERIVATIVES

(75) Inventors: Kyle R. Gee, Springfield, OR (US); Vladimir V. Martin, Eugene, OR (US)

(73) Assignee: Molecular Probes, Inc., Eugene, OR (US)

( * ) Notice: Subject to any disclaimer, the term of this patent is extended or adjusted under 35 U.S.C. 154(b) by 257 days.

(21) Appl. No.: 10/634,336

(22) Filed: Aug. 4, 2003

(65) Prior Publication Data
US 2004/0096978 A1 May 20, 2004

Related U.S. Application Data

(63) Continuation-in-part of application No. 10/026,302, filed on Dec. 19, 2001, now Pat. No. 6,962,992.

(60) Provisional application No. 60/258,266, filed on Dec. 20, 2000.

(51) Int. Cl.
C07D 225/00 (2006.01)
C07D 267/22 (2006.01)

(52) U.S. Cl. ...................... 540/465; 540/468
(58) Field of Classification Search ............... 540/465, 540/468
See application file for complete search history.

(56) References Cited

U.S. PATENT DOCUMENTS

| | | | |
|---|---|---|---|
| 4,520,110 A | 5/1985 | Stryer et al. |
| 4,542,104 A | 9/1985 | Stryer et al. |
| 4,843,158 A | 6/1989 | Smith |
| 4,859,582 A | 8/1989 | Stryer et al. |
| 5,055,556 A | 10/1991 | Stryer et al. |
| 5,096,831 A | 3/1992 | Chapoteau et al. |
| 5,134,232 A | 7/1992 | Tsien et al. |
| 5,227,487 A | 7/1993 | Haugland et al. |
| 5,242,805 A | 9/1993 | Naleway et al. |
| 5,248,782 A | 9/1993 | Haugland et al. |
| 5,405,975 A | 4/1995 | Kuhn et al. |
| 5,451,343 A | 9/1995 | Neckers et al. |
| 5,569,587 A | 10/1996 | Waggoner |
| 5,569,766 A | 10/1996 | Waggoner |
| 5,627,027 A | 5/1997 | Waggoner |
| 5,656,554 A | 8/1997 | Desai et al. |
| 5,773,227 A | 6/1998 | Kuhn et al. |
| 5,798,276 A | 8/1998 | Haugland et al. |
| 5,800,996 A | 9/1998 | Lee et al. |
| 5,846,737 A | 12/1998 | Kang |
| 5,863,727 A | 1/1999 | Lee et al. |
| 5,945,526 A | 8/1999 | Lee et al. |
| 6,008,373 A | 12/1999 | Waggoner et al. |
| 6,008,379 A | 12/1999 | Benson et al. |
| 6,048,982 A | 4/2000 | Waggoner |
| 6,124,135 A | 9/2000 | Leiner et al. |
| 6,140,494 A | 10/2000 | Hamilton et al. |
| 6,184,379 B1 | 2/2001 | Josel et al. |
| 6,221,606 B1 | 4/2001 | Benson et al. |
| 6,229,055 B1 | 5/2001 | Klaubert et al. |
| 6,335,440 B1 | 1/2002 | Lee et al. |
| 6,348,599 B1 | 2/2002 | Cummins et al. |
| 6,358,684 B1 | 3/2002 | Lee |
| 6,372,445 B1 | 4/2002 | Davis et al. |
| 6,403,807 B1 | 6/2002 | Singh et al. |
| 2002/0059684 A1 | 5/2002 | Diwu et al. |
| 2002/0064794 A1 | 5/2002 | Leung et al. |
| 2002/0077487 A1 | 6/2002 | Leung et al. |
| 2002/0164616 A1 | 11/2002 | Martin et al. |

FOREIGN PATENT DOCUMENTS

GB 2 372 749 B 7/2003
WO WO97/39064 10/1997

OTHER PUBLICATIONS

Charbonniere et al., Tetrahedron Letters (2000), 41(14), 2373-2376.*
Bulgakov, R.G., *The First Example of Chemluminescence of Fullerenes—Oxidation of C 60 by Ozone in Solution.*

(Continued)

*Primary Examiner*—Bruck Kifle
(74) *Attorney, Agent, or Firm*—Koren Anderson

(57) ABSTRACT

The invention describes crown ether chelators, including crown ethers having the formula

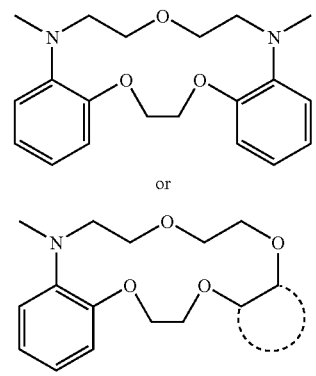

and aza-substituted and thia-substituted analogs thereof. These crown ethers may be substituted by a dye moiety, a chemically reactive group, a conjugated substance, or a combination thereof. Chelators that are substituted by fluorescent dyes are particularly useful as indicators for metal cations, particularly $Na^+$ and $K^+$ ions, and particularly where binding of the target ion results in a change in the fluorescence properties of the indicator that can be correlated with the ion concentration. Methods are provided for utilizing reactive groups on the chelators for conjugation to dyes, lipids and polymers and methods for enhancing entry of the indicators into living cells.

33 Claims, 6 Drawing Sheets

OTHER PUBLICATIONS

Lockhart, J.C. and M.E. Thompson, *Ligands for the Alkai Metals. Part 3. Further Examples of Nitorgen-containing 'Crown' Compounds*, J.C.S. Perkin I, 1997. p. 202-4.

R. Haugland *Molecular Probes Handbook of Fluorescent Probes and Research Chemicals*, 9th Edition, 2002 on CD-ROM.

Molecular Probes, *BioProbes* 32, 1999.
Molecular Probes, *BioProbes* 33, 2000.
Molecular Probes, *BioProbes* 34, 2000.
Molecular Probes, *BioProbes* 35, 2000.
International Search Report, dated Sep. 23, 2005.

* cited by examiner

CROWN ETHER DERIVATIVES

CROSS-REFERENCE TO RELATED APPLICATIONS

This application is a continuation-in-part of U.S. Ser. No. 10/026,302 filed Dec. 19, 2001 now U.S. Pat. No. 6,962,992, which claims priority to U.S. Ser. No. 60/258,266, Dec. 20, 2000; which disclosures are herein incorporated by reference.

FIELD OF THE INVENTION

The invention relates to derivatives of crown ether chelators, including chromophoric and fluorescent derivatives that are useful for chelating metal cations. Where the chelator is labeled with a fluorophore, it is an indicator useful for the detection, discrimination and quantification of metal cations. The chelators are optionally substituted one or more times with a chemically reactive group or a conjugated substance, such as a biological or nonbiological polymer, or a lipid.

BACKGROUND OF THE INVENTION

Metal ions play an important role in biological systems. Cells utilize metal ions for a wide variety of functions, such as regulating enzyme activity, protein structure, cellular signaling, as catalysts, as templates for polymer formation and as regulatory elements for gene transcription. Metal ions can also have a deleterious effect when present in excess of bodily requirements or capacity to excrete. A large number of natural and synthetic materials are known to selectively or non-selectively bind to or chelate metal ions. Ion chelators are commonly used in solution for in vivo control of ionic concentrations and detoxification of excess metals, and as in vitro buffers. When bound to a fluorophore, ion chelators are typically used as optical indicators of ions and are useful in the analysis of cellular microenvironments or dynamic properties of proteins, membranes and nucleic acids.

Such indicators are also useful for measuring ions in extracellular spaces; in vesicles; in vascular tissue of plants and animals; biological fluids such as blood and urine; in fermentation media; in environmental samples such as water, soil, waste water and seawater; and in chemical reactors. Optical indicators for ions are important for qualitative and quantitative determination of ions, particularly in living cells. Fluorescent indicators for metal cations also permit the continuous or intermittent optical determination of these ions in living cells, and in solutions containing the ions.

A variety of fluorescent indicators that are useful for the detection of biologically relevant soluble free metal ions (such as $Ca^{2+}$, $Mg^+$ and $Zn^{2+}$) have been described that utilize oxygen-containing anionic or polyanionic chelators to bind to metal ions. In particular, fluorescent indicators utilizing a polycarboxylate BAPTA chelator have been previously described (U.S. Pat. No. 4,603,209 to Tsien et al. (1986); U.S. Pat. No. 5,049,673 to Tsien et al. (1991); U.S. Pat. No. 4,849,362 to DeMarinis et al. (1989); U.S. Pat. No. 5,453,517 to Kuhn et al. (1995); U.S. Pat. No. 5,501,980 to Malekzadeh et al. (1996); U.S. Pat. No. 5,459,276 to Kuhn et al. (1995); U.S. Pat. No. 5,501,980 to Katerinopoulos et al. (1996); U.S. Pat. No. 5,459,276 to Kuhn et al. (1995). Some fluorescent indicators selective for $Li^+$, $Na^+$ and $K^+$ in aqueous or organic solution have also been described, based on the chemical modification of crown ethers (U.S. Pat. No. 5,134,232; and U.S. Pat. No. 5,405,975; Gromov et al, Russian Chemical Bulletin (1999) 48:6 p. 1190–1192; Lockhart et al, J. C. S. Perkin I (1977) p 202–204).

In general, a useful property for metal ion indicators is the ability to detect and/or quantify a selected metal ion in the presence of other metal ions. Discrimination of $Ca^{2+}$, $Na^+$ and $K^+$ ions in the presence of other metal ions is particularly useful for certain biological or environmental samples. For most biological applications, it is essential that the indicators be effective in aqueous solutions. It is also useful that indicators for biological applications be relatively insensitive to pH changes over the physiological range (pH 6–8) and sensitive to ion concentrations in the physiological range (for sodium, a $K_d$ of about 5 mM to about 20 mM). It is also beneficial if the indicator absorbs and emits light in the visible spectrum where biological materials have low intrinsic absorbance or fluorescence.

Also useful are chelators that possess a chemically reactive functional group, so that the chelating group can be attached to polymers for use in remote sensing of ions or enhancing the solubility or localization of the optical sensor. Many chelators bind to intracellular proteins, altering the chelator's metal binding properties. In addition, due to their relatively small size, they are readily sequestered non-selectively in intracellular vesicles, further limiting their effectiveness. One means of circumventing these problems is to attach the desired crown ether to a large, water-soluble polysaccharide, such as dextran or FICOL, by means of modification of the polysaccharide to allow covalent attachment of the indicator. Dextrans and FICOLs are especially suitable for this application, as they are low cost, optically transparent above about 250 nm and available in multiple ranges of molecular weights. Furthermore, polysaccharides and their conjugates are reasonably compatible with most biological materials and do not interact significantly with intracellular components. Although fluorescent polysaccharides have been previously described, as have indicator conjugates of dextrans, none possess the advantageous properties of the indicator conjugates of the current invention.

The crown ether chelators of the invention show significant ability to discriminate between metal ions under physiological conditions, particularly $Ca^{2+}$, $Na^+$ and $K^+$ ions. This selectivity can be tailored by careful selection of crown ether substituents. The compounds of the invention are typically soluble in aqueous solutions.

The compounds of the invention that act as indicators for target ions absorb and emit light in the visible spectrum and possess significant utility as a means of detecting and quantifying certain metal ion levels in living cells, biological fluids or aqueous solutions. Upon binding the target ion in the chelating moiety of the indicator, the optical properties of the attached fluorophore are generally affected in a detectable way, and this change is correlated with the presence of the ion according to a defined standard. Compounds having relatively long wavelength excitation and emission bands can be used with a variety of optical devices and require no specialized (quartz) optics, such as are required by indicators that are excited or that emit at shorter wavelengths. These indicators are suitable for use in fluorescence microscopy, flow cytometry, fluoroscopy, or any other application that currently utilize fluorescent metal ion indicators.

SUMMARY OF THE INVENTION

The present invention provides metal chelating compounds that are derivatives of crown ether compounds that bind many metal cations including physiological relevant levels of metal cations such as sodium. These metal chelating compounds find utility in detecting, quantitating and monitoring cations such as Na$^+$, Li$^+$, K$^+$, Ca$^{2+}$, Zn$^{2+}$ and Rb$^+$. A particular useful application is the binding of physiological levels of sodium ions in living cells wherein the compounds of the present invention provide for the detection, quantitation and monitoring of the intracellular sodium ions.

The metal chelating compounds of the present invention are derivatives of crown ether compounds and have the following formula:

Formula (II)

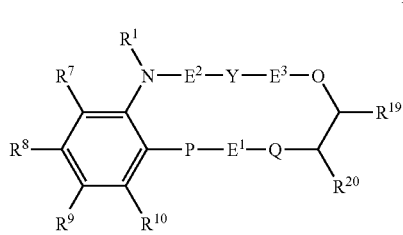

wherein the compound contains at least one oxygen atom and preferably three to five oxygen atoms in the crown of the compound. The oxygen atoms are preferably separated by —(CH$_2$)$_2$—. Crown ether compounds that contain an oxygen and nitrogen atom ortho to the benzo moiety find particular use in binding sodium ions and in generating a detectable signal when bound by an -L-DYE moiety at one of the benzo substitutents.

Thus, P and Q are independently O, S or NR$^3$, wherein each R$^3$ is independently H or C$_1$–C$_6$ alkyl. Typically P and Q are O.

More specifically, Y is O, S, NR$^4$ or is absent. R$^4$ is selected from the group consisting of H, -L-R$_X$, -L-S$_C$, -L-DYE, C$_1$–C$_{18}$ alkyl, aryl and heteroaryl ring system, which alkyl or ring system is optionally substituted by halogen, azido, nitro, nitroso, amino, C$_1$–C$_6$ alkylamino, C$_2$–C$_{12}$ dialkylamino, cyano, -L-R$_X$, -L-S$_C$, -L-DYE, C$_1$–C$_6$ alkyl or C$_1$–C$_6$ alkoxy that is itself optionally substituted by halogen, amino, hydroxy, —(SO$_2$)—R$^{15}$, —(SO$_2$)—O—R$^{15}$, —(C=O)—R$^{15}$, —(C=O)—O—R$^{16}$, or —(C=O)—NR$^{17}$R$^{18}$. R$^{15}$ is selected from the group consisting of H, C$_1$–C$_6$ alkyl, -L-R$_X$, -L-S$_C$ and -L-DYE and R$^{16}$ is selected from the group consisting of H, C$_1$–C$_6$ alkyl, benzyl, a biologically compatible esterifying group, a biologically compatible salt, -L-R$_X$, -L-S$_C$ and -L-DYE. R$^{17}$ and R$^{18}$ are independently selected from the group consisting of H, C$_1$–C$_6$ alkyl, C$_1$–C$_6$ carboxyalkyl, alpha-acyloxyalkyl, trialkylsilyl, a biologically compatible salt, -L-R$_X$, -L-S$_C$ and -L-DYE; or R$^{17}$ and R$^{18}$ taken in combination form a 5- or 6-membered aliphatic ring that optionally incorporates an oxygen atom;

R$_x$ is a reactive group that is capable of forming a covalent bond with another substance containing an appropriate reactive group to form a conjugated substance (S$_c$). Particularly useful reactive groups of the metal chelating compounds include carboxylic acid and activated esters of carboxylic acid for labeling amines and alcohols of biomolecules. Conjugated substances are intended to mean any biomolecule or non-biomolecule that contains a moiety capable of forming a covalent linkage with another moiety or is modified to contain such a reactive group. Particularly useful conjugated substances include proteins, peptides and non-biomolecule polymers. The covalent linkage (L) can be a single covalent bond or a series of stable bonds containing 1–20 non-hydrogen atoms including P, C, N, O and S.

E$^1$, E$^2$, and E$^3$ are independently —(CR$^5$$_2$)$_n$—, —(C(O)CH$_2$)$_n$—, —(CR$^5$$_2$)$_n$O(CR$^5$$_2$)$_n$— or E$^2$ is absent, where n=2, 3 or 4, and each R$^5$ is independently H or CH$_3$, or two R$^5$ moieties on adjacent carbons of one or more of E$^1$, E$^2$ or E$^3$, when taken in combination, form a 5- or 6-membered aliphatic ring.

R$^1$ is selected from the group consisting of -L-R$_X$, -L-S$_C$, -L-DYE, C$_1$–C$_{18}$ alkyl and C$_7$–C$_{18}$ arylalkyl, each of which is optionally substituted by halogen, azido, nitro, nitroso, amino, hydroxy, cyano, an aryl or heteroaryl ring system, —(SO$_2$)—R$^{15}$, —(SO$_2$)—O—R$^{15}$, —(C=O)—R$^{15}$, —(C=O)—O—R$^{16}$, —(C=O)—NR$^{17}$R$^{18}$, C$_1$–C$_6$ alkylamino, C$_2$–C$_{12}$ dialkylamino, C$_1$–C$_6$ alkyl or C$_1$–C$_6$ alkoxy and each of which are optionally further substituted by halogen, amino (—NR$^{17}$R$^{18}$), hydroxy, —(SO$_2$)—R$^{15}$, —(SO$_2$)—O—R$^{15}$, —(C=O)—R$^{15}$, —(C=O)—O—R$^{16}$ or —(C=O)—NR$^{17}$R$^{18}$.

A particularly preferred R$^1$ is represented by methyl or ethyl that is substituted by —(C=O)—O—R$^{16}$ or —(C=O)—R$^{15}$ wherein R$^{16}$ or R$^{15}$ is a methyl group. These particular substitutents appear to play a role in stabilizing the metal ion in the chelating ring of the present compounds.

R$^{19}$ and R$^{20}$ are independently selected from the group consisting of H, halogen, azido, nitro, nitroso, amino, cyano, -L-R$_X$, -L-S$_C$, -L-DYE, C$_1$–C$_6$ alkyl and C$_1$–C$_6$ alkoxy, each of which is itself optionally substituted by halogen, amino, hydroxy, —(SO$_2$)—R$^{15}$, —(SO$_2$)—O—R$^{15}$, —(C=O)—R$^{15}$, —(C=O)—O—R$^{16}$, or —(C=O)—NR$^{17}$R$^{18}$. Alternatively, R$^{19}$ and R$^{20}$ taken in combination form a fused six-membered benzo moiety that is optionally substituted by halogen, azido, nitro, nitroso, amino, cyano, -L-R$_X$, -L-S$_C$, -L-DYE, C$_1$–C$_6$ alkyl or C$_1$–C$_6$ alkoxy, each of which is itself optionally substituted by halogen, amino, hydroxy, —(SO$_2$)—R$^{15}$, —(SO$_2$)—O—R$^{15}$, —(C=O)—R$^{15}$, —(C=O)—O—R$^{16}$, or —(C=O)—NR$^{17}$R$^{18}$.

R$^7$, R$^8$, R$^9$ and R$^{10}$ are independently selected from the group consisting of H, halogen, azido, nitro, nitroso, amino, cyano, -L-R$_X$, -L-S$_C$, -L-DYE, C$_1$–C$_6$ alkyl or C$_1$–C$_6$ alkoxy, each of which is itself optionally substituted by halogen, amino, hydroxy, —(SO$_2$)—R$^{15}$, —(SO$_2$)—O—R$^{15}$, —(C=O)—R$^{15}$, —(C=O)—O—R$^{16}$, or —(C=O)—NR$^{17}$R$^{18}$. Alternatively, any two adjacent substituents R$^7$–R$^{10}$, taken in combination, form a fused six-membered benzo moiety, which is optionally substituted by halogen, azido, nitro, nitroso, amino, cyano, -L-R$_X$, -L-S$_C$, -L-DYE, C$_1$–C$_6$ alkyl or C$_1$–C$_6$ alkoxy, each of which is optionally substituted by halogen, amino, hydroxy, —(C=O)—R$^{15}$, —(C=O)—O—R$^{16}$, or —(C=O)—NR$^{17}$R$^{18}$. In addition, any two adjacent substituents R$^7$–R$^{10}$, or R$^{19}$ and R$^{20}$, taken in combination with each other, form a fused DYE wherein the dye shares the benzo moiety of the present compounds.

A particulary useful compound of the present invention is when R$^8$ or R$^9$ is represented by a -L-DYE or R$^8$ and R$^9$ taken in combination form a fused DYE. In addition, when a lipiphilic group such as an AM ester substitutes the DYE moiety the present compounds find use in binding in vivo metal cations. This is a particulary useful aspect of the present invention wherein certain embodiments of the compounds, such as compounds containing only one nitrogen atom and one benzo moiety, enter cells and bind target ions with better results compared to similar compounds.

The compounds of the present invention are useful for binding physiological relevant levels of cations, particularly sodium ions. When the present compounds comprise a DYE moiety the compounds find use to monitor, detect and quantitate such cations. Furthermore, compounds comprising a lipophilic group such as an AM or acetate ester group provide compounds that are cell permeable but are well retained in the cell after the lipophilic group is cleaved by nonspecific esterases resulting in a charged molecule.

DETAILED DESCRIPTION OF THE INVENTION

I. Definitions

Figure 1:
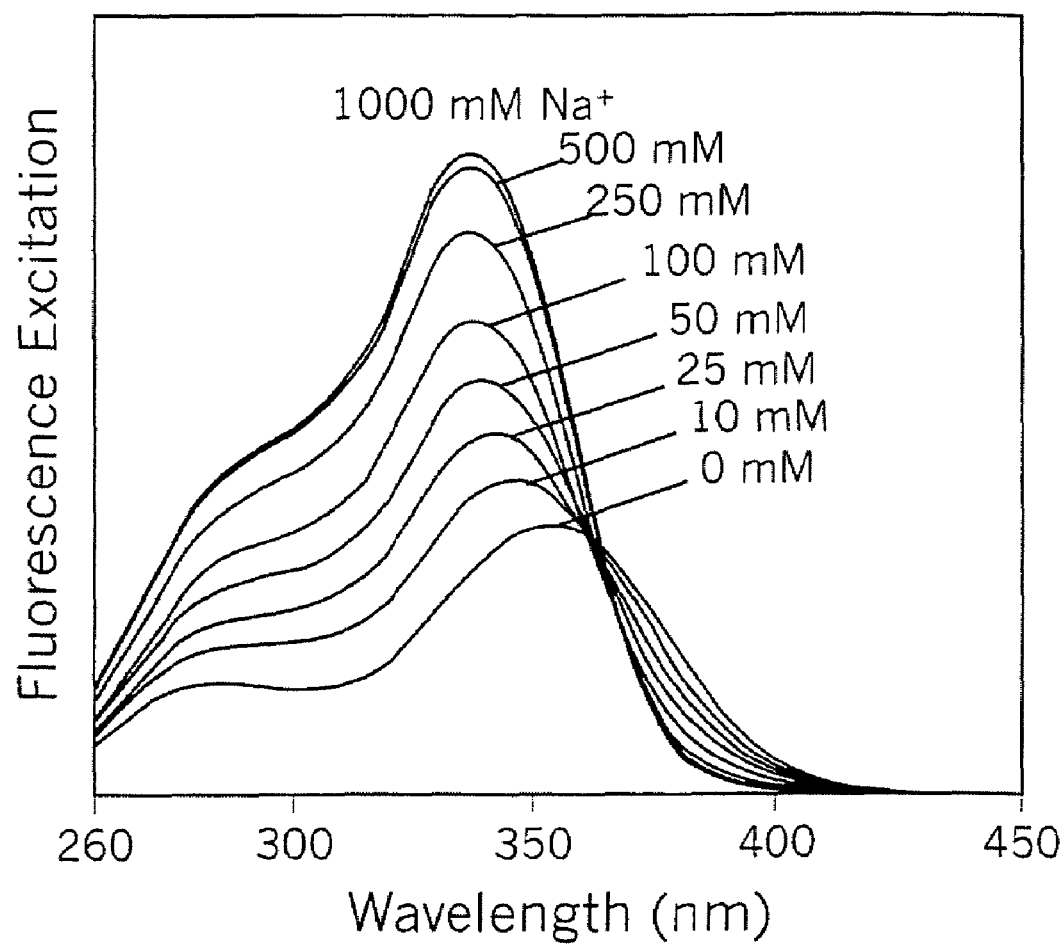
FIG. 1: Shows the $Na^+$-dependent fluorescence excitation spectra of Compound 51 in a series of solutions containing 0 to 1000 mM free $Na^+$, with fluorescence emission monitored at 510 nm (as described in Example 71).
Figure 2:
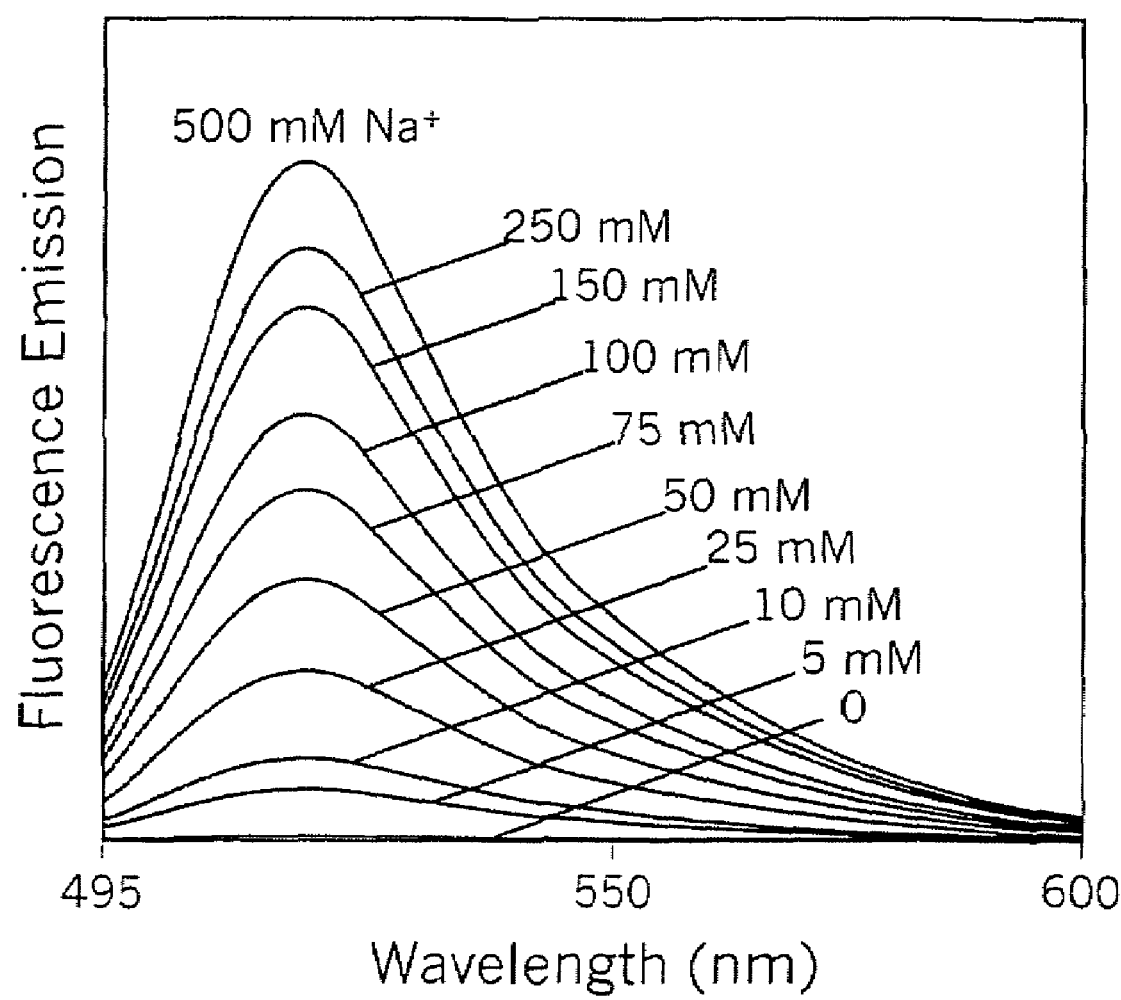
FIG. 2: Shows the $Na^+$-dependent fluorescence emission spectra of Compound 22 in a series of solutions containing 0 to 500 mM free $Na^+$, with excitation at 488 nm (as described in Example 71).

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise. Thus, for example, reference to "a fusion protein" includes a plurality of proteins and reference to "a fluorescent compound" includes a plurality of compounds and the like.

Unless defined otherwise, all technical and scientific terms used herein have the same meaning as commonly understood by one of ordinary skill in the art to which this invention is related. The following terms are defined for purposes of the invention as described herein.

The term "affinity" as used herein refers to the strength of the binding interaction of two molecules, such as a metal chelating compound and a metal ion or a positively charged moiety and a negatively charged moiety.

The term "alkyl" as used herein refers to a straight, branched or cyclic hydrocarbon chain fragment containing between about one and about twenty five carbon atoms (e.g. methyl, ethyl and the like). Straight, branched or cyclic hydrocarbon chains having eight or fewer carbon atoms will also be referred to herein as "lower alkyl". In addition, the term "alkyl" as used herein further includes one or more substitutions at one or more carbon atoms of the hydrocarbon chain fragment. Such substitutions include, but are not limited to: aryl; heteroaryl; halogen; alkoxy; amine (—NR'R"); carboxy and thio.

The term "amino" or "amine group" refers to the group —NR'R" (or NRR'R") where R, R' and R" are independently selected from the group consisting of hydrogen, alkyl, substituted alkyl, aryl, substituted aryl, aryl alkyl, substituted aryl alkyl, heteroaryl, and substituted heteroaryl. A substituted amine being an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, comprising the group —NRR'R" and its biologically compatible anionic counterions.

The term "aryl" as used herein refers to cyclic aromatic carbon chain having twenty or fewer carbon atoms, e.g., phenyl, naphthyl, biphenyl, and anthracenyl. One or more carbon atoms of the aryl group may also be substituted with, e.g., alkyl; aryl; heteroaryl; a halogen; nitro; cyano; hydroxyl, alkoxyl or aryloxyl; thio or mercapto, alkyl-, or arylthio; amino, alkylamino, arylamino, dialkyl-, diaryl-, or arylalkylamino; aminocarbonyl, alkylaminocarbonyl, arylaminocarbonyl, dialkylaminocarbonyl, diarylaminocarbonyl, or arylalkylaminocarbonyl; carboxyl, or alkyl- or aryloxycarbonyl; aldehyde; aryl- or alkylcarbonyl; iminyl, or aryl- or alkyliminyl; sulfo; alkyl- or alkylcarbonyl; iminyl, or aryl- or alkyliminyl; sulfo; alkyl- or arylsufonyl; hydroximinyl, or aryl- or alkoximinyl. In addition, two or more alkyl or heteroalkyl substituents of an aryl group may be combined to form fused aryl-alkyl or aryl-heteroalkyl ring systems (e.g., tetrahydronaphthyl). Substituents including heterocyclic groups (e.g., heteroaryloxy, and heteroaralkylthio) are defined by analogy to the above-described terms.

The term "arylalkyl" as used herein refers to an aryl group that is joined to a parent structure by an alkyl group as described above, e.g., benzyl, α-methylbenzyl, phenethyl, and the like.

The term "attachment site" as used herein refers to a site on a moiety or a molecule, e.g. a metal chelating compound, a fluorescent dye, a peptide or a protein, to which is covalently attached, or capable of being covalently attached, to a linker or another moiety.

The term "aqueous solution" as used herein refers to a solution that is predominantly water and retains the solution characteristics of water. Where the aqueous solution contains solvents in addition to water, water is typically the predominant solvent.

The term "cell permeable" as used herein refers to compounds of the present invention that are able to cross the cell membrane of live cells. Lipophilc groups that are covalently attached to the present compounds, typically on the DYE moiety, facilitate this permeability and live cell entry. Once inside the cells, the lipophilic groups are hydrolyzed resulting in charged molecules that are well retained in living cells. Particularly useful lipophilic groups include acetoxymethyl (AM) ester and acetate esters wherein once inside the cells the groups are cleaved by nonspecific esterases resulting in charged molecules.

The term "complex" as used herein refers to the association of two or more molecules, usually by non-covalent bonding.

The term "detectable response" as used herein refers to a change in or an occurrence of, a signal that is directly or indirectly detectable either by observation or by instrumentation and the presence or magnitude of which is a function of the presence of a target metal ion in the test sample. Typically, the detectable response is an optical response resulting in a change in the wavelength distribution patterns or intensity of absorbance or fluorescence or a change in light scatter, fluorescence quantum yield, fluorescence lifetime, fluorescence polarization, a shift in excitation or emission wavelength or a combination of the above parameters. The detectable change in a given spectral property is generally an increase or a decrease. However, spectral changes that result in an enhancement of fluorescence intensity and/or a shift in the wavelength of fluorescence emission or excitation are also useful. The change in fluorescence on ion binding is usually due to conformational or electronic changes in the indicator that may occur in either the excited or ground state of the fluorophore, due to changes in electron density at the ion binding site, due to quenching of fluorescence by the bound target metal ion, or due to any combination of these or other effects. Alternatively, the detectable response is an occurrence of a signal wherein the fluorophore is inherently fluorescent and does not produce a change in signal upon binding to a metal ion or biological compound.

The term "DYE" as used herein refers to a reporter molecule that is inherently fluorescent or demonstrates a change in fluorescence upon binding to a biological compound or metal ion, i.e., fluorogenic. Numerous fluorophores are known to those skilled in the art and include, but are not limited to, coumarin, acridine, furan, indole, borapolyazaindacene, cyanine, benzofuran, quinazolinone, benzazole, oxazine and xanthenes including fluoroscein, rhodamine, rosamine and rhodol, as well as other fluorophores described in RICHARD P. HAUGLAND, MOLECULAR PROBES HANDBOOK OF FLUORESCENT PROBES AND RESEARCH PRODUCTS ($9^{th}$ edition, CD-ROM, 2002). The DYE moiety may be substituted by substituents that enhance solubility, live cell permeability and alter spectra absorption and emission.

The term "heteroaryl" or "heteroaromatic ring system" as used herein refers to a 5- or 6-membered unsaturated ring that is optionally fused to an additional six-membered aromatic ring(s), or is fused to one 5- or 6-membered unsaturated ring containing one or more heteroatoms, and is optionally substituted as defined below. Each heteroaromatic ring contains at least 1 and as many as 3 heteroatoms that are selected from the group consisting of O, N or S in any combination. Specific examples of a heteroaryl ring system include, but are not limited to, substituted or unsubstituted derivatives of 2- or 3-furanyl; 2- or 3-thienyl; N-, 2- or 3-pyrrolyl; 2- or 3-benzofuranyl; 2- or 3-benzothienyl; N-, 2- or 3-indolyl; 2-, 3- or 4-pyridyl; 2-, 3- or 4-quinolyl; 1-, 3-, or 4-isoquinolyl; 2-, 4-, or 5(1,3-oxazolyl); 2-benzoxazolyl; 2-, 4-, or 5-(1,3-thiazolyl); 2-benzothiazolyl; 3-, 4-, or 5-isoxazolyl; N-, 2-, or 4-imidazolyl; N-, or 2-benzimidazolyl; 1- or 2-naphthofuranyl; 1- or 2-naphthothienyl; N-, 2- or 3-benzindolyl; 2-, 3-, or 4-benzoquinolyl; 1-, 2-, 3-, or 4-acridinyl. Preferably the heteroaryl substituent is substituted or unsubstituted 4-pyridyl, 2-thienyl, 2-pyrrolyl, 2-indolyl, 2-oxazolyl, 2-benzothiazolyl or 2-benzoxazolyl. More preferably, the heteroaryl substituent is 2-thienyl or 2-pyrrolyl.

The term "kit" as used refers to a packaged set of related components, typically one or more compounds or compositions.

The term "Linker" or "L" as used herein refers to a single covalent bond or a series of stable covalent bonds incorporating 1–20 nonhydrogen atoms selected from the group consisting of C, N, O, S and P that covalently attach the crown ether metal chelating compounds to another moiety such as a chemically reactive group, a DYE or a conjugated substance including biological and non-biological substances. A "cleavable linker" is a linker that has one or more covalent bonds that may be broken by the result of a reaction or condition. For example, an ester in a molecule is a linker that may be cleaved by a reagent, e.g. sodium hydroxide, resulting in a carboxylate-containing fragment and a hydroxyl-containing product.

The term "metal chelator" or "metal chelating compound" as used herein refers to a chemical compound that combines with a metal ion to form a chelate ring structure.

The term "metal ion" or "target metal ion" as used herein refers to any metal cation that is capable of being chelated by the present crwon ether chelate compounds. Typically, these metal ions are physiological and or nutritional relevant metal ion such as $Na^+$, $K^+$, $Zn^{2+}$ and $Ca^{2+}$. The term metal ion used herein also refers to the metal ions $Li^+$ and $Rb^+$.

The terms "protein" and "polypeptide" are used herein in a generic sense to include polymers of amino acid residues of any length. The term "peptide" is used herein to refer to polypeptides having less than 250 amino acid residues, typically less than 100 amino acid residues. The terms apply to amino acid polymers in which one or more amino acid residues are an artificial chemical analogue of a corresponding naturally occurring amino acid, as well as to naturally occurring amino acid polymers.

The term "Rx" or "reactive group" as used herein refers to a group that is capable of reacting with another chemical group to form a covalent bond, i.e. is covalently reactive under suitable reaction conditions, and generally represents a point of attachment for another substance. The reactive group is a moiety, such as carboxylic acid or succinimidyl ester, on the compounds of the present invention that is capable of chemically reacting with a functional group on a different compound to form a covalent linkage. Reactive groups generally include nucleophiles, electrophiles and photoactivatable groups.

The term "reporter molecule" as used herein refers to a chemical moiety that when covalently attached to the present crown ether compound is capable of generateing a detectable reposnse. Typically the reporter moleule is a DYE moiety.

The term "sample" as used herein refers to any material that may contain target metal ions, as defined above. Typically, the sample is a live cell or a biological fluid that comprises endogenous host cell proteins. Alternatively, the sample may be a buffer solution or an environmental sample containing target metal ions. The sample may be in an aqueous solution, a viable cell culture or immobilized on a solid or semi solid surface such as a polyacrylamide gel, membrane blot or on a microarray.

II. Compositions and Methods of Use

A. Components of the Crown Ether Chelate Compounds

The present invention provides derivatives of crown ether compounds that bind a wide range of metal cations including physiological relevant levels of metal cations such as sodium. These metal chelating compounds comprise a crown ether moiety, at least one benzo moiety, substituents well known in the art including linkers, chemically reactive groups and DYE moieties that function as reporter groups. The crown either moiety contains at least four heteroatoms, one of which is required to be a nitrogen atom and is located ortho to the benzo moiety. The remaining heteroatoms may be selected from the group consisting of nitrogen, oxygen and sulfur and are selected based on their ability to bind different metal cations with different affinity. Typically, in addition to the nitrogen atom there is also an oxygen atom ortho to the benzo moiety that faciliates binding of target metal ions.

Furthermore, the substituents on the nitrogen atom are further used to alter the affinity for particular metal ions under different environmental conditions.

The present compounds find utility in binding target metal ions in a sample. The sample includes live cells or a biological fluid that comprises endogenous host cell proteins, buffer solutions and environmental samples. Therefore, when the present crown ether compounds comprise a DYE moiety they find utility in quantitating, monitoring and detecting target metal ions. Typically, the DYE moiety is directly attached to the benzo moiety or two of the benzo substituents when taken in combination form a fused DYE moiety. Detection of target metal ions can also be accomplished in live cells wherein the DYE moiety comprises a lipophilic group such as an AM or acetate ester that allows for entry across the live cell membrane. Once inside the cells nonspecific esterases cleave the AM or acetate ester resulting a charged molecule that is well retained in the cell. These present compounds are particularly useful for binding physiological relevant levels of sodium, potassium or calcium cations.

1. Chelating Moiety

The compounds of the invention are represented by the following two formulas:

Formula (I)

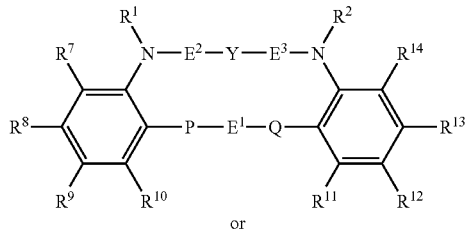

or

Formula (II)

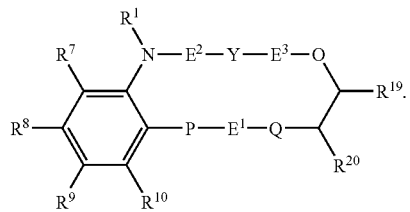

The heteroatom Y is O, S, $NR^4$ or is absent where $R^4$ is H, a $C_1$–$C_{18}$ alkyl, or an aryl or heteroaryl ring system. The $R^4$ alkyl or ring system substituent is optionally substituted one or more times by halogen, azido, nitro, nitroso, amino, alkylamino having 1–6 carbons, dialkylamino having 2–12 carbons, cyano, or $R^4$ is substituted one or more times by a $C_1$–$C_6$ alkyl or $C_1$–$C_6$ alkoxy that is itself optionally substituted one or more times by halogen, amino, hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$. Alternatively, $R^4$ is, or is substituted by -L-$R_X$, -L-$S_C$, or -L-DYE.

In one aspect of the invention Y is O and in another aspect Y is absent provided that $E^2$ is also absent.

$R^{15}$ is independently H or $C_1$–$C_6$ alkyl. Each $R^{16}$ is H, a $C_1$–$C_6$ alkyl, a benzyl, or forms an ester (e.g., $R^{16}$ is an alpha-acyloxyalkyl, a trialkylsilyl, or any other biologically compatible esterifying group). Additionally, any $R^{16}$ is a biologically compatible salt. $R^{17}$ and $R^{18}$ are independently H or $C_1$–$C_6$ alkyl or $C_1$–$C_6$ carboxyalkyl, or an alpha-acyloxyalkyl, trialkylsilyl, or any other biologically compatible esterifying group, or a biologically compatible salt. Alternatively, $R^{17}$ and $R^{18}$ when taken in combination form a 5- or 6-membered aliphatic ring that optionally incorporates an oxygen atom. In addition, one or more of a $R^{15}$, $R^{16}$, $R^{17}$, or $R^{18}$ is permitted to be -L-$R_X$, -L-$S_C$, or -L-DYE.

Each L is independently a covalent linkage. Each $R_X$ is independently a chemically reactive group. Each $S_C$ is independently a conjugated substance. Each DYE is independently a reporter molecule that is a chromophore that maximally absorbs light at a wavelength greater than 320 nm.

The heteroatoms P and Q are independently selected from O, S, or $NR^3$, where each $R^3$ is independently H or an alkyl having 1–6 carbons. In one aspect of the invention P and Q are both O.

In another aspect of the invention, P and Q are O, and Y is $NR^4$. Typically, P, Q, and Y are each O or Y is absent and P and Q are O. Careful selection of the nature of the P, Q, and Y heteroatoms permits the moderation of the selectivity and binding affinity of the resulting crown ether compound.

$E^1$, $E^2$, and $E^3$ each independently have the formula —($CR^5_2$)$_n$—, or —[C(O)$CH_2$]$_n$—, —($CR^5_2$)$_n$O($CR^5_2$)$_n$— or $E^2$ is absent where n is 2, 3 or 4. Each $R^5$ is independently H or methyl, or the $R^5$ moieties on adjacent carbon atoms of each chain, when taken in combination, forms a 5- or 6-membered aliphatic ring. For a given E moiety, each $R^5$ is typically H and n is 2. Where n is 2 for each E moiety, the resulting compound is known as a 15-crown-5 crown ether, having 15 atoms in the chelating ring itself, of which 5 are heteroatoms.

Alternatively, E2 is absent or a E moiety is —($CR^5_2$)$_n$O ($CR^5_2$)$_n$— resulting in a chelating ring with a different number of total atoms and possible heteroatoms such as oxygen.

In one aspect of the invention $E^1$, $E^2$, and $E^3$ are each —($CH_2$)$_2$— and Y, P and Q are each oxygen. In another aspect, $E^2$ is absent and P and Q are oxygen wherein Y is absent and $E^1$ and $E^3$ are each —($CH_2$)$_2$—. In yet another aspect of the invention at least one of $E^1$, $E^2$, or $E^3$ is —($CR^5_2$)$_n$O($CR^5_2$)$_n$— wherein Y, P and Q are each oxygen and the remaining E moieties are —($CH_2$)$_2$—.

Formula (I) contains the amine substituents $R^1$ and $R^2$, however Formula (II) contains only $R^1$, the second nitrogen having been replaced by a divalent oxygen atom. Thus, it is understood that while the amine substitutents, R1 and R2, are referred to in plural only one is intended for compounds represented by formula (II). These amine substituents are independently H, $C_1$–$C_{18}$ alkyl, or $C_7$–$C_{18}$ arylalkyl. Where $R^1$ or $R^2$ is alkyl or arylalkyl, it is optionally substituted one or more times by halogen, azido, nitro, nitroso, amino, hydroxy, $C_1$–$C_6$ alkylamino, $C_2$–$C_{12}$ dialkylamino, cyano, or by an aryl or heteroaryl ring system, or by —($SO_2$)—$R^{15}$, —($SO_2$)—O—$R^{15}$, —(C=O)—$R^{15}$, —(C=O)—O—$R^{16}$, or —(C=O)—$NR^{17}R^{18}$; or by a $C_1$–$C_6$ alkyl or $C_1$–$C_6$ alkoxy that is itself optionally substituted one or more times by halogen, amino, hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$. Alternatively, $R^1$ and $R^2$ are optionally -L-$R_X$, -L-$S_C$, or -L-DYE.

Where the $R^1$ and $R^2$ substituents are not -L-$R_X$, -L-$S_C$, or -L-DYE, they are typically both a lower alkyl that is substituted one or more times by carboxylic acids, by carboxylic acid esters, by carboxylic acid amides, or by cyano. Where $R^1$ and $R^2$ incorporate carboxylic acid esters they are typically not cleaved by esterase but instead function to stabilize the bound metal ion in the chelate ring. Thus $R^1$, and $R^2$ when present, are typically a methyl or ethyl that is substituted by a carboxylic acid containing group such as —(C=O)—$R^{15}$ or —(C=O)—O—$R^{16}$ wherein $R^{15}$ and $R^{16}$ are each a methyl or ethyl. Selection of the precise nature of $R^1$ and $R^2$ can greatly affect the binding selectivity and affinity of the resulting compound for a target ion (see, Table 1 and 2).

The nature of the $R^1$ and $R^2$ substituents in a large part determines the response of the indicators to particular target metal ions. For example, where the crown ether derivatives have the formula

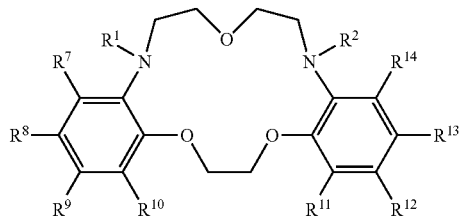

where $R^1$ and $R^2$ are each methoxycarbonylmethyl selectively bind sodium ions with a dissociation constant ($K_d$) of approximately 20–100 mM, and are relatively insensitive to the presence of potassium ions. In particular, the sodium ion $K_d$ values typically rise less than about 10% when measured in the presence of 100 mM potassium ion.

The Formula (II) substituents $R^{19}$ and $R^{20}$ are represented by H, halogen, azido, nitro, nitroso, amino, cyano, -L-$R_X$, -L-$S_C$, -L-DYE, $C_1$–$C_6$ alkyl and $C_1$–$C_6$ alkoxy, each of which is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$. Alternatively, $R^{19}$ and $R^{20}$ taken in combination form a fused six-membered benzo moiety that is optionally substituted by halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$. In one aspect of the invention, $R^{19}$ and $R^{20}$ are both hydrogen. In another aspect, $R^{19}$ and $R^{20}$ form a benzo moiety that is optionally substituted resulting in a crown ether chelate compound with two benzo moieties wherein only one benzo moiety has a nitrogen atom that is ortho to the benzo moiety.

The benzo substituents $R^7$–$R^{10}$, and $R^{11}$–$R^{14}$ when present, are independently H, halogen, azido, nitro, nitroso, amino, cyano; or -L-$R_X$, -L-$S_C$, or -L-DYE; or $C_1$–$C_6$ alkyl or $C_1$–$C_6$ alkoxy that is itself optionally substituted one or more times by halogen, amino, hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$.

Alternatively, two adjacent substituents of $R^7$–$R^{14}$, when taken in combination, form a fused six-membered benzo moiety, which is optionally substituted one or more times by a halogen, azido, nitro, nitroso, amino, cyano, -L-$R_X$, -L-$S_C$, or -L-DYE; or by a $C_1$–$C_6$ alkyl or $C_1$–$C_6$ alkoxy, which is itself optionally substituted one or more times by halogen, amino, hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$.

Furthermore, the present compounds comprise a fused DYE wherein two adjacent substituents of $R^7$–$R^{14}$, when taken in combination with each other, and with the aromatic ring they are bound to, form a fused DYE. In this way the benzo moiety of the present compounds is also part of a DYE moiety.

The compounds of the invention represented by Formula (I) are substituted by at least one -L-DYE, -L-$R_X$ or -L-$S_C$ at one or more of $R^1$, $R^2$, $R^4$, and $R^7$–$R^{14}$; or two of $R^7$–$R^{14}$, taken in combination, form a fused DYE. In one embodiment, the compounds of the invention are substituted by exactly one -L-DYE moiety, which is bound at $R^1$, $R^2$, an $R^4$, or one of $R^7$–$R^{14}$, or is a fused DYE moiety at two adjacent substituents of $R^7$–$R^{14}$. The DYE moiety is typically bound at one of $R^7$–$R^{11}$, preferably at $R^9$ or $R^8$, or is bound at $R^4$ where Y is $NR^4$. In one embodiment, compounds that are substituted by exactly one -L-DYE moiety are optionally further substituted by -L-$R_X$ or -L-$S_C$, typically at $R^1$, $R^2$, $R^4$, or one of $R^7$–$R^{14}$.

In another embodiment, the compound of the invention is substituted by exactly two DYE moieties, which may be the same or different, and may be bound by a covalent linkage L or fused to the crown ether chelate. In one embodiment of the invention, a first -L-DYE moiety is bound at one of $R^7$–$R^{10}$, while the second -L-DYE moiety is bound at one of $R^{11}$–$R^{14}$. Typically, the first -L-DYE moiety is bound at $R^9$, while the second -L-DYE moiety is bound at $R^{12}$, or a DYE moiety is fused at $R^8$ and $R^9$ and additionally at $R^{12}$ and $R^{13}$.

2. Linkers of the Crown Ether Chelate Compounds

The crown ether chelate compounds of the present invention typically comprise a linker that is used to covalently attach a DYE moiety, conjugated substance or reactive group to the compound. When present, the linker is a single covalent bond or a series of stable bonds. Thus, the reporter molecule, conjugated substance or reactive group may be directly attached (where Linker is a single bond) to the crown ether chelate or attached through a series of stable bonds. When the linker is a series of stable covalent bonds the linker typically incorporates 1–20 nonhydrogen atoms selected from the group consisting of C, N, O, S and P. In addition, the covalent linkage can incorporates a platinum atom, such as described in U.S. Pat. No. 5,714,327. When the linker is not a single covalent bond, the linker may be any combination of stable chemical bonds, optionally including, single, double, triple or aromatic carbon-carbon bonds, as well as carbon-nitrogen bonds, nitrogen-nitrogen bonds, carbon-oxygen bonds, sulfur-sulfur bonds, carbon-sulfur bonds, phosphorus-oxygen bonds, phosphorus-nitrogen bonds, and nitrogen-platinum bonds. Typically the linker incorporates less than 15 nonhydrogen atoms and are composed of any combination of ether, thioether, thiourea, amine, ester, carboxamide, sulfonamide, hydrazide bonds and aromatic or heteroaromatic bonds. Typically the linker is a single covalent bond or a combination of single carbon-carbon bonds and carboxamide, sulfonamide or thioether bonds. The bonds of the linker typically result in the following moieties that can be found in the linker: ether, thioether, carboxamide, thiourea, sulfonamide, urea, urethane, hydrazine, alkyl, aryl, heteroaryl, alkoky, cycloalkyl and amine moieties. Examples of L include substituted or unsubstituted polymethylene, arylene, alkylarylene, arylenealkyl, or arylthio.

In one embodiment, L contains 1–6 carbon atoms; in another, L comprises a thioether linkage. In another embodiment, L is or incorporates the formula —($CH_2$)$_d$(CONH($CH_2$)$_e$)$_z$— or —O($CH_2$)$_d$(CONH($CH_2$)$_e$)$_z$—, where d is an integer from 0–5, e is an integer from 1–5 and z is 0 or 1. In a further embodiment, L is or incorporates the formula —O—(CH$_2$)—. In yet another embodiment, L is or incorporates a phenylene or a 2-carboxy-substituted phenylene.

Any combination of linkers may be used to attach the DYE, Rx or Sc and the crown ether chelate together, typically a compound of the present invention when attached to more than one DYE, Rx or Sc will have one or two linkers attached that may be the same or different. The linker may also be substituted to alter the physical properties of the crown ether chelate compound, such as binding affinity of the chelating moiety and spectral properties of the dye.

Another important feature of the linker is to provide an adequate space between the crown ether chelate moiety and the DYE, Rx or Sc so as to prevent these substituents from providing a steric hinderance to the binding of the target metal ion for the chelating moiety of the present compounds. Therefore, the linker of the present compounds is important for (1) attaching DYE, Rx or Sc to the metal chelating moiety, (2) providing an adequate space between DYE, Rx or Sc and the metal chelating moiety so as not to sterically hinder the affinity of the chelating moiety and the zinc ions and (3) for altering the affinity of the chelating moiety for the target ions either by the choice of the atoms of the linker or indirectly by addition of substituents to the linker.

However, it is important to understand that a linker is not an essential component of the present compounds. Depending on the reporter molecule, a linker may not be necessary wherein the reporter molecule shares atoms with the metal chelating moiety, i.e. a fused DYE. A reporter molecule that exemplifies this is the dye benzofuran wherein one of the benzene rings of the dye is also one of the benzene rings of the metal chelating moiety. In addition, compounds represented for Formula (II) may not be substituted by a moiety that incorporates a linker.

3. DYE Moiety of the Crown Ether Chelate Compounds

The DYE moiety of the present invention functions as a reporter molecule to confer a detectable signal, directly or indirectly, to the target metal ions. This results in the ability to detect, monitor and quantitate target metal ions in a sample.

The DYE moiety includes without limit a fluorophore, a chromophore, a fluorescent protein and an energy transfer pair. When the DYE moiety is a chromophore the crown ether chelate compounds are chromogenic indicators, or more preferably, the DYE moiety is a fluorophore, resulting in a compound that is a fluorogenic indicator for target ions, preferably sodium ions. Therefore, binding a sodium ion with a crown ether compound of the resent invention results in a detectable optical response that can be correlated to the presence of sodium ions.

Where the detectable response is a fluorescence response, it is typically a change in fluorescence, such as a change in the intensity, excitation or emission wavelength distribution of fluorescence, fluorescence lifetime, fluorescence polarization, or a combination thereof. Preferably, the detectable optical response upon binding a target sodium ion is a change in fluorescence intensity that is greater than approximately 10-fold, more preferably greater than 50-fold, and most preferably more that 100-fold. This large increase in fluorescent signal over baseline has not been previously observed with other sodium indicators that comprise a different metal chelating moiety. In another aspect, the detectable optical response upon binding the target metal ion is a shift in maximal excitation or emission wavelength that is greater than about 20 nm, more preferably greater than about 30 nm. Sodium and potassium indicators of the type that exhibit significant excitation and/or emission shifts have not been previously described.

The DYE moiety is any chemical moiety that exhibits an absorption maximum beyond 320 nm, that is bound to the crown ether chelate by a covalent linkage L, or that is fused to the crown ether chelate. A preferred embodiment for detecting sodium ions in live cells is a fluorogenic crown ether chelate compound wherein the DYE moiety is substituted with a lipophilic group. As described above, the covalent linkage can be a single covalent bond or a combination of stable chemical bonds. The covalent linkage binding the DYE moiety to the crown ether chelator is typically a single bond, but optionally incorporates 1–20 nonhydrogen atoms selected from the group consisting of C, N, O, P, and S.

A wide variety of chemically reactive fluorescent dyes that may be suitable for incorporation into the compounds of the invention are already known in the art (RICHARD P. HAUGLAND, MOLECULAR PROBES HANDBOOK OF FLUORESCENT PROBES AND RESEARCH PRODUCTS (Supra); BIOPROBES 32 (December 1999); BIOPROBES 33 (February 2000); BIOPROBES 34 (May 2000); and BIOPROBES 35 (November 2000)). The spectral properties of candidate dyes in solution or when conjugated to proteins such as IgG are known or are readily measured using an absorption spectrometer or a spectrofluorometer.

Thus, the DYE moiety of the present invention include, without limitation; a pyrene, an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a carbocyanine (including any corresponding compounds in U.S. Ser. No. 09/557,275; US Publication Nos. 2002/0077487 and 2002/0064794 and U.S. Pat. Nos. 6,403,807; 6,348,599; 5,486,616; 5,268,486; 5,569,587; 5,569,766; 5,627,027 and 6,048,982), a carbostyryl, a porphyrin, a salicylate, an anthranilate, an azulene, a perylene, a pyridine, a quinoline, a borapolyazaindacene (including any corresponding compounds disclosed in U.S. Pat. Nos. 4,774,339; 5,187,288; 5,248,782; 5,274,113; and 5,433,896), a xanthene (including any corresponding compounds disclosed in U.S. Pat. Nos. 6,162,931; 6,130,101; 6,229,055; 6,339,392; 5,451,343 and US Publication No. 2002/0059684), an oxazine or a benzoxazine, a carbazine (including any corresponding compounds disclosed in U.S. Pat. No. 4,810,636), a phenalenone, a coumarin (including an corresponding compounds disclosed in U.S. Pat. Nos. 5,696,157; 5,459,276; 5,501,980 and 5,830,912), a benzofuran (including an corresponding compounds disclosed in U.S. Pat. Nos. 4,603,209 and 4,849,362) and benzphenalenone (including any corresponding compounds disclosed in U.S. Pat. No. 4,812,409) and derivatives thereof. As used herein, oxazines include resorufins (including any corresponding compounds disclosed in U.S. Pat. No. 5,242,805), aminooxazinones, diaminooxazines, and their benzo-substituted analogs.

Where the DYE moiety is a xanthene, the dye is optionally a fluorescein, a rhodol (including any corresponding compounds disclosed in U.S. Pat. Nos. 5,227,487 and 5,442,045), or a rhodamine (including any corresponding compounds in U.S. Pat. Nos. 5,798,276 and 5,846,737). As used herein, fluorescein includes benzo- or dibenzofluoresceins, seminaphthofluoresceins, or naphthofluoresceins. Similarly, as used herein rhodol includes seminaphthorhodafluors (including any corresponding compounds disclosed in U.S. Pat. No. 4,945,171). Fluorinated xanthene dyes have been described previously as possessing particularly useful fluorescence properties (Int. Publ. No. WO 97/39064 and U.S. Pat. No. 6,162,931).

Alternatively, the DYE moiety is a xanthene that is bound via an L that is a single covalent bond at the 9-position of the xanthene. Preferred xanthenes include derivatives of 3H-xanthen-6-ol-3-one bound at the 9-position, derivatives of 6-amino-3H-xanthen-3-one bound at the 9-position, or derivatives of 6-amino-3H-xanthen-3-imine bound at the 9-position.

Preferred DYE moieties of the present invention include xanthene (including rhodol, fluorescein, rhodamine), benzofuran, indole, carbocyanine, quinazolinone, a benzazole, oxazine, coumarin and borapolyazaindacene. The xanthene dyes of this invention comprise both compounds substituted and unsubstituted on the carbon atom of the central ring of the xanthene by substituents typically found in the xanthene-based dyes such as phenyl and substituted-phenyl moieties. In addition, a preferred DYE moiety includes a xanthene-based moity such as fluorescein that has a lipophilic group substited on the oxygen atom. Most preferred dyes are rhodamine, fluorescein, borapolyazaindacene, indole and benzofuran. The choice of the dye attached to the chelating moiety will determine the crown ether chelate compound's absorption and fluorescence emission properties as well as its live cell properties, i.e. substituted lipophilic groups Typically the DYE moiety contains one or more aromatic or heteroaromatic rings, that are optionally substituted one or more times by a variety of substituents, including without limitation, halogen, nitro, sulfo, cyano, alkyl, perfluoroalkyl, alkoxy, alkenyl, alkynyl, cycloalkyl, arylalkyl, acyl, aryl or heteroaryl ring system, benzo, or other substituents typically present on chromophores or fluorophores known in the art.

In one aspect of the invention, the DYE moiety has an absorption maximum beyond 480 nm. In a particularly useful embodiment, the DYE moiety absorbs at or near 488 nm to 514 nm (particularly suitable for excitation by the output of the argon-ion laser excitation source) or near 546 nm (particularly suitable for excitation by a mercury arc lamp). The DYE moiety may be a chromophore, resulting in a compound that acts as a chromogenic indicator, or more preferably, DYE is additionally a fluorophore, resulting in a compound that is a fluorescent indicator.

Selected sulfonated DYE moieties also exhibit advantageous properties, and include sulfonated pyrenes, coumarins, carbocyanines, and xanthenes (as described in U.S. Pat. Nos. 5,132,432; 5,696,157; 5,268,486; 6,130,101). Sulfonated pyrenes and coumarins are typically excited at wavelengths below about 450 nm (U.S. Pat. Nos. 5,132,432 and 5,696,157).

Fluorescent proteins also find use as DYE moieties for the crown ether chelate compounds of the present invention. Examples of fluorescent proteins include green fluorescent protein (GFP) and the phycobiliproteins and the derivatives thereof. The fluorescent proteins, especially phycobiliproteins, are particularly useful for creating tandem dye-reporter molecules. These tandem dyes comprise a fluorescent protein and a fluorophore for the purposes of obtaining a larger Stokes shift, wherein the emission spectra are farther shifted from the wavelength of the fluorescent protein's absorption spectra. This property is particularly advantageous for detecting a low quantity of a target sodium ion in a sample wherein the emitted fluorescent light is maximally optimized; in other words, little to none of the emitted light is reabsorbed by the fluorescent protein. For this to work, the fluorescent protein and fluorophore function as an energy transfer pair wherein the fluorescent protein emits at the wavelength that the acceptor fluorophore absorbs and the fluorophore then emits at a wavelength farther from the fluorescent proteins than could have been obtained with only the fluorescent protein. Alternatively, the fluorophore functions as the energy donor and the fluorescent protein is the energy acceptor. Particularly useful fluorescent proteins are the phycobiliproteins disclosed in U.S. Pat. Nos. 4,520,110; 4,859,582; 5,055,556 and the fluorophore bilin protein combinations disclosed in U.S. Pat. No. 4,542,104. Alternatively, two or more fluorophore dyes can function as an energy transfer pair wherein one fluorophore is a donor dye and the other is the acceptor dye including any dye compounds disclosed in U.S. Pat. Nos. 6,358,684; 5,863,727; 6,372,445; 6,221,606; 6,008,379; 5,945,526; 5,863,727; 5,800,996; 6,335,440; 6,008,373; 6,184,379; 6,140,494 and 5,656,554.

In one aspect of the invention, the compound of the invention has the formula

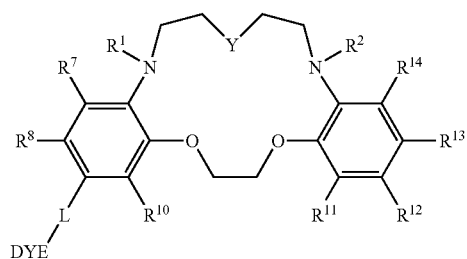

where Y is either O or NR$^4$; and the DYE moiety is an indole, a coumarin, a stilbene, a xanthene, or a polyazaindacene. In this embodiment, preferably the DYE moiety is a xanthene, a polyazaindacene, or an oxazine.

In one aspect of the invention, the compounds of the invention are fluorescent indicators having the following structure:

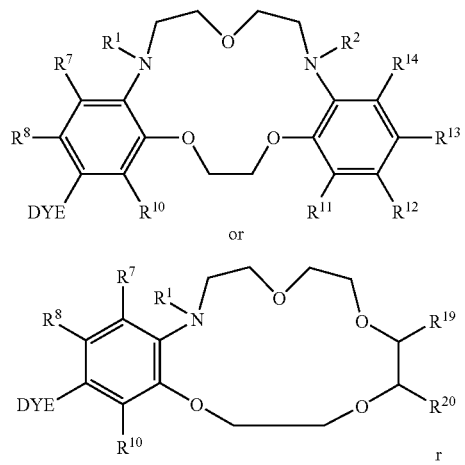

wherein the linker is a single covalent bond. These indicators typically exhibit a low fluorescence quantum efficiency in the absence of metal ions. However, in the presence of increasing metal ion concentration the fluorescence quantum efficiency rises dramatically. For example, selected indicators of this family exhibit a fluorescence signal increase of over 100-times between zero and a saturating sodium concentration. Other selected indicators of the invention exhibit a shift of the wavelength of the absorption (excitation) maximum, emission maximum, or both, upon binding the target ion. It appears that having the DYE moiety covalently attached or fused to the benzo moiety of the crown ether chelate compounds provides an additional channel, in addition to the chelate ring, to conduct electron density changes that occur upon metal binding, resulting in larger optical change. This is true for compounds represented by Formula (I) or (II)

In another aspect of the invention, the compounds of the invention are fluorescent indicators having the following structure:

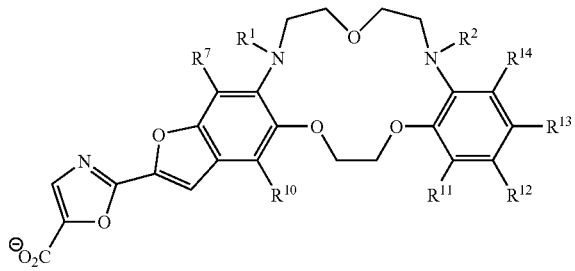

This class of indicators, in which at least one of the aromatic rings of the crown ether portion of the indicator is also incorporated in the DYE moiety, typically exhibit ratiometric fluorescence excitation changes in response to changing metal ion concentration. That is, there is a shift in the excitation maximum wavelength in the presence of increasing metal ion concentrations.

In one embodiment of this aspect, $R^1$ and $R^2$ are $C_1$–$C_6$ alkyl that are substituted one or more times by cyano, an aryl or heteroaryl ring system, or by —(C=O)—O—$R^{16}$ or —(C=O)—$NR^{17}R^{18}$, where $R^{16}$ is H, a $C_1$–$C_6$ alkyl, a benzyl, a biologically compatible esterifying group, or a biologically compatible salt; and $R^{17}$ and $R^{18}$ are independently H, $C_1$–$C_6$ alkyl, $C_1$–$C_6$ carboxyalkyl, an alpha-acyloxymethyl, or a biologically compatible salt. The substituents $R^7$, $R^{10}$, and $R^{11}$–$R^{14}$, are independently H, chloro, bromo, fluoro, nitro, amino, or cyano; or $C_1$–$C_6$ alkyl or $C_1$–$C_6$ alkoxy that is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$.

In one embodiment of this aspect, $R^1$ and $R^2$ are $C_1$–$C_6$ alkyl that are substituted one or more times by cyano, an aryl or heteroaryl ring system, or by —(C=O)—O—$R^{16}$ or —(C=O)—$NR^{17}R^{18}$, where $R^{16}$ is H, a $C_1$–$C_6$ alkyl, a benzyl, a biologically compatible esterifying group, or a biologically compatible salt; and $R^{17}$ and $R^{18}$ are independently H, $C_1$–$C_6$ alkyl, $C_1$–$C_6$ carboxyalkyl, an alpha-acyloxymethyl, or a biologically compatible salt. The substituents $R^7$ $R^8$, $R^{10}$, and $R^{11}$–$R^{14}$, are independently H, chloro, bromo, fluoro, nitro, amino, or cyano; or $C_1$–$C_6$ alkyl or $C_1$–$C_6$ alkoxy that is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$. The DYE moiety is a polyazaindacene, an oxazine, or a xanthene, which is optionally substituted one or more times by halogen, nitro, sulfo, cyano, an aryl or heteroaryl ring system, or benzo, or alkyl, perfluoroalkyl, alkoxy, alkenyl, alkynyl, cycloalkyl, arylalkyl, acyl, or carboxylic acids or carboxylic acid esters, the alkyl portions of which contain fewer than 20 carbons.

An additional selected embodiment of the invention has the formula

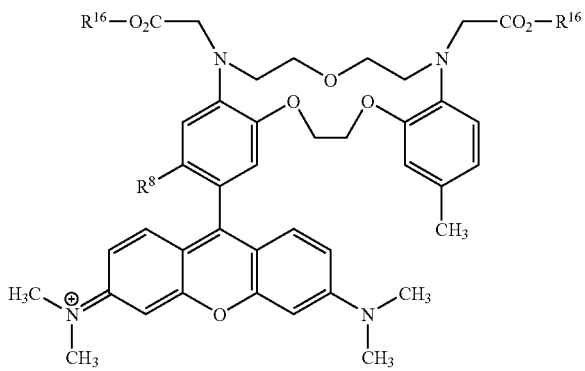

where $R^8$ and $R^{16}$ are defined as above.

An additional selected embodiment of the invention has the formula

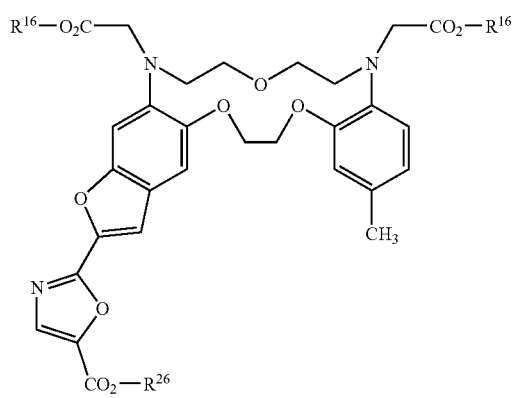

or the formula

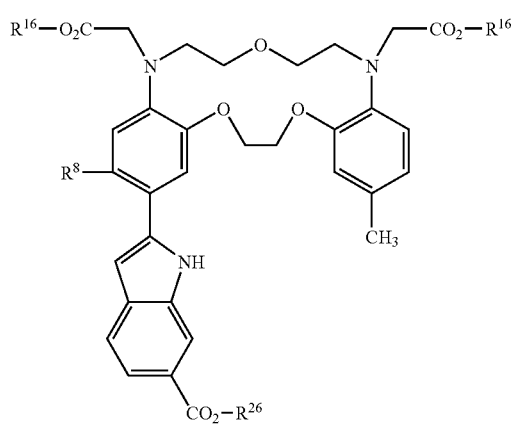

where $R^8$ and $R^{16}$ are defined as above, and $R^{26}$ is H, a $C_1$–$C_6$ alkyl, a benzyl, or is an alpha-acyloxyalkyl or a trialkylsilyl or other biologically compatible esterifying group, or is a biologically compatible salt.

An additional selected embodiment of the invention has the formula

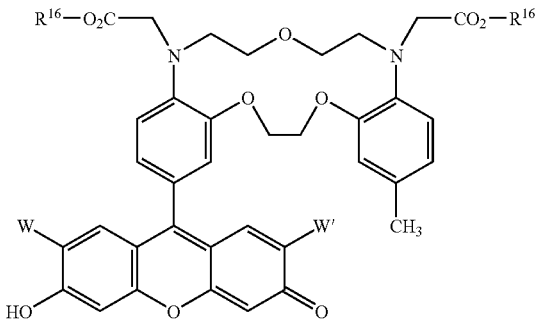

where $R^{16}$ is defined as above, and W and W' are independently F or Cl.

An additional selected embodiment of the invention has the formula

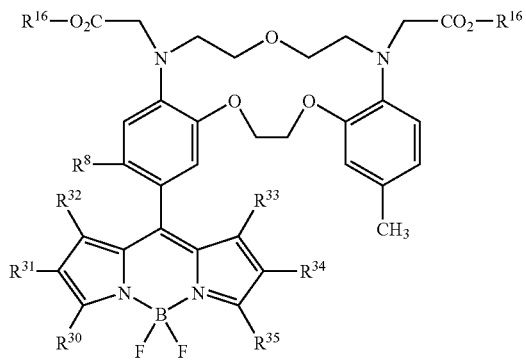

where $R^8$ and $R^{16}$ are defined as above, and $R^{30}$–$R^{35}$ are independently hydrogen, halogen, nitro, sulfo, cyano, alkyl, perfluoroalkyl, alkoxy, alkenyl, alkynyl, cycloalkyl, arylalkyl, or acyl, wherein the alkyl portions of each contain fewer than 20 carbons; or aryl or heteroaryl ring system; or adjacent substituents $R^{31}$ and $R^{32}$, and adjacent substituents $R^{33}$ and $R^{34}$, when taken in combination form a fused benzo ring that is optionally substituted one or more times by hydrogen, halogen, nitro, sulfo, cyano, alkyl, perfluoroalkyl, alkoxy, alkenyl, alkynyl, cycloalkyl, alkylthio, alkylamido, amino, monoalkylamino or dialkylamino wherein the alkyl portions of each contain fewer than 20 carbons.

In another aspect of the invention, the crown ether chelate compounds are fluorescent indicators represeted by the following structure:

Formula (II)(a and b)

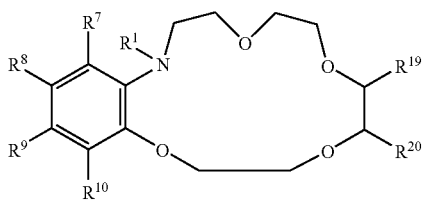

wherein Y, P and Q are oxygen and $R^9$ or $R^8$ is represented by a -L-DYE. Preferably $R^9$ is -L-DYE wherein the linker is typically a single covalent bond and the DYE moiety is selected from the group consisting of borapolyazaindacene, xanthene and indole. Most preferred are xanthene and indole DYE moieties.

A particuary preferred embodiment of this aspect is represent by the following formula:

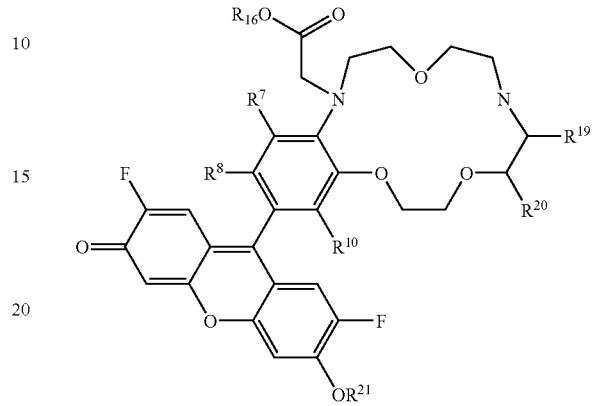

wherein $R^{16}$ is selected from the group consisting of H, $C_1$–$C_6$ alkyl, benzyl, a biologically compatible esterifying group, and a biologically compatible salt. Preferably $R^{16}$ is methyl, a biologically compatible esterifying group or a biologically compatible salt.

$R^{19}$ and $R^{20}$ are selected from the group consisting of H, halogen, azido, nitro, nitroso, amino, cyano, -L-$R_X$, -L-$S_C$, -L-DYE, $C_1$–$C_6$ alkyl and $C_1$–$C_6$ alkoxy, each of which is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$ and —(C=O)—$NR^{17}R^{18}$. Alternatively, $R^{19}$ and $R^{20}$ taken in combination form a fused six-membered benzo moiety that is optionally substituted by halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$. Typically, $R^{19}$ and $R^{20}$ are hydrogen or taken together form a fused benzo moiety.

$R^7$, $R^8$, and $R^{10}$ are independently selected from the group consisting of H, halogen, azido, nitro, nitroso, amino, cyano, -L-$R_X$, -L-$S_C$, -L-DYE, $C_1$–$C_6$ alkyl and $C_1$–$C_6$ alkoxy, each of which is optionally substituted by halogen, amino, hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$. Alternatively, $R^7$ taken in combination with $R^8$ form a fused six-membered benzo moiety, which is optionally substituted by halogen, azido, nitro, nitroso, amino, cyano, -L-$R_X$, -L-$S_C$, -L-DYE, $C_1$–$C_6$ alkyl or $C_1$–$C_6$ alkoxy, each of which is optionally substituted by halogen, amino, hydroxy, —(C=O)—$R^{15}$, —(C=O)—O—$R^{16}$, or —(C=O)—$NR^{17}R^{18}$. Typically, $R^7$, $R^8$ and $R^{10}$ are hydrogen.

$R^{21}$ is selected from the group consisting of H, $C_1$–$C_{18}$ alkyl, $C_7$–$C_{18}$ arylalkyl and lipophilic group each alkyl is optionally substituted by —(C=O)—$R^{15}$, —(C=O)—O—$R^{16}$, or $C_1$–$C_6$ alkoxy.

A particularly preferred embodiment is compound 86 and 115 and the corresponding cell-permeant versions, compounds 87 and 116 (See, Examples 79, 80, 105 and 106).

In another aspect of the invention, the crown ether chelate compounds are represented by the formula:

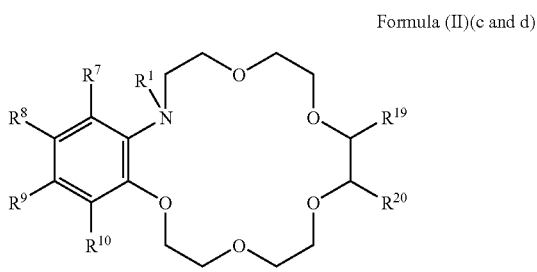

Formula (II)(c and d)

wherein $R^9$ or $R^8$ are -L-DYE, preferably $R^9$ is -L-DYE wherein L is typically a single covalent bond and the DYE moiety is borapolyazaindacene, xanthene or indole. Most preferred are xanthene and indole DYE moieties. Y, P and Q are oxygen. $E^2$ and $E^3$ are —$(CH_2)_2$— and $E^1$ is —$(CH_2)O(CH_2)$—.

A preferred embodiment is represented by compound 109 and the cell-permeant version; compound 110 (See, Examples 99 and 100).

In another aspect of the invention, the crown ether chelate compounds are represented by the formula:

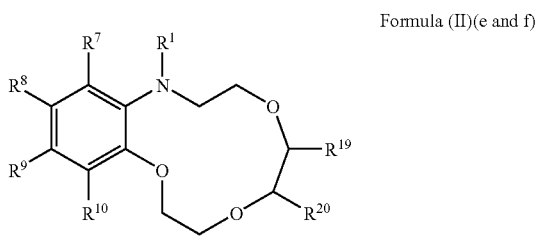

Formula (II)(e and f)

wherein $R^9$ or $R^8$ are -L-DYE, preferably $R^9$ is -L-DYE, wherein L is typically a single covalent bond and the DYE moiety is borapolyazaindacene, xanthene or indole. Most preferred is a xanthene DYE moiety. P and Q are oxygen and Y is absent. $E^1$ and $E^3$ are —$(CH_2)_2$— and $E^2$ is absent.

Typically $R^7$, $R^8$ or $R^9$, $R^{10}$, $R^{19}$ and $R^{20}$ are hydrogen and $R^1$ is a methyl or ethyl group that is substituted by —(C=O)—$R^{15}$ or —(C=O)—O—$R^{16}$ wherien $R^{15}$ and $R^{16}$ are methyl or ethyl.

A preferred embodiment is represented by compound 104 (See, Example 94).

The family of crown ether chelate compounds represented by Formula (II) are paticularly useful for binding physiological relevant levels of metal ions in vivo wherein the DYE moiety is substituted by an AM or acetate ester. In addition, this family of compounds unexeptedly cross live cell membranes easier that compounds represented by Formula (I) and are thus preferred for binding of target metal ions in live cells. Furthermore, compounds represented by Formula (II), wherein the second nitrogen atom has been replaced by an oxygen atom, unexeptedly resulted in a higher affinity binding of target metal ions such as sodium ions. This, in combination with their ability to effectively load into live cells, provides for unexpected advantages over compounds represented by Formula (I) for in vivo binding of target ions.

The family of crown ether chelate compounds represented by Formula (II) are also very useful for the binding and detection of target metal ions in vitro (See, Table 2). These compounds demonstrate a significant change in fluorescent signal after binding the target metal ions.

Selected embodiments of the invention are given in Table 1, showing a variety of distinct DYE moieties and crown ether substituents useful in the invention.

TABLE 1

Selected embodiments of the invention for Formula (I) compounds.

| Compound | Dissociation Constant (target ion) |
| --- | --- |
| Compound 51 | $K_d$ (Na$^+$) = ~52 mM<br>$K_d$ (K$^+$) = ~330 mM |

TABLE 1-continued
Selected embodiments of the invention for Formula (I) compounds.
| Compound | Dissociation Constant (target ion) |
|---|---|
| 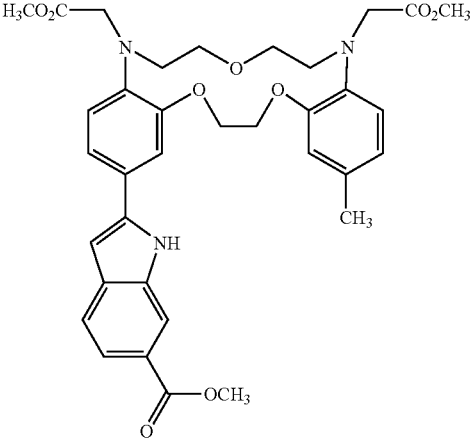<br>Compound 34 | $K_d$ (Na$^+$) = ~30 mM<br>$K_d$ (K$^+$) = ~115 nM |
| 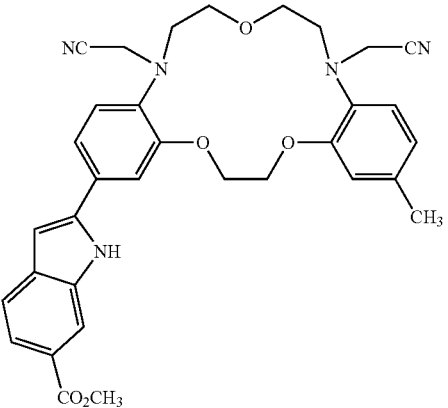<br>Compound 63 | $K_d$ (Na$^+$) = ~220 mM |
| 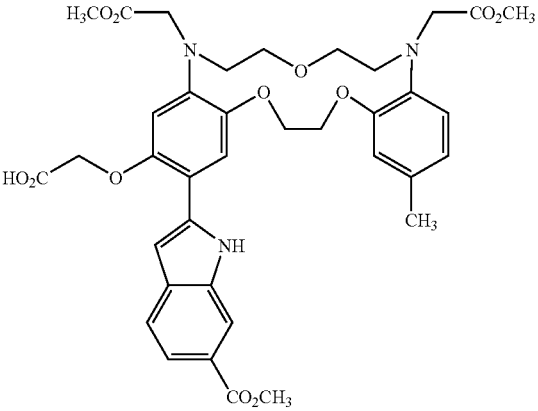<br>Compound 57 | $K_d$ (Na$^+$) = ~52 mM<br>$K_d$ (K$^+$) = ~250 mM |

TABLE 1-continued
Selected embodiments of the invention for Formula (I) compounds.
| Compound | Dissociation Constant (target ion) |
|---|---|
| 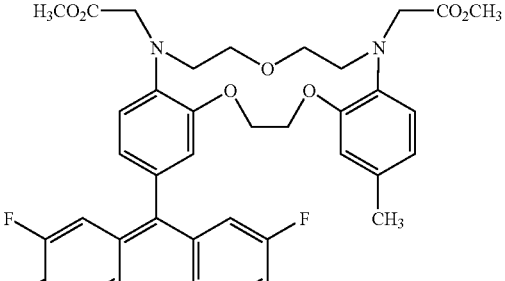\newline Compound 22 | $K_d$ (Na$^+$) = ~60 mM\newline $K_d$ (K$^+$) = ~205 mM |
| 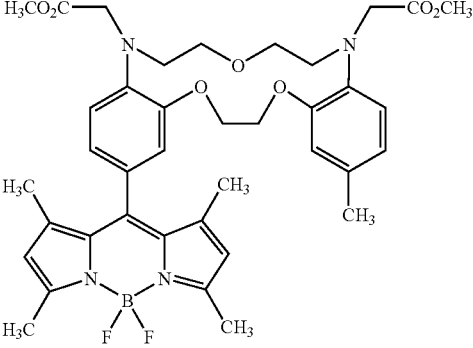\newline Compound 32 | $K_d$ (Na$^+$) = ~42 mM |
| 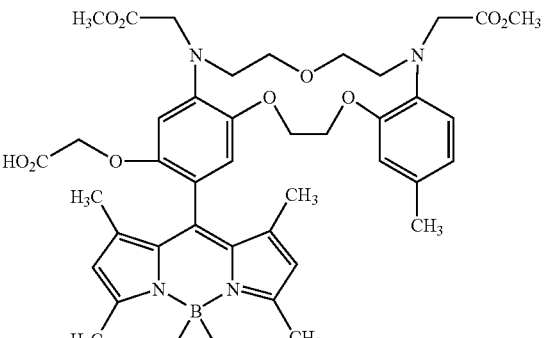\newline Compound 79 | $K_d$ (Na$^+$) = ~28 mM\newline $K_d$ (K$^+$) = ~130 mM |

TABLE 1-continued
Selected embodiments of the invention for Formula (I) compounds.
| Compound | Dissociation Constant (target ion) |
|---|---|
| Compound 27 | $K_d$ (Na$^+$) = ~95 mM<br>$K_d$ (K$^+$) = ~300 mM |
| Compound 38 | $K_d$ (Na$^+$) = ~92 mM<br>$K_d$ (K$^+$) = ~705 mM |
| Compound 60 | $K_d$ (Na$^+$) = ~70 mM<br>$K_d$ (Zn$^{2+}$) = ~100 nM |
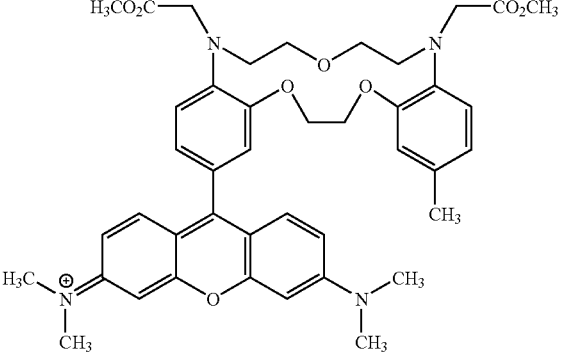

TABLE 1-continued
Selected embodiments of the invention for Formula (I) compounds.
| Compound | Dissociation Constant (target ion) |
|---|---|
| 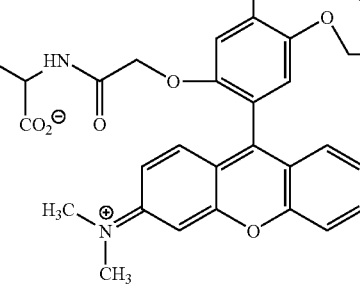  Compound 78 | $K_d$ (Na$^+$) = ~85 mM<br>$K_d$ (K$^+$) = ~255 mM |
| 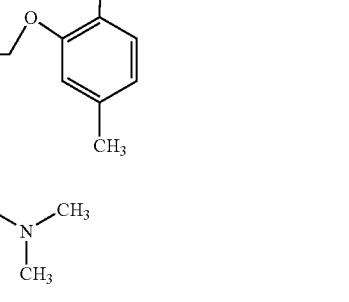  Compound 42 | $K_d$ (Na$^+$) = ~14 mM |
|   Compound 30 | $K_d$ (Na$^+$) = ~103 mM<br>$K_d$ (K$^+$) = ~205 mM |

TABLE 1-continued
Selected embodiments of the invention for Formula (I) compounds.
| Compound | Dissociation Constant (target ion) |
|---|---|
| 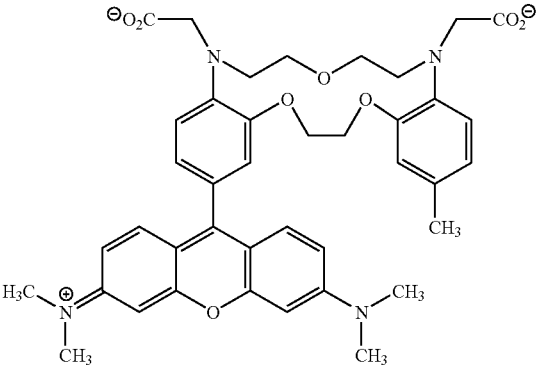Compound 28 | $K_d$ ($Zn^{2+}$) = ~300 nM<br>$K_d$ ($Ca^{2+}$) = ~4 µM<br>$K_d$ ($Na^+$) = ~38 mM<br>$K_d$ ($K^+$) = ~270 mM |
| 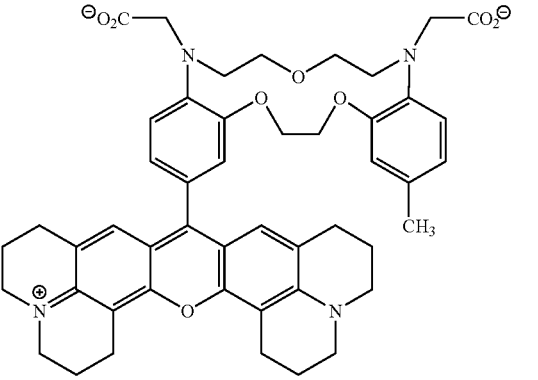Compound 31 | $K_d$ ($Zn^{2+}$) = ~8 µM<br>$K_d$ ($Ca^{2+}$) = ~7 µM |
| 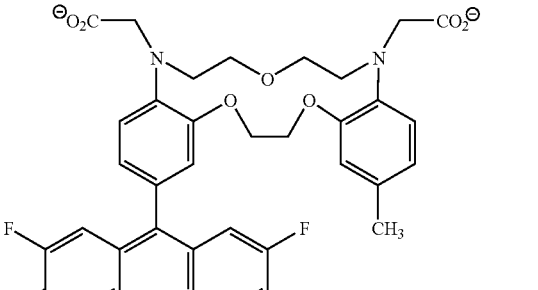Compound 23 | $K_d$ ($Na^+$) = ~36 mM<br>$K_d$ ($K^+$) = ~215 mM<br>$K_d$ ($Zn^{2+}$) = ~300 nM<br>$K_d$ ($Ca^{2+}$) = ~5 µM |

TABLE 1-continued
Selected embodiments of the invention for Formula (I) compounds.
| Compound | Dissociation Constant (target ion) |
|---|---|
| 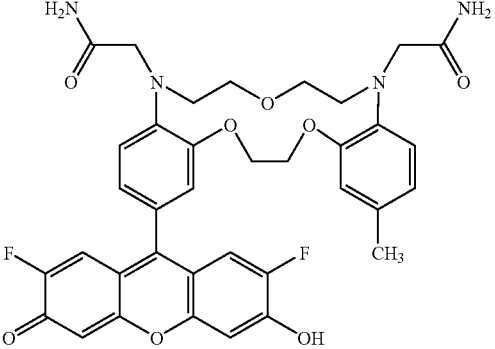 Compound 79 | $K_d$ (Na$^+$) = ~2.0 M<br>$K_d$ (Zn$^{2+}$) = ~600 μM |
| 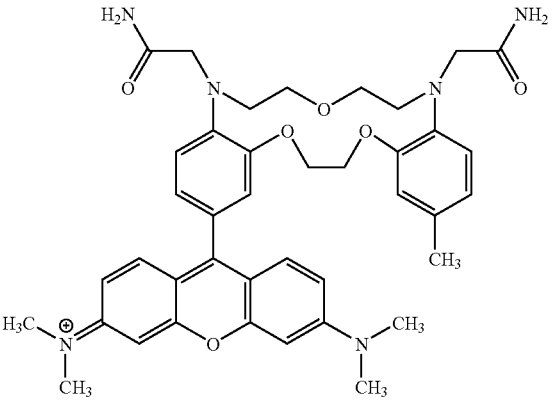 Compound 65 | $K_d$ (Na$^+$) = ~500 mM<br>$K_d$ (Zn$^{2+}$) = ~650 μM |
| 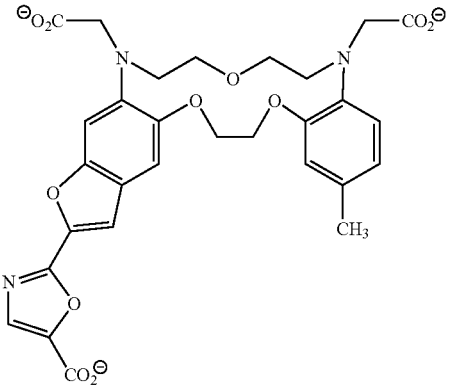 Compound 54 | $K_d$ (Ca$^{2+}$) = ~400 nM<br>$K_d$ (Na$^+$) = ~160 mM |

TABLE 1-continued

Selected embodiments of the invention for Formula (I) compounds.

| Compound | Dissociation Constant (target ion) |
|---|---|

Compound 80

Compound 81

Select preferred embodiments for in solution binding of target ions with compounds represented by Formula (II):

TABLE 2

| Compound # | Dye moiety | $R^1=$ | Dissociation constant ($K_d$) and Response to complexation (R = $F/F_0$) for Target metal ions |
|---|---|---|---|
| 104 | xanthene | —$CH_2COOCH_3$ | $K_d$ ($Li^+$) = 438 mM; R ($Li^+$) = 2.8<br>$K_d$ ($Na^+$) = 226 mM; R ($Na^+$) = 19.7<br>$K_d$ ($K^+$) = 978 mM; R ($K^+$) = 9.7<br>$K_d$ ($Rb^+$) = 376 mM; R ($Rb^+$) = 2.9 |
| 86 | xanthene | —$CH_2COOCH_3$ | $K_d$ ($Li^+$) = 142 mM; R ($Li^+$) = 6.8<br>$K_d$ ($Na^+$) = 82 mM; R ($Na^+$) = 28.5<br>$K_d$ ($K^+$) = 291 mM; R ($K^+$) = 6.9<br>$K_d$ ($Rb^+$) = 319 mM; R ($Rb^+$) = 2.7 |
| 110 | xanthene | —$CH_2COOCH_3$ | $K_d$ ($Li^+$) = no sensitivity<br>$K_d$ ($Na^+$) = 15 mM; R ($Na^+$) = 1.5<br>$K_d$ ($K^+$) = 11 mM; R ($K^+$) = 2.2<br>$K_d$ ($Rb^+$) = 25 mM; R ($Rb^+$) = 1.5 |
| 93 | indole | —$CH_2COOCH_3$ | $K_d$ ($Na^+$) = 89 mM; R ($Na^+$) = 25<br>$K_d$ ($K^+$) = no sensitivity |
| 89 | xanthene | —$CH_2COOCH_3$ | $K_d$ ($Na^+$) = 163 mM; R ($Na^+$) = 41<br>$K_d$ ($K^+$) = 254 mM; R ($K^+$) = 10.6 |
| 90 | borapolyazaindacene | —$CH_2COOCH_3$ | $K_d$ ($Na^+$) = 100 mM; R ($Na^+$) = 7.3<br>$K_d$ ($K^+$) = 170 mM; R ($K^+$) = 2.9 |
| 127 | xanthene | —$CH_2COOH$ | $K_d$ ($Na^+$) = 20 mM; R ($Na^+$) = 3.6 |

TABLE 2-continued

| Compound # | Dye moiety | $R^1=$ | Dissociation constant ($K_d$) and Response to complexation ($R = F/F_0$) for Target metal ions |
|---|---|---|---|
| 115 | xanthene | —$(CH_2)_2COCH_3$ | $K_d$ ($Na^+$) = 78.8 mM; R ($Na^+$) = 5.9 |
|   |   |   | $K_d$ ($K^+$) = 269 mM; R ($K^+$) = 2.8 |
| 118 | xanthene | —$(CH_2)_2COCH_3$ | $K_d$ ($Na^+$) = 150 mM; R ($Na^+$) = 12 |
| 120 | indole | —$(CH_2)_2COCH_3$ | $K_d$ ($Na^+$) = 89 mM; R ($Na^+$) = 2 |
| 126 | indole | —$(CH_2)_2CN(CH_3)_2$ | $K_d$ ($Na^+$) = 379 mM; R ($Na^+$) = −1.2 |
| 99 | xanthene | —$CH_2COOCH_3$ | $K_d$ ($Li^+$) = 65 mM; R ($Li^+$) = 3.1 |
|   |   |   | $K_d$ ($Na^+$) = 59 mM; R ($Na^+$) = 3.9 |
|   |   |   | $K_d$ ($K^+$) = 144 mM; R ($K^+$) = 2.7 |
|   |   |   | $K_d$ ($Rb^+$) = 157 mM; R ($Rb^+$) = 1.9 |

4. Reactive Functional Groups and Conjugated Substances of the Crown Ether Chelate Compounds.

As described above, the compounds of the invention may be substituted one or more times by a-L-$R_X$ moiety or -L-$S_C$ moiety. L is a covalent linkage that is a single covalent bond or a seris of stable bonds comprising 1–20 nohydrogen atoms selected from the group consisting of C, O, N, P and S. $R_X$ is a reactive group that functions as the site of attachment for another moiety wherein the reactive group chemically reacts with an appropriate reactive or functional group on another substance or moiety. These reactive groups are synthesized during the formation of the present compounds providing present crown ether chelate compounds that can be covalently attached to another substance, conjugated substance, facilitated by the reactive group. In this way, compounds incorporating a reactive group ($R_X$) can be covalently attached to a wide variety of biomolecules or non-biomolecules that contain or are modified to contain functional groups with suitable reactivity, resulting in chemical attachment of the conjugated substance ($S_C$), represented by -L-$S_C$. The reactive group and functional group are typically an electrophile and a nucleophile that can generate a covalent linkage. Alternatively, the reactive group is a photoactivatable group, and becomes chemically reactive only after illumination with light of an appropriate wavelength. Typically, the conjugation reaction between the reactive group and the substance to be conjugated results in one or more atoms of the reactive group $R_X$ to be incorporated into a new linkage attaching the compound of the invention to the conjugated substance $S_c$. Selected examples of functional groups and linkages are shown in Table 3, where the reaction of an electrophilic group and a nucleophilic group yields a covalent linkage.

TABLE 3

Examples of some routes to useful covalent linkages

| Electrophilic Group | Nucleophilic Group | Resulting Covalent Linkage |
|---|---|---|
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |

TABLE 3-continued

Examples of some routes to useful covalent linkages

| Electrophilic Group | Nucleophilic Group | Resulting Covalent Linkage |
|---|---|---|
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COΩ, where Ω is a good leaving group (e.g., succinimidyloxy (—$OC_4H_4O_2$) sulfosuccinimidyloxy (—$OC_4H_3O_2$—$SO_3H$), -1-oxybenzotriazolyl (—$OC_6H_4N_3$); or an aryloxy group or aryloxy substituted one or more times by electron withdrawing substituents such as nitro, fluoro, chloro, cyano, ortrifluoromethyl, or combinations thereof, used to form activated aryl esters; or a carboxylic acid activated by a carbodiimide to form an anhydride or mixed anhydride —$OCOR^a$ or —$OCNR^aNHR^b$, where $R^a$ and $R^b$, which may be the same or different, are $C_1$–$C_6$ alkyl, $C_1$–$C_6$ perfluoroalkyl, or $C_1$–$C_6$ alkoxy; or cyclohexyl, 3-dimethylaminopropyl, or N-morpholinoethyl).
**Acyl azides can also rearrange to isocyanates Choice of the reactive group used to attach the compound of the invention to the substance to be conjugated typically depends on the reactive or functional group on the substance to be conjugated and the type or length of covalent linkage desired. The types of functional groups typically present on the organic or inorganic substances (biomolecule or non-biomolecule) include, but are not limited to, amines, amides, thiols, alcohols, phenols, aldehydes, ketones, phosphates, imidazoles, hydrazines, hydroxylamines, disubstituted amines, halides, epoxides, silyl halides, carboxylate esters, sulfonate esters, purines, pyrimidines, carboxylic acids, olefinic bonds, or a combination of these groups. A single type of reactive site may be available on the substance (typical for polysaccharides or silica), or a variety of sites may occur (e.g., amines, thiols, alcohols, phenols), as is typical for proteins. A conjugated substance may be conjugated to more than one crown ether chelate compound, which may be the same or different, or to a substance that is additionally modified by a hapten, such as biotin. Although some selectivity can be obtained by careful control of the reaction conditions, selectivity of labeling is best obtained by selection of an appropriate reactive functional group.

Typically, $R_X$ will react with an amine, an alcohol, an aldehyde, a ketone, or with silica. Preferably $R_X$ reacts with an amine or a thiol functional group, or with silica. In one embodiment, $R_X$ is an acrylamide, an activated ester of a carboxylic acid, an acyl azide, an acyl nitrile, an aldehyde, an alkyl halide, a silyl halide, an anhydride, an aniline, an aryl halide, an azide, an aziridine, a boronate, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, or a thiol group. By "reactive platinum complex" is particularly meant chemically reactive platinum complexes such as described in U.S. Pat. No. 5,714,327.

Where $R_X$ is an activated ester of a carboxylic acid, the resulting compound is particularly useful for preparing conjugates of proteins, nucleotides, oligonucleotides, or haptens. Where $R_X$ is a maleimide or haloacetamide the resulting compound is particularly useful for conjugation to thiol-containing substances. Where $R_X$ is a hydrazide, the resulting compound is particularly useful for conjugation to periodate-oxidized carbohydrates and glycoproteins, and in addition is an aldehyde-fixable polar tracer for cell microinjection. Where $R_X$ is a silyl halide, the resulting compound is particularly useful for conjugation to silica surfaces, particularly where the silica surface is incorporated into a fiber optic probe subsequently used for remote ion detection or quantitation.

Preferably, $R_X$ is a succinimidyl ester of a carboxylic acid, a haloacetamide, a hydrazine, an isothiocyanate, a maleimide group, an aliphatic amine, a silyl halide, or a psoralen. More preferably, $R_X$ is a succinimidyl ester of a carboxylic acid, a maleimide, an iodoacetamide, or a silyl halide. In a particular embodiment $R_X$ is a silyl halide or an isothiocyanate.

The compounds of the invention that possess a reactive functional group are useful for conjugation to any substance that possesses a suitable functional group for covalent attachment of the chelate. Examples of particularly useful conjugates include, among others, conjugates of antigens, steroids, vitamins, drugs, haptens, metabolites, toxins, environmental pollutants, amino acids, peptides, proteins, nucleic acids, nucleic acid polymers, carbohydrates, lipids, and non-biological polymers. Alternatively, these are conjugates of cells, cellular systems, cellular fragments, or subcellular particles. Examples include, among others, virus particles, bacterial particles, virus components, biological cells (such as animal cells, plant cells, bacteria, yeast, or protists), or cellular components.

Preferably the conjugated substance is a protein, polysaccharide, lipid, lipid assembly, non-biological polymer, or polymeric microparticle. Another class of preferred conjugated substances includes particles or fibers composed of silica or other glasses, useful for preparing optical devices for remote sensing.

Preferred nucleic acid polymer conjugates are labeled, single- or multi-stranded, natural or synthetic DNA or RNA, DNA or RNA oligonucleotides, or DNA/RNA hybrids, or incorporate an unusual linker such as morpholine derivatized phosphates (AntiVirals, Inc., Corvallis Oreg.), or peptide nucleic acids such as N-(2-aminoethyl)glycine units.

In a preferred embodiment, the conjugated substance ($S_c$) is a carbohydrate that is typically a polysaccharide, such as a dextran, FICOLL, heparin, glycogen, amylopectin, mannan, inulin, starch, agarose and cellulose. Alternatively, the carbohydrate is a polysaccharide that is a lipopolysaccharide. Preferred polysaccharide conjugates are dextran, FICOLL, or lipopolysaccharide conjugates.

In another embodiment, the conjugated substance ($S_c$), is a lipid moiety (typically having 6–60 carbons), including glycolipids, phospholipids, sphingolipids, and steroids. Alternatively, the conjugated substance is a lipid assembly, such as a liposome. The lipid moiety may be used to retain the conjugated substances in cells, as described in U.S. Pat. No. 5,208,148.

Other conjugates of non-biological materials include conjugates of organic or inorganic polymers, polymeric films, polymeric wafers, polymeric membranes, polymeric particles, or polymeric microparticles, including magnetic and non-magnetic microspheres, conducting and non-conducting metals and non-metals, and glass and plastic surfaces and particles. Conjugates are optionally prepared by copolymerization of a compound of the invention that contains an appropriate functionality while preparing the polymer, or by chemical modification of a polymer that contains functional groups with suitable chemical reactivity. Other types of reactions that are useful for preparing conjugates of polymers include catalyzed polymerizations or copolymerizations of alkenes and reactions of dienes with dienophiles, transesterifications or transaminations. In another embodiment, the conjugated substance is a glass or silica, which may be formed into an optical fiber or other structure.

Conjugates typically result from mixing appropriate reactive dyes and the substance to be conjugated in a suitable solvent in which both are soluble. Labeling of insoluble polymers or silica can be performed in a suspension of the insoluble polymer in a suitable solvent. For those reactive groups that are photoactivated, conjugation requires illumination of the reaction mixture to activate the reactive group.

Synthesis

There are typically three components to the methodology used to prepare the compounds of the invention. The first involves the formation of the crown ether chelate itself, the second involves the appropriate derivatization of the secondary amine nitrogen atom(s) of the crown ether chelate, and the third, when needed, involves modification of the crown ether chelate by forming a reactive functional group, covalently attaching a conjugate, or covalently attaching a DYE moiety to form an indicator. It should be understood that the DYE moiety is typically not attached to the crown ether chelate compound but that the conjugated substance is attached in this way. Although these synthetic components are typically performed in the order given, they may be carried out in any other suitable sequence. For example, a portion of the chelate may be derivatized with a fluorescent dye prior to formation of the complete chelate ring.

Where the P and Q moieties are both oxygen, and $E^1$ is ethylene, the crown ether chelate is typically prepared by acylation of a bis-(2-aminophenoxy)ethane with a bis-(acid chloride), such as diglycolyl chloride, followed by reduction of the resulting bis-amide to the corresponding bis-secondary amine. Selection of the appropriate bis-acid chloride results in the particular desired crown ether (as in Examples 64–69 and 70).

The secondary amine nitrogen atom(s) present in the crown ether are typically derivatized with an alkylating agent. As the metal binding ability of the resulting crown ether is significantly influenced by the nature of the amine substituents, careful selection of the alkylating agent may be necessary to prepare a reporter for a particular target ion. Where the crown nitrogens are alkylated by methyl bromoacetate, the resulting bis-aza-crown ether is typically selective for sodium ions. If the alkylating agent is 2-picolyl chloride, the resulting crown ether is typically selective for zinc ions. As discussed above, the presence of esters vs. carboxylic acids on the amine nitrogen substituents may influence the relative binding affinity of selected target ions. Selection of an alkylating agent that incorporates a precursor to a reactive functional group is useful for producing chemically reactive compounds of the invention, as well as acting as a useful intermediate for preparing conjugates, as described above. Additionally, an alkylating agent that incorporates a reporter DYE results in a crown ether compound that functions as an indicator for selected target ions.

More typically, the crown ether chelate is derivatized at the benzo ring of the crown ether. As described above, typically a suitable crown ether is prepared, and then bound to a DYE moiety. In one aspect of the invention, an ortho-hydroxy aromatic aldehyde is treated with a chloromethyl heterocycle to yield a fused reporter (as described in Example 46). In another aspect of the invention, derivatization with a DYE moiety is carried out by modifying a crown ether that possesses an aldehyde or ketone functional group.

In one aspect of the invention, the crown ether is substituted by an aldehyde and the fluorophore precursors and the crown ether are combined under anaerobic or non-oxidative conditions (e.g., under nitrogen), and subsequently oxidized using a mild oxidant (e.g., a quinone oxidant, preferably DDQ or chloranil). Where xanthene fluorophore precursors are condensed under anaerobic conditions, the resulting fluorophore is the non-fluorescent dihydro species, which may be utilized without prior oxidation as a sensor for oxidative subenvironments, e.g., in cells.

In yet another aspect of the invention, the crown ether is substituted by a carboxylic acid or by an aldehyde that is converted to the carboxylic acid in the course of synthesis of the crown ether. The chelating moiety is then condensed with the fluorophore precursors to yield the resulting indicator directly.

Synthesis of conventional xanthene dyes such as fluoresceins, rhodamines and rhodols typically involve the condensation of two equivalents of resorcinol (for fluoresceins), aminophenol (for rhodamines) or a mixture of a resorcinol and an aminophenol (for rhodols) with a carbonyl-containing moiety such as a phthalic acid derivative or benzaldehyde. In the synthesis of the xanthene indicators of the invention, the desired resorcinol or aminophenol is condensed with the substituted crown ether, yielding either the reduced xanthene (where the crown ether contains an aldehyde) or the oxidized xanthene (where the crown ether contains a carboxylic acid or acyl halide) bound directly to the chelating moiety.

An oxidation step is typically required after condensation of a formyl-substituted crown ether with the fluorophore precursors. Optionally, the dihydro condensation product is isolated and subsequently oxidized with air or by standard chemical oxidants, such as chloranil. For some fluorophores, the oxidation reaction is enhanced by acidic reaction conditions. These mild oxidation reaction conditions tolerate a wide variety of substituents on the fluorophore and/or crown ether of the resulting indicators.

Unsymmetrical xanthene dyes are typically constructed by statistical methods, using a 1:1 mixture of the desired resorcinols or aminophenols in the condensation reaction, and purifying the desired product from the statistical mix of products using methods known in the art.

The synthesis of polyazaindacene dyes, particularly dipyrrometheneboron difluoride dyes, has been well documented (U.S. Pat. Nos. 4,774,339; 5,187,288; 5,248,782; 5,274,113; 5,338,854 and 5,433,896). The procedure typically consists of an acid-catalyzed condensation of a benzaldehyde with a pyrrole that has a hydrogen at the 2-position, followed by in situ oxidation of the condensed intermediate by air, oxygen or a chemical oxidant such as 2,3-dichloro-5,6-dicyano-1,4-benzoquinone (DDQ). The condensation of two appropriately substituted pyrroles, each having a hydrogen at the 2-position, with a formyl-substituted crown ether, followed by in situ oxidation of the condensed intermediate and treatment with a boron trifluoride etherate yields the dipyrrometheneboron difluoride indicators of the invention. Alternatively, the indicators are formed via the direct condensation of a carboxyl- or chlorocarbonyl-substituted crown ether with two equivalents of appropriately substituted pyrroles, which may be the same of different, provided each has a hydrogen at the 2-position. The latter procedure does not require oxidation.

Post-condensation modifications of both the crown ether and the fluorophore moiety are typically strictly analogous to known methods of indicator modification; for example, the reduction of nitro substituents to amino groups, the conversion of carboxy substituents to cyano groups, and the preparation of esters of carboxylic acids, including acetoxymethyl esters. Additionally, salts and counterions of the indicators of the invention are readily converted to other salts by treatment with ion-exchange resins, selective precipitation, and basification, as is well-known in the art.

Post-condensation modifications of xanthylium dyes are well known. For instance, the xanthenone portion of the dye can be halogenated by treatment with the appropriate halogenating agent, such as liquid bromine. Xanthenes containing unsaturated fused rings can be hydrogenated to the saturated derivatives.

The reduced and oxidized versions of the xanthene indicators are freely interconvertible by well-known oxidation or reduction reagents, including borohydrides, aluminum hydrides, hydrogen/catalyst, and dithionites. Care must be exercised to select an oxidation or reducing agent that is compatible with the crown ether chelator. A variety of oxidizing agents mediate the oxidation of dihydroxanthenes, including molecular oxygen in the presence or absence of a catalyst, nitric oxide, peroxynitrite, dichromate, triphenylcarbenium and chloranil. The dihydroxanthenes are also oxidized electrochemically, or by enzyme action, including horseradish peroxidase in combination with peroxides or by nitric oxide.

Rather than condensing the DYE moiety precursors directly with a substituted crown ether, the preformed DYE moiety may be covalently bound to the crown ether via a conventional cross-linking reaction. A wide variety of chemically reactive or potentially chemically reactive and fluorescent fluorescein, rhodamine, rhodol, benzoxanthenes, dibenzoxanthene and other xanthene oxygen heterocycles that absorb maximally beyond about 490 nm are commercially available as described by Haugland, HANDBOOK OF FLUORESCENT PROBES AND RESEARCH PRODUCTS (Supra), as described above, or in other literature references. The nature of the bond that links the DYE moiety to the crown ether chelate appears to have an effect on the optical response of the DYE moiety to ion binding, sometimes a significant effect. Acceptability of the linking chemistry can be determined by titration of the resultant indicator with the ion of interest over the target range of response (as described in Example 71).

B. Method of Use

The crown ether compounds of the invention are useful for any application where it is desirable to complex a target metal ion. Selected crown ether compounds of the invention may be useful as ionophores, that is, they facilitate the transport of selected target ions across cell membranes. Where the crown ether compound is bound to a conjugated substance that is a polymeric matrix, such as a microparticle, or agarose, the compounds are useful for depleting a sample solution of a selected target ion, particularly where the polymeric matrix is used to pack a chromatography column. Other crown ether compounds (those bound to a DYE moiety) are useful as colorimetric or fluorescent indicators for a selected target ion.

In order for a particular indicator of the present invention to be useful for detection purposes, it must exhibit a detectable change in spectral properties upon complexation of the desired metal ion (target ion) in the chelating moiety. Preferably the change in spectral properties is a change in fluorescence properties. More preferably, the instant indicators display an intensity increase or decrease in emission energy upon the complexation of the desired target ion.

However, it should be appreciated that at least the compounds represented by Formula (II) do not require a DYE moiety. These compounds are useful for binding target ions resulting in a complex of the target ion and the present crown ether chelate compounds. Therefore, an additional aspect of the invention includes the compound of the invention further comprising a metal ion that is associated and/or complexed within the crown ether chelate portion of the compound. The metal ion is optionally a monocation (such as $Li^+$, $Na^+$, $K^+$, $Rb^+$, or $Cs^+$), a dication (such as $Ca^{2+}$, $Zn^{2+}$, or $Mg^{2+}$), or a polycation (such as $Tb^{3+}$ or $Eu^{3+}$). Preferably the crown ether chelate metal in complex comprises physiological relevant cations such as sodium, potassium, calcium and zinc.

Accordingly, a method for binding target metal ions in a sample comprises the following steps:
 a) contacting said sample with a crown ether chelate compound of the present invention; and,
 b) incubating said sample and said metal chelating compound for sufficient time to allow said compound to chelate said target metal ion whereby said metal ion is bound.

When the present compounds are used as indicators a DYE moiety is covalently attached to the crown ether chelate. The sample is illuminated with an appropriate wavelength whereby the target ion is detected. In such an assay the target ion can also be quantitated and monitored.

The specific indicator used in an assay or experiment is selected based on the desired affinity for the target ion as determined by the expected concentration range in the sample, the desired spectral properties, and the desired selectivity. Initially, the suitability of a material as an indicator of ion concentration is commonly tested by mixing a constant amount of the indicating reagent with a measured amount of the target ion under the expected experimental conditions.

Preferred indicators display a high selectivity, that is, they show a sufficient rejection of non-target ions. The interference of a non-target ion is tested by a comparable titration of the indicator with that ion. Although preferred target ions for most indicators of the present invention are $Na^+$ and $K^+$, any ion that yields a detectable change in absorption wavelengths, emission wavelengths, fluorescence lifetimes or other measurable optical property over the concentration range of interest is potentially measured using one of the indicators of this invention. Modifications to the electronic structure of the crown ether or indicator to produce an indicator having the appropriate combination of binding affinity, ion selectivity and spectral response for a wide variety of metal ions.

In one embodiment of the invention, the target ions for the indicators of the present invention are selected from $Li^+$, $Na^+$, $K^+$, $Cs^+$, $Ca^{2+}$, $Zn^{2+}$, $Mg^{2+}$, $Rb^+$, $Tb^{3+}$ or $Eu^{3+}$. In another embodiment of the invention, the target ions are selected from $Li^+$, $Na^+$, $K^+$, $Ca^{2+}$, $Zn^{2+}$, and $Mg^{2+}$. Additional target ions for selected embodiments of the present indicators also include $Mn^{2+}$, $Fe^{2+}$, $Fe^{3+}$, $Co^{2+}$, $Ni^{2+}$, $Cu^{2+}$, $Cu^+$, $Zn^{2+}$, $Al^{3+}$, $Cd^{2+}$, $Ag^+$, $Au^+$, $Tl^+$, $Pd^{2+}$, $Hg^{2+}$, $Hg^+$, $Sn^+$, $Pb^{2+}$, $Sr^{2+}$, $Ba^{2+}$, $Mo^{3+}$, $Ga^{3+}$, $In^{3+}$, $La^{3+}$, $Eu^{3+}$, $Tb^{3+}$, $Dy^{3+}$, $Ru^{3+}$, $Sc^{3+}$, $As^{3+}$, $Sb^{3+}$, $Cr^{3+}$, $Bi^{3+}$, $Ce^{3+}$, $Ce^{4+}$, $Pd^{2+}$, $Pt^{2+}$ and $Pt^{4+}$ ions. In yet another embodiment of the invention, the target ions of the instant indicators are $Fe^{2+}$, $Fe^{3+}$, $Co^{2+}$, $Ni^{2+}$, $Cu^{2+}$, $Cu^+$, $Zn^{2+}$, $Al^{3+}$, $Cd^{2+}$, $Hg^{2+}$, $Pb^{2+}$, $Ba^{2+}$, $La^{3+}$, $Tb^{3+}$ and $Cr^{3+}$ ions. In yet another embodiment, the target ions are selected from the group consisting of $Fe^{3+}$, $Ni^{2+}$, $Cu^{2+}$, $Cu^+$, $Hg^{2+}$, or $Pb^{2+}$.

The indicator is generally prepared for use as a detection reagent by dissolving the indicator in solution at a concentration that is optimal for detection of the indicator at the expected concentration of the target ion. Modifications that are designed to enhance permeability of the indicator through the membranes of living cells, such as acetoxymethyl esters and acetates, may require the indicator to be predissolved in an organic solvent such as dimethylsulfoxide (DMSO) before addition to a cell suspension, where the indicators then readily enter the cells. Intracellular enzymes cleave the esters to the more polar acids and phenols that are then well retained inside the cells. For applications where permeability of cell-membranes is required, the indicators of the invention are typically substituted by only one fluorophore.

Therefore, a method for binding and detecting target ions in a live cell comprises the following steps:
 a) contacting a sample of live cells with a crown ether chelate compound of the present invention wherein said compound comprises a DYE moiety and at least one lipophilic group;
 b) incubating said sample and said crown ether chelate compound for sufficient time to allow said compound to chelate said target metal ion; and,
 c) illuminate said sample with an appropriate wavelength whereby said target ion is detected in a live cell.

Typically, the lipophilic group is an AM or acetate ester that is directly attached to the DYE moiety of the crown ether chelate compound.

A specific indicator of the present invention is useful for the detection and/or quantification of a desired target ion, when the binding of the target ion in the metal ion-binding moiety of the indicator results in a detectable change in spectral properties. Preferably, the change in spectral properties is a detectable fluorescence response.

A preferred indicator for a specific target ion is an indicator that shows at least a two-fold change in net fluorescence emission intensity (either higher or lower), or a 1 nanosecond difference in fluorescence lifetime (either shorter or longer), preferably a five-fold or greater change in net fluorescence emission intensity or a 100% change in fluorescence lifetime in response to the target ion. Alternatively, an indicator that exhibits a shift in excitation or emission wavelength of at least 10 nm (either to shorter or longer wavelength) is also preferred, more preferably exhibiting a shift of 25 nm or greater.

The optical response of the indicating reagent is determined by changes in absorbance or fluorescence, preferably fluorescence. If absorbance measurements are used to determine ion concentrations, then it is usually optimal to adjust the optical density of the indicator in the sample over the range of analyte concentration to a value of approximately 0.02 to 2.5 (most preferably 0.1 to 1). For fluorescence measurements, the concentration of the indicator will depend mostly on the sensitivity of the equipment used for its detection.

If the optical response of the indicator will be determined using fluorescence measurements, samples are typically stained with indicator concentrations of $10^{-9}$ M to $10^{-2}$ M. The most useful range of analyte concentration is about one log unit above and below the dissociation constant of the ion-indicator complex. This dissociation constant is determined by titration of the indicator with a known concentration of the target ion, usually over the range of virtually zero concentration to approximately 100 millimolar of the target ion, depending on which ion is to be measured and which indicator is being used. The dissociation constant may be affected by the presence of other ions, particularly ions that have similar ionic radii and charge. It may also be affected by other conditions such as ionic strength, pH, temperature, viscosity, presence of organic solvents and incorporation of the sensor in a membrane or polymeric matrix, or conjugation or binding of the sensor to a protein or other biological molecule. Any or all of these effects need to be taken into account when calibrating an indicator.

The indicator is combined with a sample in a way that will facilitate detection of the target ion concentration in the sample. The sample is generally a representative cell population, fluid or liquid suspension that is known or suspected to contain the target ion. Representative samples include intracellular fluids such as in blood cells, cultured cells, muscle tissue, neurons and the like; extracellular fluids in areas immediately outside of cells; in vesicles; in vascular tissue of plants and animals; in biological fluids such as blood, saliva, and urine; in biological fermentation media; in environmental samples such as water, soil, waste water and sea water; in industrial samples such as pharmaceuticals, foodstuffs and beverages; and in chemical reactors. Detection and quantitation of the target ion in a sample can help characterize the identity of an unknown sample, or facilitate quality control of a sample of known origin.

In one embodiment of the invention, the sample contains cells, and the indicator is combined with the sample in such a way that the indicator is present within the sample cells. By selection of the appropriate chelating moiety, fluorophore, and the substituents thereon, indicators are prepared that will selectively localize in desired organelles, and provide measurements of the target ion in those organelles. Conjugates of the indicators of the invention with organelle-targeting peptides are used to localize the indicator to the selected organelle, facilitating measurement of target ion presence or concentration within the organelle (as described in U.S. Pat. No. 5,773,227). Alternatively, selection of a lipophilic fluorophore, or a fluorophore having predominantly lipophilic substituents will result in localization in lipophilic environments in the cell, such as cell membranes. Selection of cationic indicators will typically result in localization of the indicator in mitochondria.

In another aspect of the invention, a composition of matter comprises any of the compounds described above, and optionally includes a metal ion. In one embodiment, the compounds of the invention, in any of the embodiments described above, are associated, either covalently or noncovalently, with a surface such as a microfluidic chip, a silicon chip, a microscope slide, a microplate well, or another solid matrix, and is combined with the sample of interest as it flows over the surface. The detectable optical response is therefore detected on the matrix surface itself, typically by use of an instrumental. This embodiment of the invention is particularly suited to high-throughput screening using automated methods.

Quantification of target ion levels in samples is typically accomplished using the indicators of the present invention by methods known in the art. For example, the ratiometric measurement of ion concentration provides accurate measurement of ion concentrations by the treatment of the fluorescence data as the ratio of excitation or fluorescence intensities at two wavelengths, rather than the absolute intensity at a single wavelength. Using the ratio method, a number of variables that may perturb the ion concentration measurements are eliminated. In particular, ion-dependent factors that affect the signal intensity, such as nonuniform intracellular dye concentrations, probe leakage, dye bleaching and cell thickness, are canceled in the ratio measurements, since these parameters have a similar effect on intensities at both wavelengths. While the ratio method can be used to determine concentrations using observation of either the excitation spectra of the indicator, the emission spectra of the indicator, or both, in the case of the indicators of the present invention, the shift in excitation energy upon binding metal ions makes observation of the excitation spectrum a more useful technique. In either case, to achieve maximal utility, the indicator must be calibrated (to compensate for variance in the dissociation constant of the indicator due to ionic strength, viscosity, or other conditions within the sample). To calibrate the indicator, ionophores such as A-23187, gramicidin, valinomycin, or ionomycin are used. Non-ratiometric analysis can also be accomplished by calibration with a second fluorescent dye present in the sample.

The optical response of the indicator to the ion can be detected by various means that include measuring absorbance or fluorescence changes with an instrument, visually, or by use of a fluorescence sensing device. Several examples of fluorescence sensing devices are known, such as fluorometers, fluorescence microscopes, laser scanners, flow cytometers, and microfluidic devices, as well as by cameras and other imaging equipment. These measurements may be made remotely by incorporation of the fluorescent ion sensor as part of a fiber optic probe. The indicator is covalently attached to the fiber optic probe material, typically glass or functionalized glass (e.g., aminopropyl glass) or the indicator is attached to the fiber optic probe via an intermediate polymer, such as polyacrylamide. The indicator solution is alternatively incorporated non-covalently within a fiber optic probe, as long as there is a means whereby the target ion can come into contact with the indicator solution.

C. Kits of the Invention

Due to the advantageous properties and the simplicity of use of the instant crown ether compounds, they are particularly useful in the formulation of a kit for the complexation, detection, quantification or monitoring of selected target ions, comprising one or more compounds or compositions of the invention in any of the embodiments described above (optionally in a stock solution), instructions for the use of the crown ether compound to complex or detect a desired target ion, and optionally comprising additional components. In one aspect, the compounds of the invention are associated with a surface, such as a chip, microplate well, or other solid matrix, and the sample of interest flows over the surface. The detectable optical response is therefore detected on the matrix surface itself.

Therefore a kit of the present invention for binding a target metal ion in a sample comprises a compound represented by Formula (I) or Formula (II) and comprising one or more components selected from the group consisting of a calibration standard of a metal ion, an ionophore, a fluorescent standard, an aqueous buffer solution and an organic solvent.

The additional kit components may be selected from, without limitation, calibration standards of a target ion, ionophores, fluorescence standards, aqueous buffers, and organic solvents. The additional kit components are present as pure compositions, or as aqueous solutions that incorporate one or more additional kit components. Any or all of the kit components optionally further comprise buffers.

The examples below are given so as to illustrate the practice of this invention. They are not intended to limit or define the entire scope of this invention.

EXAMPLES

Example 1

Preparation of a Tetraaza-Crown Ether

2-Nitroaniline is acylated with diglycolyl chloride in anhydrous THF, using 0.5 equivalents of diglycolyl chloride in dilute solution. A 0.1 M THF solution of diglycolyl chloride is slowly added to a 0.1 M THF solution of 2-nitroaniline, containing two equivalents of triethylamine. After TLC indicates consumption of all starting 2-nitroaniline, volatiles are removed in vacuo and the residue is partitioned between water and ethyl acetate. The ethyl acetate layer is concentrated to give Compound 1.

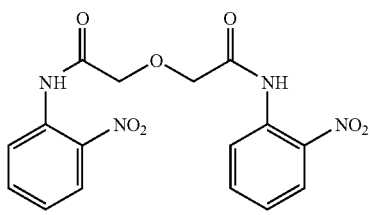

Compound 1

Compound 1 is dissolved in methanol and treated with 20% by weight of 10% palladium on carbon. The resulting mixture is shaken under 40 psi hydrogen until analysis by thin layer chromatography (TLC) indicates the reaction is complete. The reaction mixture is filtered and the bis-aniline 2 is isolated by concentration in vacuo of the filtrate.

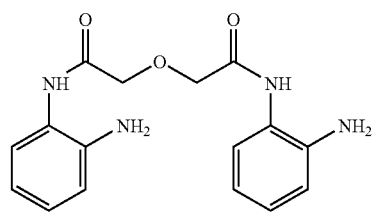

Compound 2

Compound 2 is dissolved in DMF to achieve a 0.1 M solution and then treated with 0.9 equivalents of 1,2-dibromoethane, two equivalents of diisopropylethylamine, and catalytic sodium iodide. The resulting solution is heated until most of compound 2 is consumed, as judged by TLC analysis. The volatiles are removed in vacuo, and the residue is partitioned between ethyl acetate and water. The ethyl acetate layer is concentrated in vacuo to give compound 3.

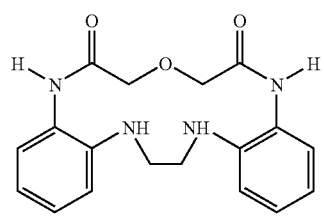

Compound 3

Compound 3 is dissolved in acetonitrile to achieve a 0.5 M concentration. Ten equivalents of formaldehyde, as a 37% aqueous solution, are added followed by 4 equivalents of sodium cyanoborohydride. The pH of the reaction mixture is adjusted to 7 with acetic acid, and the resulting solution is stirred until TLC analysis indicates consumption of compound 3 and formation of compound 4. Volatiles are removed in vacuo, and the residue is partitioned between ethyl acetate and water. The ethyl acetate layer is concentrated in vacuo to give compound 4.

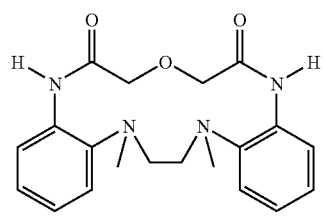

Compound 4

Compound 4 is dissolved in THF at 1 M concentration, and treated with 10 equivalents of borane-THF (1M). The resulting solution is heated at reflux until compound 4 is consumed and compound 5 is formed, as judged by TLC analysis. The reaction is quenched by addition of 5% aqueous sodium hydroxide, followed by extraction with ethyl acetate. The ethyl acetate layer is concentrated in vacuo to give compound 5.

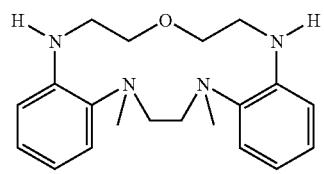

Compound 5

Compound 5 is dissolved in DMF at 0.5 M concentration. Ten equivalents of methyl bromoacetate and 4 equivalents of diisopropylethylamine are added, and the resulting solution is stirred at 100 degrees centigrade until TLC analysis indicates consumption of compound 5 and formation of compound 6. Volatiles are removed in vacuo, and the residue is partitioned between water and ethyl acetate. The ethyl acetate layer is concentrated in vacuo to give compound 6, which can be further purified by flash chromatography on silica gel using methanol in chloroform as eluant.

Compound 6

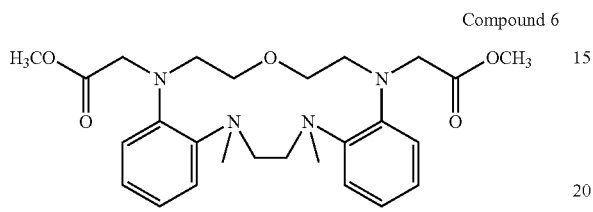

Example 2

Preparation of (2'-Nitrophenoxy)-2-chloroethane (7)

A suspension of 2-nitrophenol (50.0 g, 0.36 mol), 1-bromo-2-chloroethane (45 mL, 0.54 mol), and $K_2CO_3$ (100.0 g, 0.72 mol) in DMF (200 mL) was stirred at 90° C. for 2 h, cooled to room temperature, poured into ice-water, filtered, washed with $H_2O$ and dried to give Compound 7, 70.3 g (96%) as a yellow solid.

Compound 7

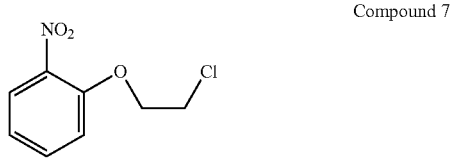

Example 3

Preparation of 1-(5'-methyl-2'-nitrophenoxy)-2-(2"-nitrophenoxy)ethane (8)

A suspension of Compound 7 (60.45 g, 0.30 mol), 5-methyl-2-nitrophenol (50.49 g, 0.33 mol), and $K_2CO_3$ (82.80 g, 0.60 mol) in DMF (450 mL) was stirred at 130° C. for 18 h, cooled to room temperature, poured into ice-water, filtered, washed with $H_2O$ and dried to give Compound 8, 89.50 g (93.5%) as an orange solid.

Compound 8

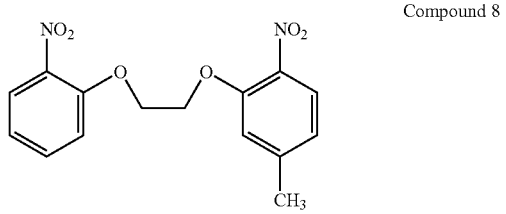

Example 4

Preparation of 1-(2'-amino-5'-methylphenoxy)-2-(2"-aminophenoxy)ethane (9)

Compound 8 (24.0 g, 75 mmol) was hydrogenated over 10% Pd/C (1.5 g) in DMF (250 mL) at 40 psi for 18 h. The mixture was filtered from catalyst through a CELITE pad on a fritted glass filter. The filtrate was evaporated and ether (50 mL) was added. The product was filtered, washed with ether and dried to give compound 9, 18.0 g (95%) as a brown solid.

Compound 9

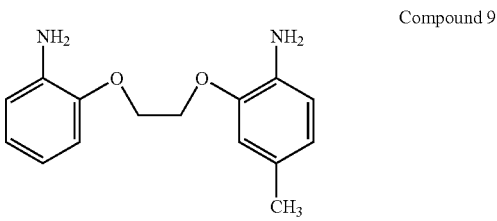

Example 5

Preparation of Compound 10

To a stirred mixture of diamine Compound 9 (13.10 g, 50 mmol) and $Et_3N$ (20.8 mL, 150 mmol) in dry THF (2.5 L) was slowly added over 12 h a solution of diglycolyl dichloride (6.3 mL, 55 mmol) in dry THF (0.5 L). The reaction mixture was stirred for 6 h, filtered from the precipitated hydrochloride, and washed with THF. The combined organic filtrate was evaporated. The residue was dissolved in $CHCl_3$ (800 mL) and washed successively with 0.5 M HCl, $H_2O$, saturated $NaHCO_3$ then saturated NaCl. The organic layer was dried over $MgSO_4$ and evaporated. Ether (100 mL) was added and the precipitated product was filtered, washed with ether and dried to give Compound 10, 16.0 g (90%) as an off-white solid.

Compound 10

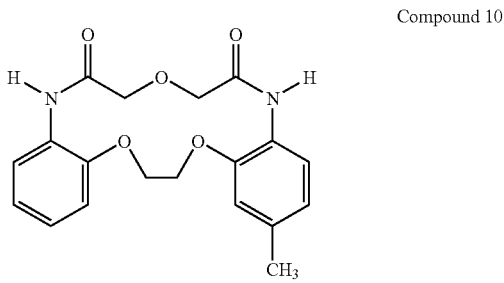

Example 6

Preparation of Compound 11

To a suspension of diamide Compound 10 (15.60 g, 44 mmol) in dry THF (400 mL) was added a 1 M solution of $BH_3$-THF complex in dry THF (390 mL, 390 mmol). The mixture was stirred at 70° C. for 16 h. Dry methanol (300 mL) was added dropwise over 1 h into a boiling mixture with strong gas evaluation. The mixture was heated at reflux for 2 h, cooled to room temperature, evaporated and co-evaporated with MeOH to destroy the borane complex. Ether (100 mL) was added. The solid product was filtered, washed with ether and dried to give Compound 11, 12.3 g (85%) as an off-white solid.

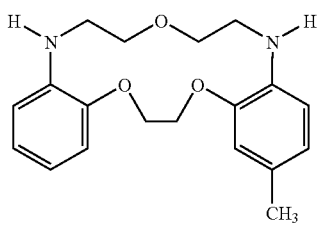

Compound 11

Example 7

Preparation of Compound 12

A mixture of diamine 11 (6.56 g, 20 mmol), methyl bromoacetate (38 mL, 400 mmol), diisopropylethylamine (DIPEA) (104 mL, 600 mmol), and NaI (1.50 g, 10 mmol) in MeCN (300 mL) was heated at reflux for 70 h. After cooling to room temperature, the MeCN was evaporated. The residue was dissolved in CHCl₃, washed with 1% AcOH then H₂O, dried and evaporated. The residual oily product was cooled to 0° C. and washed with cold hexane to remove most of the alkylating reagent. The crude product, compound 12, was used immediately in the next step without further purification.

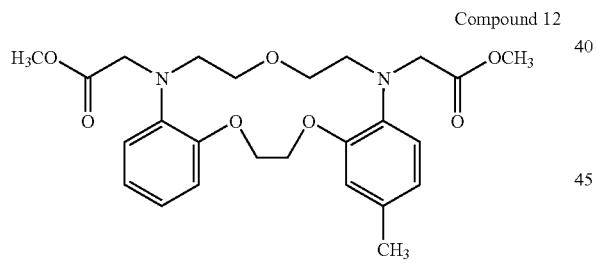

Compound 12

Example 8

Preparation of Compound 13

To a stirred solution of the Vilsmeier reagent prepared from POCl₃ (4.65 mL, 50 mmol) and 30 mL DMF was added over 5 min a solution of Compound 12 (4.8 g, 10 mmol) in DMF (20 mL). The mixture was stirred for 16 h, cooled by the addition of ice and neutralized with saturated $K_2CO_3$ to pH 7–8. The suspension was extracted with CHCl₃, washed successively with 0.1 M HCl, saturated NaCl, saturated NaHCO₃ and saturated NaCl and then evaporated. The residue was dissolved in CHCl₃ and chromatographed on SiO₂ with an EtOAc gradient in hexanes (20% to 30%) to give aldehyde 13, 2.60 g (52%) as colorless crystals.

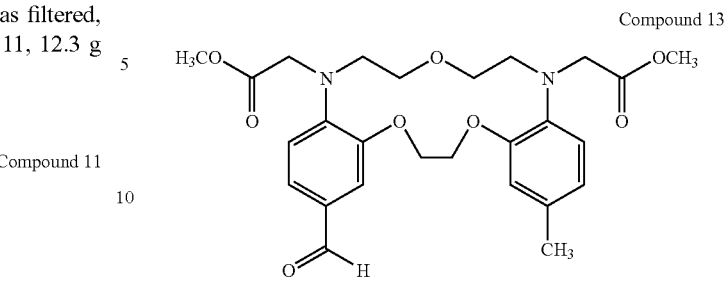

Compound 13

Example 9

Preparation of Compound 14

Compound 14 was prepared analogously with Compound 13, starting with 5-methyl-2-nitrophenol in place of 2-nitrophenol, and utilizing 4-benzyloxy-2-nitrophenol in place of 5-methyl-2-nitrophenol.

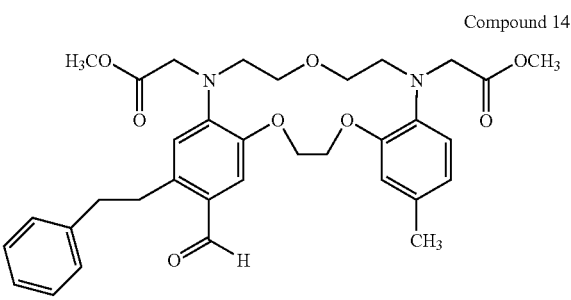

Compound 14

Example 10

Preparation of Compound 15

Compound 14 (3.06 g, 5.0 mmol) was hydrogenated over 10% Pd/C (0.50 g) in AcOH (100 mL) at 50 psi for 5 h. The mixture was filtered through a CELITE pad on a fritted glass filter. The filtrate was evaporated, ether (50 mL) was added, the product was filtered, washed with ether and dried to give Compound 15, 2.13 g (82%) as a colorless solid.

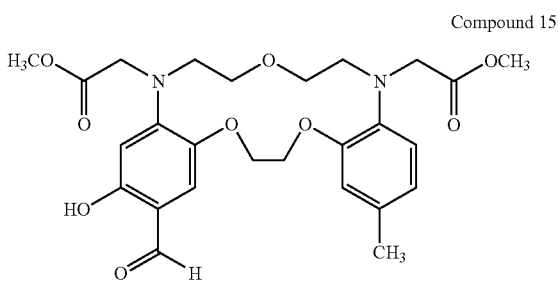

Compound 15

Example 11

Preparation of Compound 16

To a suspension of compound 15 (0.800 g, 1.55 mmol), $K_2CO_3$ (1.04 g, 7.5 mmol) and NaI (0.03 g, 0.2 mmol, catalyst) in DMF (10 mL) was added dropwise t-butyl bromoacetate (0.45 mL, 3.0 mmol). The mixture was stirred for 16 h, diluted with $H_2O$, extracted with $CHCl_3$, dried over $MgSO_4$ and evaporated. The residue was dissolved in hexane:EtOAc (1:1) and chromatographed on silica gel with 40% EtOAc in hexanes to give aldehyde 16, 0.875 g (90%) as colorless crystals.

Compound 16

Example 12

Preparation of Compound 17

A stirred mixture of diamine 11 (3.38 g, 10 mmol), bromoacetonitrile (14 mL, 200 mmol), DIPEA (26 mL, 150 mmol), NaI (1.5 g, 10 mmol; catalyst) in MeCN (150 mL) was heated at reflux for 70 h. After cooling to room temperature the MeCN was evaporated. The residue was dissolved in $CHCl_3$ (800 mL), washed with $H_2O$, dried over $MgSO_4$ and evaporated. The residue was chromatographed on $SiO_2$ with 40% EtOAc in hexanes to give Compound 17, 3.56 g (90%) as a colorless solid.

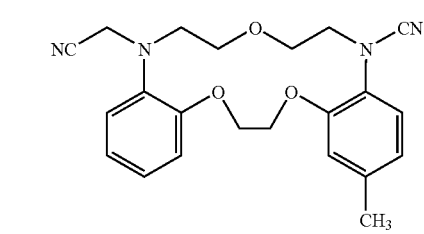

Compound 17

Example 13

Preparation of Compound 18

To a stirred solution of the Vilsmeier reagent prepared from $POCl_3$ (9.5 mL, 102 mmol) and 60 mL DMF was added over 5 min to a solution of Compound 17. The mixture was stirred for 100 h at 40° C., cooled by the addition of ice and neutralized with saturated $K_2CO_3$ to pH 8. The suspension was extracted with $CHCl_3$, washed with $H_2O$, dried over $MgSO_4$ and evaporated. The residue was chromatographed over $SiO_2$ using $CHCl_3$ as eluant to give compound 18, 3.12 g (73%) as colorless crystals.

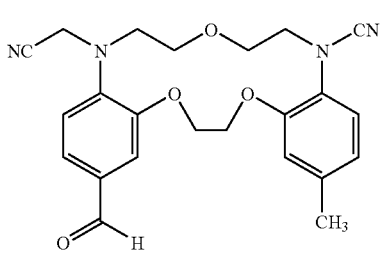

Compound 18

Example 14

Preparation of Compound 19

A mixture of aldehyde 18 (3.08 g, 7.3 mmol), ethylene glycol (8 mL, 140 mmol), p-toluenesulphonic acid (0.20 g, catalyst) and benzene (80 mL) was refluxed with a Dean-Stark trap for 4 h. After cooling to room temperature the mixture was evaporated. The residue was dissolved in $CHCl_3$ (300 mL), washed with saturated $NaHCO_3$, dried over $MgSO_4$, and evaporated to give compound 19, 2.82 g (85%) as an orange solid. Compound 19 was pure on TLC and used in the next step without additional purification.

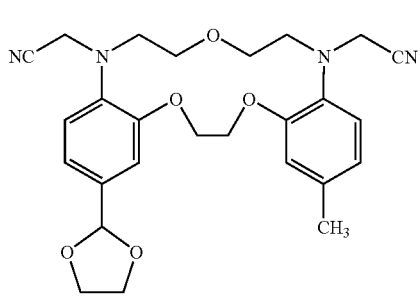

Compound 19

Example 15

Preparation of Compound 20

To a solution of Compound 19 (0.200 g, 0.44 mmol) in MeOH (25 mL) and 1 M NaOH (15 mL, 15 mmol) was added over 5 min 30% $H_2O_2$ (5 mL, catalyst). The mixture was stirred for 1 h, then acidified with 1 M HCl to pH 1. The acidified mixture was stirred for 30 min, diluted with 3 M NaOAc (150 mL), extracted with $CHCl_3$, washed with saturated $NaHCO_3$, dried over $MgSO_4$ and evaporated to give aldehyde 20, 0.191 g (95%) as a colorless crystalline material, pure by TLC.

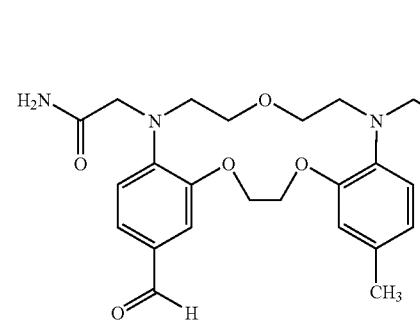

Compound 20

Example 16

Preparation of Compound 21

A mixture of aldehyde 13 (1.150 g, 2.3 mmol) and 4-fluororesorcinol (0.670 g, 5.2 mmol) in MeSO₃H (25 mL) was stirred overnight and then poured into 3 M NaOAc (300 mL). The precipitated solid was filtered, washed with H₂O and dried to give compound 21, 1.605 g (97%) as an off-white solid. Compound 21 was unstable to oxidation and was used in the next step without additional purification.

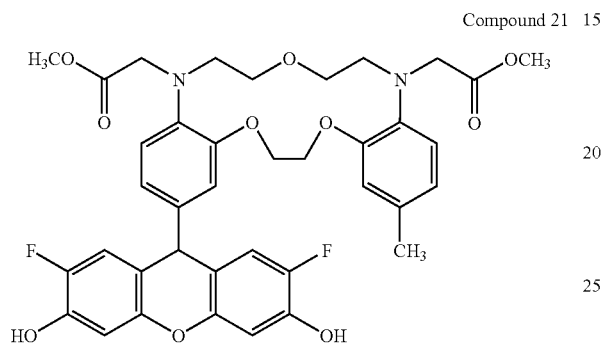

Compound 21

Example 17

Preparation of Compound 22

A mixture of Compound 21 (150 mg, 0.21 mmol) and chloranil (246 mg, 1.0 mmol) in MeOH (5 mL) and CHCl₃ (5 mL) was refluxed for 50 h, then cooled to room temperature, filtered from excess oxidizer, and evaporated. The residue was purified by preparative TLC on two SiO₂ plates using CHCl₃: MeOH:AcOH (20:2:1) to give compound 22, 44 mg (20%) as a red-brown solid.

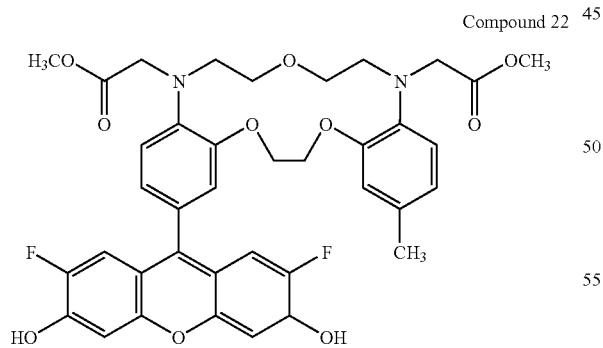

Compound 22

Example 18

Preparation of Compound 23

A mixture of Compound 22 (30 mg, 0.04 mmol) in MeOH (5 mL) and 1 M KOH (1 mL, 1.0 mmol) was stirred for 16 h, then neutralized with 1 M HCl to pH 7, and evaporated to dryness. The residue was purified by preparative TLC on two SiO₂ plates using CHCl₃:MeOH:AcOH (13:3:1) to give compound 23, 21 mg (74%) as a brown solid.

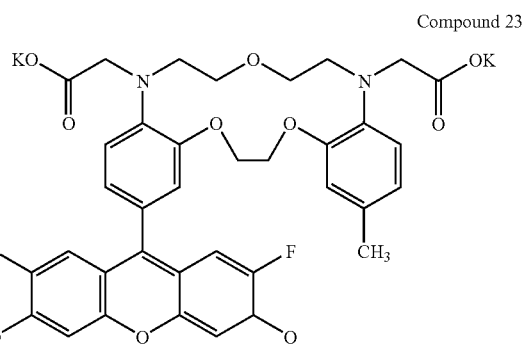

Compound 23

Example 19

Preparation of Compound 24

A mixture of Compound 22 (78 mg, 0.1 mmol), bromomethyl acetate (0.05 mL, 0.5 mmol), and DIPEA (0.175 mL, 1 mmol) in DMF (1 mL) was stirred for 2 h, then poured into 1% AcOH (200 mL). The suspension was extracted with CHCl₃, washed with H₂O, filtered and evaporated. The residue was purified by preparative TLC on two SiO₂ plates using 5% MeOH in CHCl₃: to give compound 24, 25 mg (32%) as a brown solid.

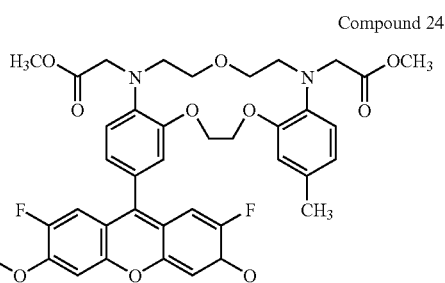

Compound 24

Example 20

Preparation of Compound 25

A mixture of Compound 23 (69 mg, 0.1 mmol), bromomethyl acetate (0.05 mL, 0.5 mmol), and DIPEA (0.175 mL, 1 mmol) in DMF (1 mL) was stirred for 2 h, then poured into 1% AcOH (200 mL). The suspension was extracted with CHCl₃, washed with H₂O, filtered and evaporated. The residue was purified by preparative TLC on two SiO₂ plates using 5% MeOH in CHCl₃ to give Compound 25 as a brown solid.

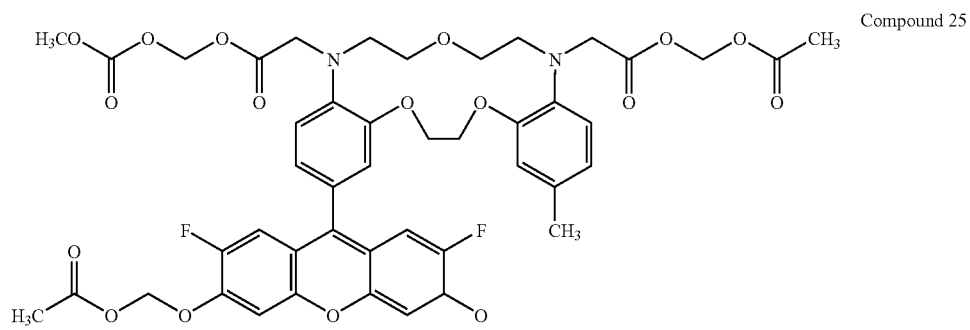
Compound 25

Example 21

Preparation of Compound 26

A mixture of aldehyde 13 (250 mg, 0.5 mmol), 3-dimethylaminophenol (157 mg, 1.1 mmol), and p-toluenesulphonic acid (10 mg, catalyst) in propionic acid (5 mL) was stirred overnight at 60° C., then cooled to room temperature and poured into 3 M NaOAc (100 mL). The precipitated solid was filtered, washed with H$_2$O and dried to give compound 26, 360 mg (97%) as a rose-colored solid. Compound 26 was unstable to oxidation and was used in subsequent reactions without additional purification.

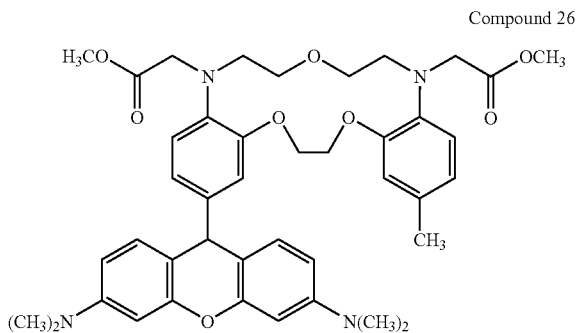
Compound 26

Example 22

Preparation of Compound 27

A mixture of Compound 26 (660 mg, 0.81 mmol) and chloranil (400 mg, 1.62 mmol) in MeOH (25 mL) and CHCl$_3$ (25 mL) was stirred for 2 h, filtered from excess oxidizer, and evaporated. The residue was purified by chromatography on SiO$_2$ using 9% MeOH and 1% AcOH in CHCl$_3$ as eluant to give the crude product, which was again chromatographed on SiO$_2$ using the same eluant to give Compound 27, 112 mg (19%) as crimson solid.

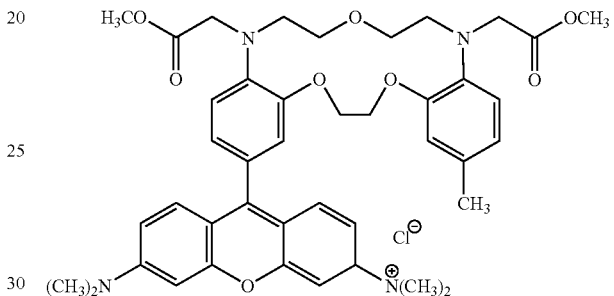
Compound 27

Example 23

Preparation of Compound 28

A mixture of Compound 27 (40 mg, 0.05 mmol) in MeOH (2 mL) and 1 M KOH (1 mL, 1.0 mmol) was stirred for 16 h and then evaporated to dryness. The residue was purified by chromatography on a SEPHADEX LH-20 column using H$_2$O as eluant to give salt 28, 8 mg (21%) as red flakes after lyophilization.

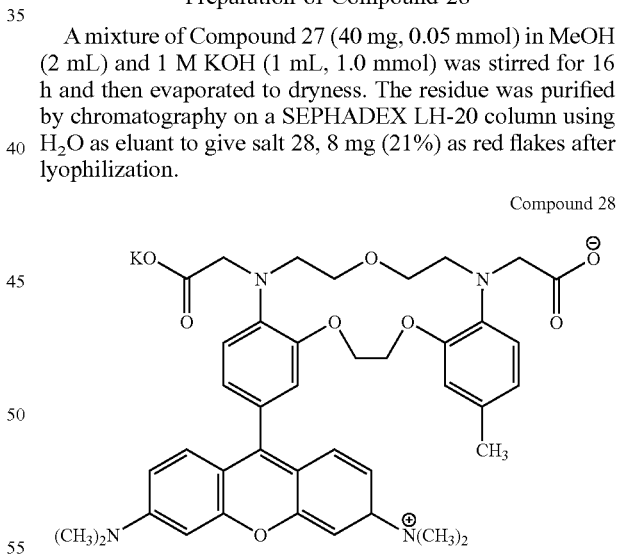
Compound 28

Example 24

Preparation of Compound 29

A mixture of Compound 28 (75 mg, 0.1 mmol), bromomethyl acetate (0.1 mL, 1.0 mmol), and DIPEA (0.35 mL, 2 mmol) in DMF (2 mL) was stirred for 2 h, then poured into 1% AcOH (200 mL). The suspension is extracted with CHCl$_3$, washed with H$_2$O, filtered and evaporated. The residue was purified by preparative TLC on two SiO$_2$ plates using 5% MeOH in CHCl$_3$ to give Compound 29 as a red solid.

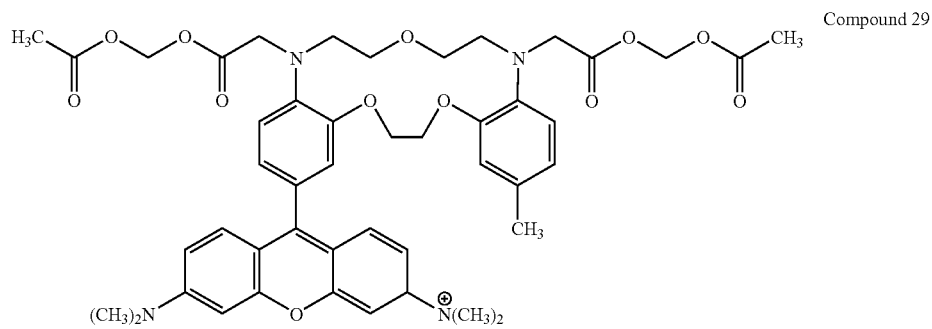

Compound 29

Example 25

Preparation of Compound 30

Compound 30 was prepared analogously to Compound 27, using 8-hydroxyjulolidine rather than m-dimethylaminophenol.

Compound 30

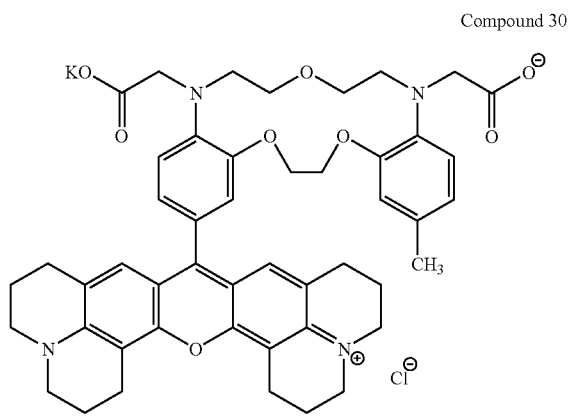

Example 26

Preparation of Compound 31

Compound 31 was prepared form Compound 27 using the procedure for preparing Compound 28 from Compound 27.

Compound 31

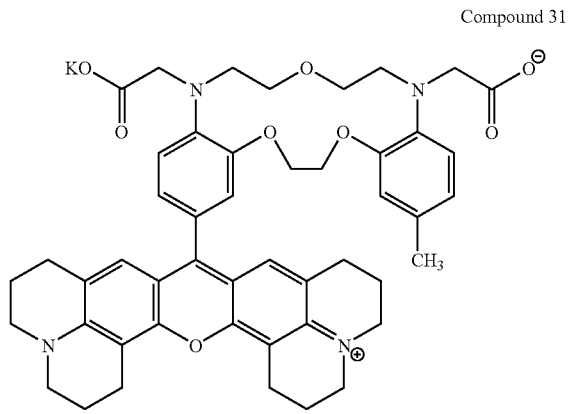

Example 27

Preparation of Compound 32

To a solution of aldehyde 13 (250 mg, 0.5 mmol) in CH$_2$Cl$_2$ (20 mL) was added 2,4-dimethylpyrrole (0.125 mL, 1.2 mmol). The solution was stirred for 5 min, then TFA (0.046 mL, 0.6 mmol) is introduced. After 16 h, the mixture was diluted with CHCl$_3$ (150 mL), washed with 2% tetrabutylammonium hydroxide (150 mL) then H$_2$O then evaporated. The residue was dissolved in toluene (20 mL) and stirred for 3 h with chloranil (148 mg, 0.6 mmol). DIPEA (0.87 mL, 5 mmol) was introduced, followed by BF$_3$ etherate (0.52 mL, 4 mmol). The mixture was evaporated and the residue was purified by chromatography on SiO$_2$ using a gradient of 0–2% MeOH in CHCl$_3$ to give compound 32, 102 mg (28%) as a brown solid.

Compound 32

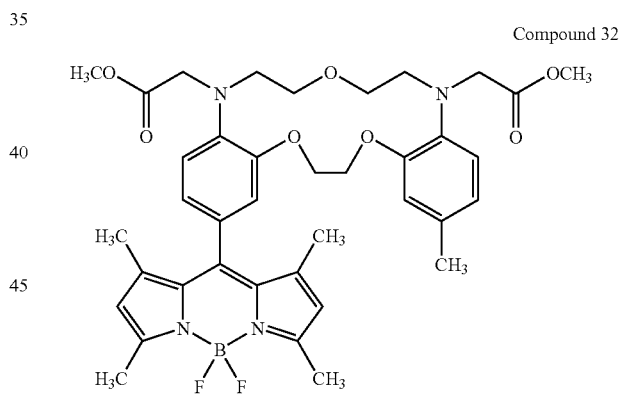

Example 28

Preparation of Compound 33

A mixture of aldehyde 13 (1.00 g, 2.0 mmol), the Wittig base (4-methoxycarbonyl-2-nitrobenzyl)triphenylphosphonium bromide (1.34 g, 2.5 mmol), and K$_2$CO$_3$ (1.38 g, 10 mmol) in DMF (20 mL) was stirred for 16 h at 95° C. More of the Wittig base (0.500 g, 0.93 mmol) was added and the mixture was stirred for an additional 6 h, then cooled to room temperature and poured into H$_2$O. The solution was acidified with 1 M HCl to pH 3, extracted with CHCl$_3$, dried over MgSO$_4$, and evaporated. The crude product was purified by chromatography on SiO2 using CHCl$_3$ then 2% MeOH in CHCl$_3$ to give compound 33, 0.915 g (68%) as an orange solid.

Compound 33

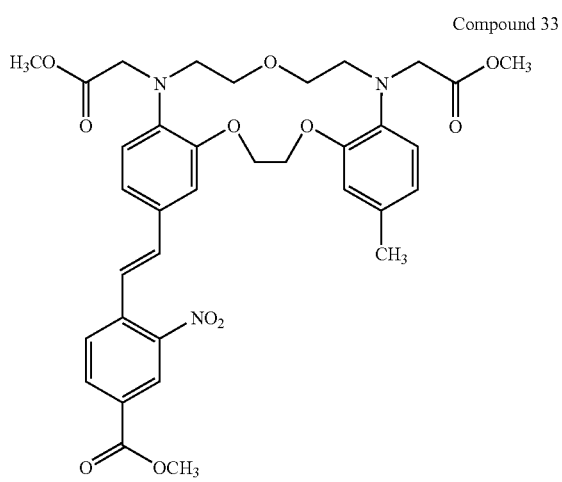

Example 29

Preparation of Compound 34

A mixture of the ethylene derivative 33 (70 mg, 0.1 mmol) and triethylphosphite (3 mL) was heated at 120° C. for 6 h, then evaporated and subsequently co-evaporated with DMF (3×10 mL). The residue was purified by preparative TLC on two SiO$_2$ plates using 7% MeOH in CHCl$_3$ as eluant to give compound 34, 52 mg (80%) as a slightly yellowish solid.

Compound 34

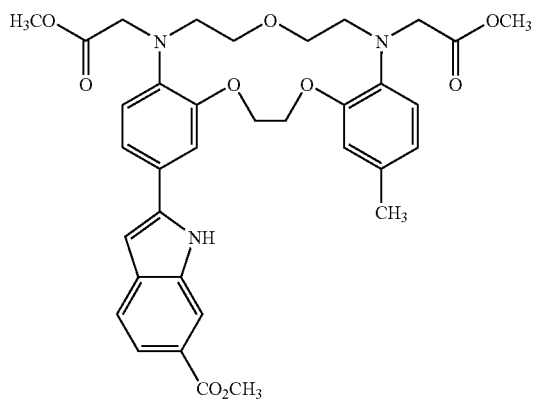

Example 30

Preparation of Compound 35

A mixture of Compound 34 (300 mg, 0.46 mmol), and 1 M KOH (6 mL, 6 mmol) in MeOH (25 mL) was stirred for 16 h. More 1 M KOH (5 mL, 5 mmol) was added and the mixture was stirred for an additional 6 h, then evaporated to half its original volume, and acidified with 1 M HCl to pH 3. The suspension was extracted with CHCl$_3$ then with n-BuOH. The combined organic extract was filtered and was evaporated. Ether (20 mL) was added and the precipitated solid was filtered and washed with ether to give compound 35, 157 mg (57%) as an off-white solid.

Compound 35

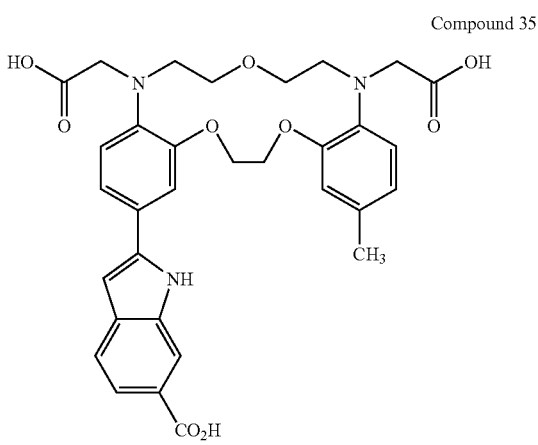

Example 31

Preparation of Compound 36

A mixture of Compound 35 (72 mg, 0.12 mmol), bromomethyl acetate (0.14 mL, 1.0 mmol), and DIPEA (0.35 mL, 2 mmol) in DMF (5 mL) was stirred for 16 h, poured into 1% AcOH (200 mL), extracted with CHCl$_3$, washed with H$_2$O then evaporated. The residue was purified by preparative TLC on two SiO$_2$ plates using 5% MeOH in CHCl$_3$ to give Compound 36, 3 mg (3%) as a brown solid.

Compound 36

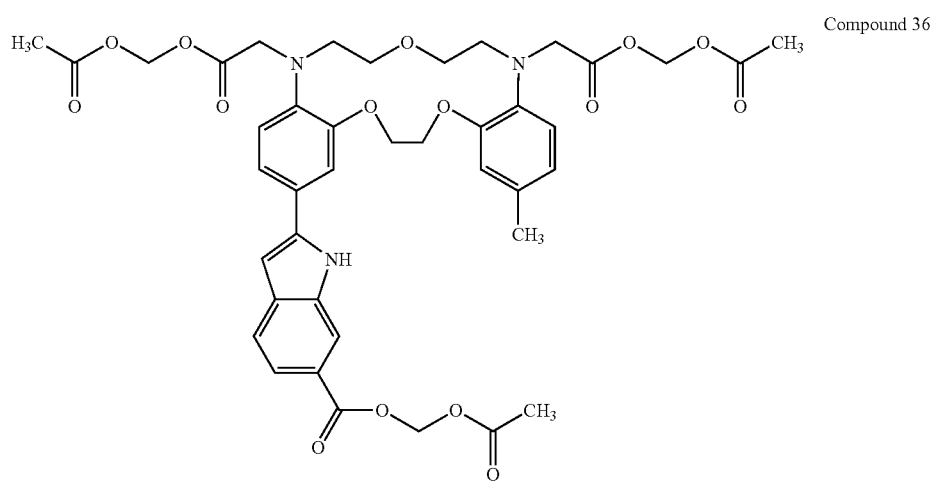

Example 32

Preparation of Compound 37

A mixture of aldehyde 16 (630 mg, 1.0 mmol), 3-dimethylaminophenol (330 mg, 2.4 mmol), and p-toluenesulphonic acid (20 mg, catalyst) in propionic acid (5 mL) was stirred for 16 h at 60° C., then cooled to room temperature and poured into 3 M NaOAc (150 mL). The precipitated solid was filtered, washed with $H_2O$ and dried to give Compound 37, 360 mg (97%) as a rose solid. Compound 37 is unstable to oxidation and was used in next step without additional purification.

Compound 37

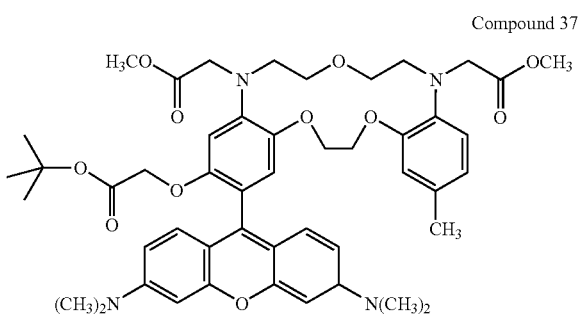

Example 33

Preparation of Compound 38

A mixture of Compound 37 (2.50 g, 2.9 mmol) and chloranil (1.42 g, 5.8 mmol) in MeOH (100 mL) and $CHCl_3$ (100 mL) was stirred for 4 h, filtered from excess oxidizer, and evaporated. The residue was purified by chromatography on $SiO_2$ using a gradient of 6–10% MeOH and 1% AcOH in $CHCl_3$ to give compound 38, 1.13 g (45%) as a crimson solid.

Compound 38

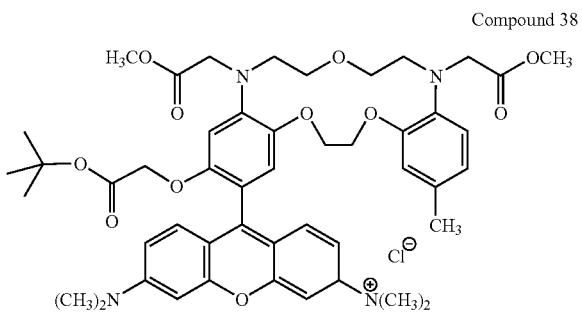

Example 34

Preparation of Compound 39

A mixture of Compound 38 (500 mg, 0.58 mmol) in $CH_2Cl_2$ (20 mL) and TFA (20 mL) was stirred for 4 h, then evaporated and co-evaporated with $CHCl_3$. Ether (25 mL) was added to the residue and the precipitated product was filtered and washed with ether to give Compound 39, 447 mg (95%) as a violet-red solid.

Compound 39

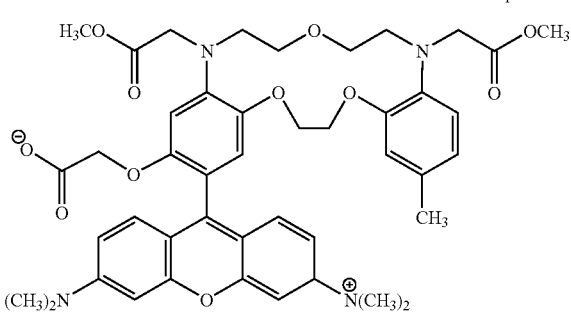

Example 35

Preparation of Compound 40

A mixture of Compound 39 (20 mg, 0.1 mmol), bromomethyl acetate (0.025 mL, 0.25 mmol), and DIPEA (0.08 mL, 0.5 mmol) in DMF (1 mL) was stirred for 3 h. More bromomethyl acetate (0.025 mL, 0.25 mmol) and DIPEA (0.08 mL, 0.5 mmol) were added and the mixture was stirred for an additional 3 h, diluted with $CHCl_3$ (100 mL), washed with 1% AcOH then $H_2O$ then evaporated. The residue was purified by preparative TLC on two $SiO_2$ plates using 10% MeOH and 0.5% ACOH in $CHCl_3$ to give Compound 40, 12 mg (54%) as a dark red solid.

Compound 40

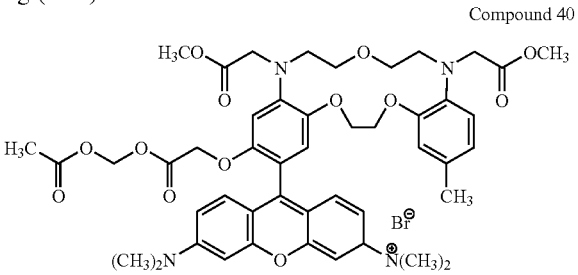

Example 36

Preparation of Compound 41

To a stirred solution of Compound 39 (162 mg, 0.2 mmol) and pyridine (0.08 mL, 1 mmol) in DMF (5 mL), was added dry N-trifluoroacetoxysuccinimide (90 mg, 0.4 mmol). After 7 h more N-trifluoroacetoxysuccinimide (90 mg, 0.4 mmol) and pyridine (0.08 mL, 1 mmol) were added, and the mixture was stirred for 16 h more. Analytical TLC confirmed the formation of the single product, while starting material 39 was consumed. Compound 41 was very reactive and unstable towards isolation attempts. It was used in further transformations upon preparation in DMF solution without isolation and purification.

Compound 41

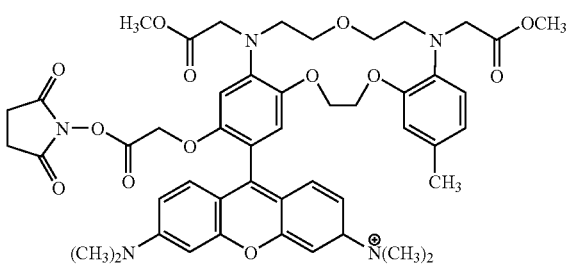

Example 37

Preparation of Compound 42

To a stirred solution of succinimidyl ester 41 prepared as in Example 36 from compound 39 (81 mg, 0.1 mmol) in DMF (2 mL) was added dry hexadecylamine (135 mg, 0.5 mmol). The mixture was stirred for 16 h, diluted with CHCl$_3$(150 mL), washed with 1% ACOH the H$_2$O, dried over MgSO$_4$, and evaporated. The residue was purified by preparative TLC on two SiO$_2$ plates using CHCl$_3$ as eluant to give Compound 42, 57 mg (54%) as a red oil.

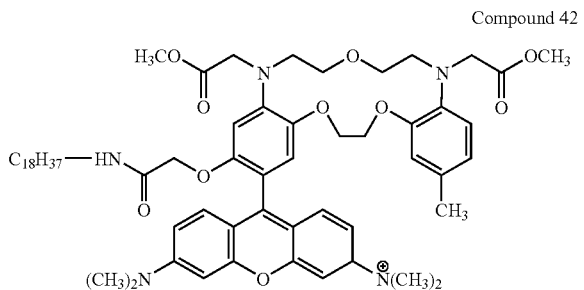

Compound 42

Example 38

Preparation of Compound 43

To a stirred solution of succinimidyl ester 41 prepared as in Example 36 from Compound 39 (81 mg, 0.1 mmol) in DMF (2 mL) was quickly introduced a solution of 5-aminopentanoic acid (40 mg, 0.3 mmol) and 1 M methanolic tetrabutylammonium hydroxide (1 mL, 1 mmol) in H$_2$O (5 mL). The mixture was stirred for 4 h, then diluted with H$_2$O (100 mL), acidified with AcOH to pH 4, extracted with CHCl$_3$, dried over MgSO$_4$ and evaporated. The residue was purified by preparative TLC on two SiO$_2$ plates using 10% MeOH and 2.5% AcOH in CHCl$_3$ as the eluent to give Compound 43, 56 mg (61%) as a red solid.

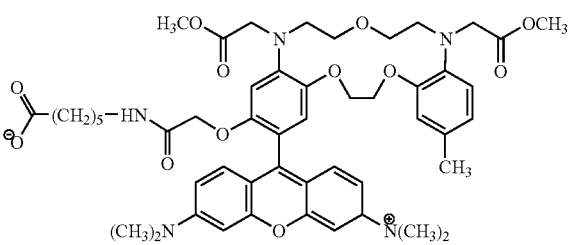

Compound 43

Example 39

Preparation of Compound 44

To a stirred solution of Compound 43 (37 mg, 0.04 mmol) and pyridine (0.08 mL, 1 mmol) in DMF (1 mL), was added dry N-trifluoroacetoxysuccinimide (36 mg, 0.16 mmol). After 4 h, more N-trifluoroacetoxysuccinimide (36 mg, 0.4 mmol) and pyridine (0.08 mL, 1 mmol) are added, and the mixture was stirred for an additional 16 h. The mixture was diluted with CHCl$_3$ (100 mL), washed with 1% AcOH then H$_2$O then evaporated. Hexanes (5 mL) were added to the residue. The precipitated solid was filtered, washed with hexanes and dried to give Compound 44, 15 mg (37%) as a dark red solid.

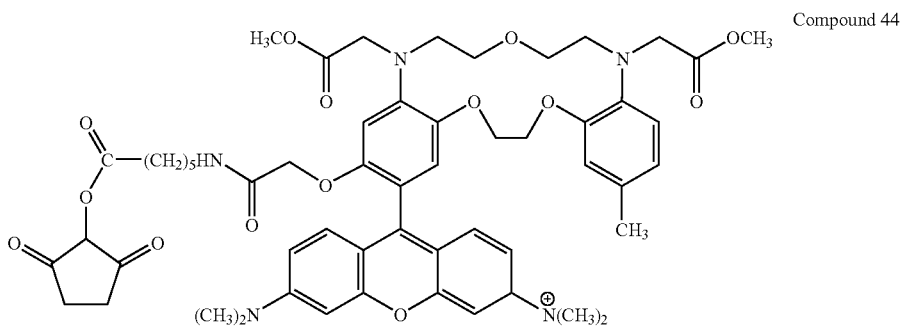

Compound 44

Example 40

Preparation of Compound 45

A solution of succinimidyl ester 41 (81 mg, 0.1 mmol) in DMF (2 mL) was added to 5 mL of aqueous aminodextran (100 mg, 0.037 eq.) and 1 M methanolic tetrabutylammonium hydroxide (1 mL, 1 mmol). The mixture was stirred for 16 h, poured into MeOH (400 mL), and the precipitated conjugate was filtered off and washed with MeOH. The crude product was dissolved in H$_2$O (3 mL), filtered through a membrane filter and loaded onto a SEPHADEX G-15 resin column pre-equilibrated with H$_2$O. The colored fraction was eluted in a void volume and lyophylized to give labeled dextran 45, (41 mg) as a red solid.

Compound 45

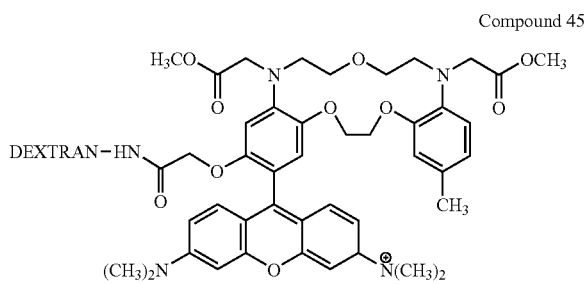

Example 41

Preparation of Compound 46

To a stirred solution of succinimidyl ester 41 (81 mg, 0.1 mmol) in DMF (2 mL) was added Et₃N (0.14 mL, 1 mmol) followed by 2-(4-aminophenyl)ethylamine (0.05 mL, 0.5 mmol). The mixture was stirred for 2 h, diluted with CHCl₃ (150 mL), washed with 1% AcOH then H₂O then evaporated. Ether (5 mL) was added to the residue, and the solid was filtered off, washed with ether and dried to give Compound 46 as a dark red solid, pure on TLC and HPLC.

Example 43

Preparation of Compound 48

To a stirred solution of aldehyde 16 (630 mg, 1.0 mmol) in CH₂Cl₂ (40 mL), 2,4-dimethylpyrrole (0.25 mL, 2.4 mmol) was added. The solution was stirred for 5 min, then TFA (0.1 mL, 1.2 mmol) was introduced. The mixture was stirred for 16 h, and diluted with CHCl₃ (300 mL). The chloroform solution was washed with 2% tetrabutylammonium hydroxide then H₂O, evaporated, and subsequently co-evaporated with toluene. The residue was dissolved in toluene (40 mL), stirred for 2 h with chloranil (296 mg, 1.2 mmol), then DIPEA (1.74 mL, 10 mmol) was introduced, followed by BF₃ etherate (1.04 mL, 8 mmol). The mixture was evaporated and the residue was purified by chromatography on SiO₂ using a gradient of 0–1% MeOH in CHCl₃ to give Compound 48, 280 mg (35%) as a brown solid.

Compound 46

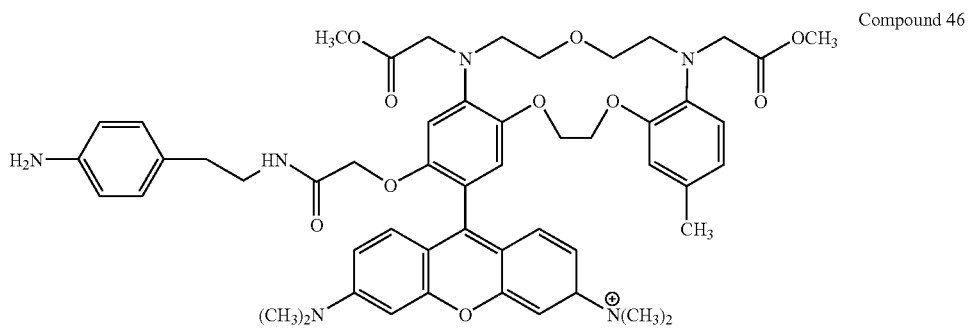

Example 42

Preparation of Compound 47

To a solution of Compound 46 (9 mg, 0.01 mmol) in AcOH (2 mL) was added a 1 M CSCl₂ solution in CHCl₃ (0.1 mL, 0.1 mmol). The mixture was stirred for 2 h then evaporated. Ether (5 mL) was added to the residue, and the precipitated solid was filtered off, washed with ether and dried to give Compound 47, 9 mg (95%) as a dark red solid. Compound 47 reacts quickly with n-BuNH₂ in pre-column derivatization for HPLC analysis.

Compound 48

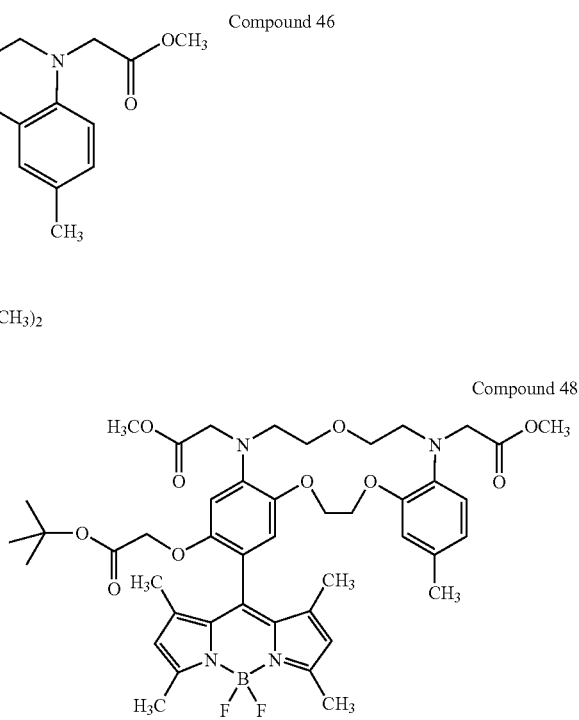

Compound 47

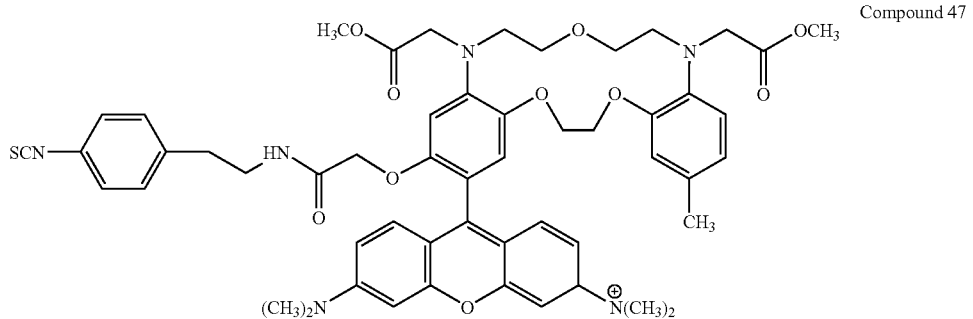

Example 44

Preparation of Compound 49

A mixture of Compound 48 (120 mg, 0.15 mmol) in CHCl₃ (6 mL) and TFA (0.4 mL) was stirred for 16 h, then evaporated and co-evaporated with CHCl₃. The residue was purified by preparative TLC on two SiO₂ plates using 10% MeOH in CHCl₃ as eluant to give Compound 49, 82 mg (77%) as a brown solid.

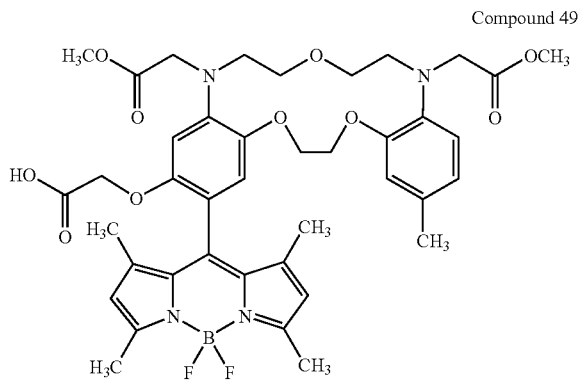

Compound 49

Example 45

Preparation of Compound 50

A mixture of Compound 49 (80 mg, 0.11 mmol), bromomethyl acetate (0.05 mL, 0.5 mmol), and DIPEA (0.17 mL, 1.0 mmol) in DMF (2 mL) was stirred for 2 h, poured into H₂O (150 mL), and extracted with CHCl₃. The extract was dried over MgSO₄ then evaporated. The residue was purified by preparative TLC on two SiO₂ plates using 3% MeOH and 0.5% ACOH in CHCl₃ to give Compound 50, 46 mg (52%) as a brown solid.

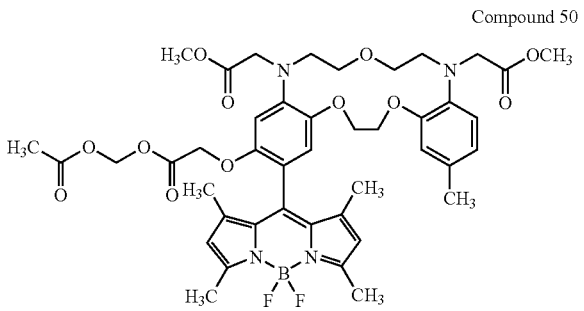

Compound 50

Example 46

Preparation of Compound 51

A mixture of aldehyde 15 (800 mg, 1.55 mmol), 5-carboxy-2-chloromethyloxazole (300 mg, 1.86 mmol), K₂CO₃ (1.07 g, 7.75 mmol), and NaI (75 mg, 0.5 mmol; catalyst) in DMF (20 mL) was stirred at 135° C. for 4 h, then poured into H₂O. The mixture was acidified with 1 M HCl to pH 3, extracted with CHCl₃, dried over MgSO₄ then evaporated. The residue was purified by chromatography on SiO₂ using a gradient of 5–20% MeOH and 1–2% AcOH in CHCl₃ as eluant to give Compound 51, 255 mg (26%) as a yellowish solid.

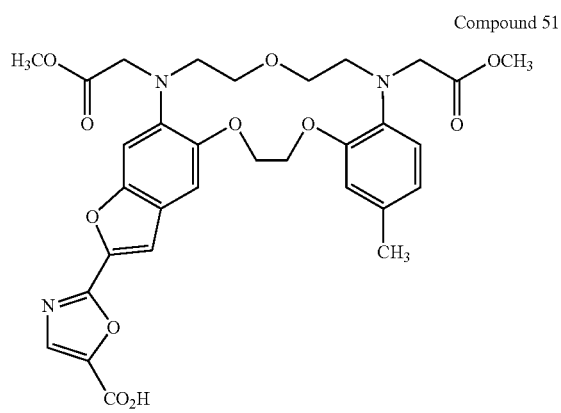

Compound 51

Example 47

Preparation of Compound 52

A mixture of Compound 51 (62 mg, 0.1 mmol), bromomethyl acetate (0.05 mL, 0.5 mmol), and DIPEA (0.17 mL, 1.0 mmol) in DMF (1 mL) was stirred for 2 h, poured into 1% ACOH (100 mL), and extracted with CHCl₃. Then 3 M NaOAc (100 mL) was added to the aqueous phase and the mixture was extracted with more CHCl₃. The combined extracts were dried over MgSO₄ then evaporated. The residue was purified by preparative TLC on two SiO₂ plates using 5% MeOH in CHCl₃ to give Compound 52, 29 mg (42%) as an orange solid.

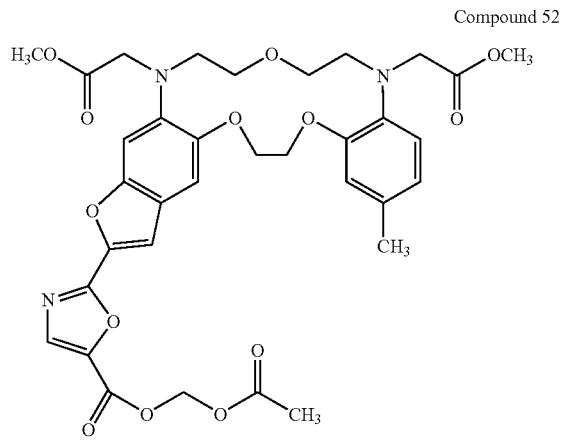

Compound 52

Example 48

Preparation of Compound 53

A mixture of aldehyde 15 (1.40 g, 2.71 mmol), 2-chloromethyl-5-ethoxycarbonyloxazole (0.564 g, 1.86 mmol), $K_2CO_3$ (1.87 g, 13.60 mmol), and NaI (0.150 g, 1.00 mmol; catalyst) in DMF (30 mL) was stirred at 135° C. for 4 h and then poured into $H_2O$. The mixture was acidified with 1 M HCl to pH 3, extracted with $CHCl_3$ and evaporated. The residue was purified by chromatography on $SiO_2$ using 1% MeOH in $CHCl_3$ as eluant to give Compound 53, 1.260 g (71%) as a yellowish solid.

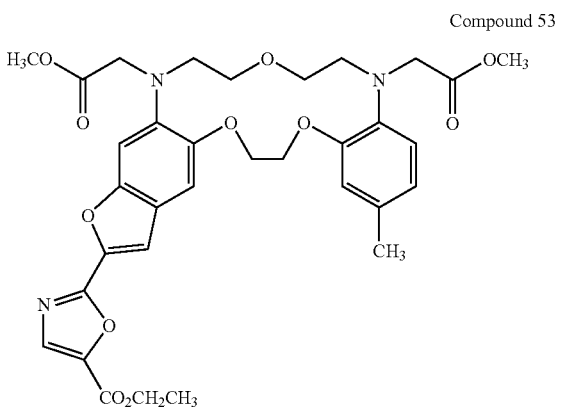

Compound 53

Example 49

Preparation of Compound 54

A mixture of Compound 53 (376 mg, 0.5 mmol) and 1 M KOH (3 mL, 3.0 mmol) in MeOH (5 mL) was stirred for 5 h, then evaporated to ⅕ volume, and acidified with 1 M HCl to pH 2.8. The precipitated solid was filtered, washed with $H_2O$ and dried on a filter. This crude product was suspended in $H_2O$ (2 mL) and then made basic with 0.1 M KOH to pH 9.5. The solution was loaded onto a SEPHADEX LH-20 resin column and chromatographed using $H_2O$ as eluant to give Compound 54, 256 mg (72%) as a yellow-greenish solid.

Example 50

Preparation of Compound 55

A mixture of Compound 54 (71 mg, 0.1 mmol), bromomethyl acetate (0.1 mL, 1.0 mmol), and DIPEA (0.35 mL, 2.0 mmol) in DMF (2 mL) was stirred for 4 h, diluted with $CHCl_3$, then washed with 1% AcOH then $H_2O$ and evaporated. The residue was purified by preparative TLC on two $SiO_2$ plates using 5% MeOH and 0.5% AcOH in $CHCl_3$ to give compound 55, 63 mg (77%) as an orange solid.

Example 51

Preparation of Compound 56

A mixture of aldehyde 16 (315 mg, 0.5 mmol), the Wittig base (4-methoxycarbonyl-2-nitrobenzyl)triphenylphosphonium bromide (375 mg, 0.7 mmol), and $K_2CO_3$ (345 mg, 2.5 mmol) in DMF (3 mL) was stirred for 6 h at 95° C. then cooled to room temperature and poured into $H_2O$. The solution was acidified to pH 5 with 1 M HCl and extracted with $CHCl_3$. The extract was dried over $MgSO_4$ and evaporated. The crude product was purified by chromatography on $SiO_2$ using $CHCl_3$, then 0.5% MeOH in $CHCl_3$ to give Compound 56, 339 mg (84%) as an orange solid.

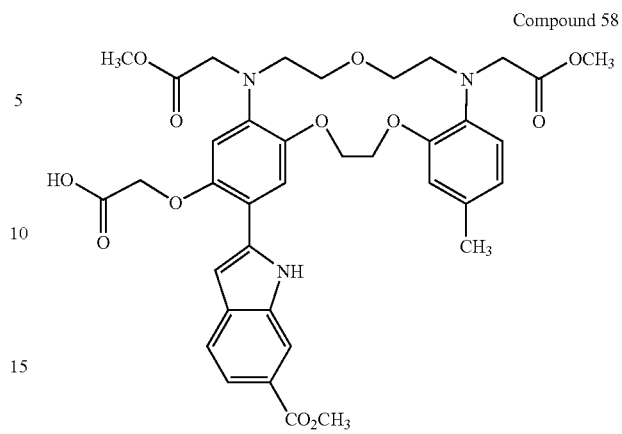

Compound 56

Example 52

Preparation of Compound 57

A mixture of the ethylene derivative 56 (338 mg, 0.42 mmol) and triethylphosphite (8 mL) was heated at 130° C. for 7 h, then evaporated and subsequently co-evaporated with DMF. The residue was first purified by chromatography on $SiO_2$ using $CHCl_3$ followed by 1% MeOH in $CHCl_3$, then by preparative TLC on two $SiO_2$ plates using 50% EtOAc in hexanes as eluant to give Compound 57, 112 mg (34%) as a slightly yellowish solid.

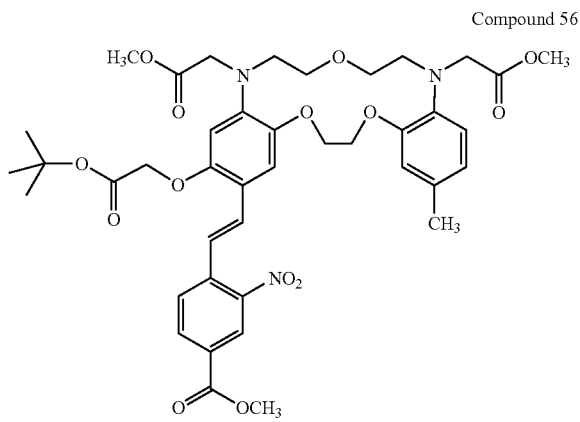

Compound 57

Example 53

Preparation of Compound 58

A mixture of Compound 57 (104 mg, 0.13 mmol) in $CH_2Cl_2$ (2 mL) and TFA (2 mL) was stirred for 3 h, then evaporated and co-evaporated with $CHCl_3$. The residue was purified by preparative TLC on two $SiO_2$ plates using 7% MeOH and 2% AcOH in $CHCl_3$ to give Compound 58, 55 mg (57%) as a yellowish solid.

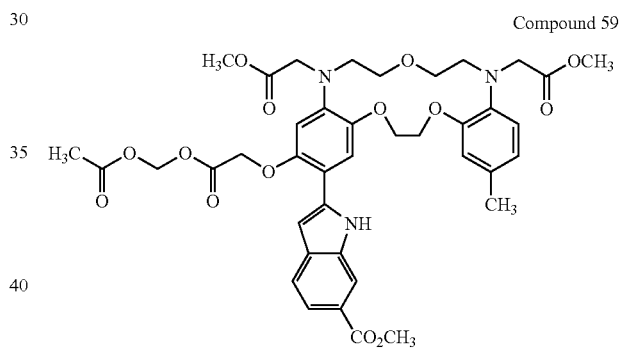

Compound 58

Example 54

Preparation of Compound 59

A mixture of Compound 58 (22 mg, 0.03 mmol), bromomethyl acetate (0.1 mL, 1.0 mmol), and DIPEA (0.26 mL, 1.5 mmol) in DMF (2 mL) was stirred for 16 h, then diluted with $CHCl_3$ (100 mL), washed with 1% ACOH then $H_2O$ then evaporated. The residue was purified by preparative TLC on two $SiO_2$ plates using 5% MeOH in $CHCl_3$ to give compound 59, 16 mg (67%) as an orange solid.

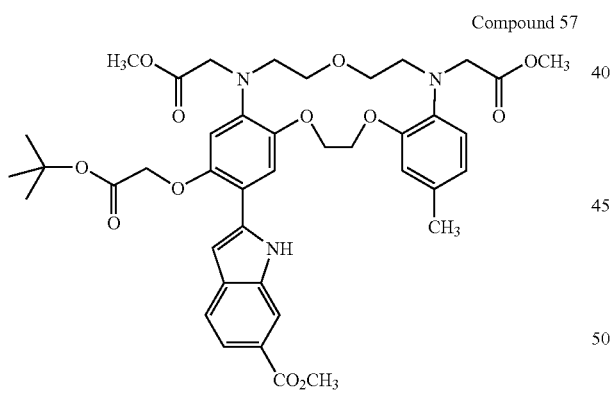

Compound 59

Example 55

Preparation of Compound 60

A mixture of Compound 38 (87 mg, 0.1 mmol) and 1 M KOH (2 mL, 2 mmol) in MeOH (5 mL) was stirred for 16 h, and evaporated. The residue was purified on SEPHADEX LH-20 resin using $H_2O$ as the eluant. The fractions containing product were collected and lyophilized to give Compound 60, 12 mg (14%) as a crimson solid.

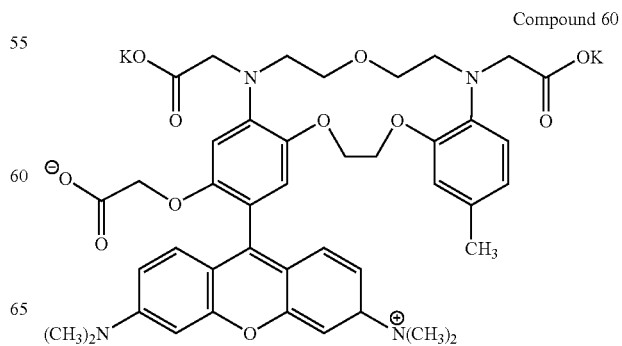

Compound 60

Example 56

Preparation of Compound 61

A mixture of Compound 60 (8 mg, 0.01 mmol), bromomethyl acetate (0.025 mL, 0.25 mmol), and DIPEA (0.08 mL, 0.5 mmol) in DMF (1 mL) was stirred for 16 h, and diluted with CHCl₃ (100 mL). The solution was washed with 1% ACOH then H₂O then evaporated. Ether (5 mL) was added to the residue. The precipitated solid was filtered off and washed with ether to give Compound 61, 5 mg (50%) as a dark red solid. Compound 61 was pure on TLC and HPLC.

Example 58

Preparation of Compound 63

A mixture of the ethylene derivative 62 (170 mg, 0.28 mmol) and triethylphosphite (4 mL) was heated at 120° C. for 16 h, then evaporated and subsequently co-evaporated with DMF. The residue was purified by preparative TLC on two SiO₂ plates using 3% MeOH in CHCl₃ as eluant, then on two SiO₂ plates using 40% EtOAc in hexanes as eluant to give Compound 63, 26 mg (16%) as a yellowish solid.

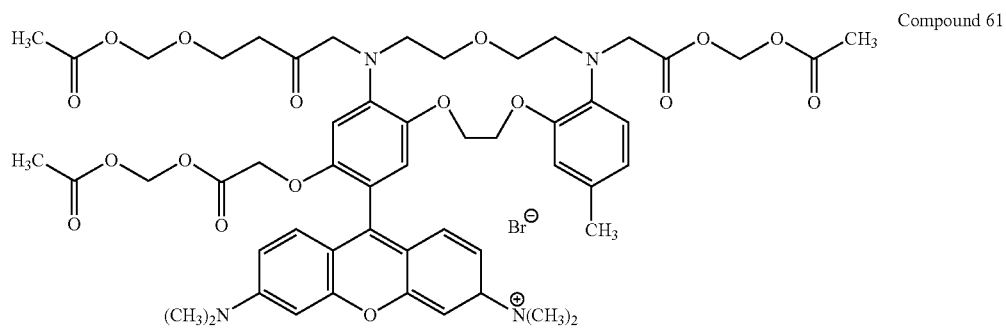

Compound 61

Example 57

Preparation of Compound 62

A mixture of aldehyde 18 (217 mg, 0.5 mmol), the Wittig base (4-methoxycarbonyl-2-nitrobenzyl)triphenylphosphonium bromide (536 mg, 0.7 mmol), and K₂CO₃ (345 mg, 2.5 mmol) in DMF (3 mL) was stirred for 16 h at 95° C., then cooled to room temperature and poured into H₂O. The solution was acidified with 1 M HCl to pH 3, extracted with CHCl₃, dried over MgSO₄ and evaporated. The crude product was purified by chromatography on SiO₂ using CHCl₃, as eluant to give Compound 62, 171 mg (56%) as an orange solid.

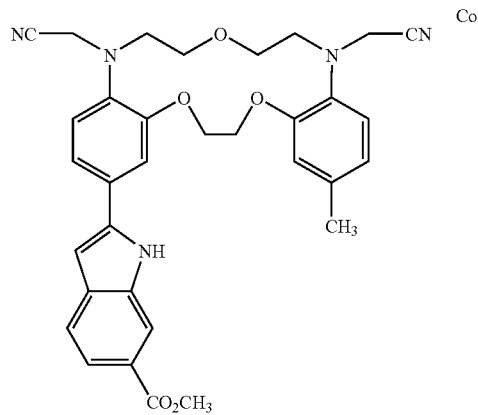

Compound 63

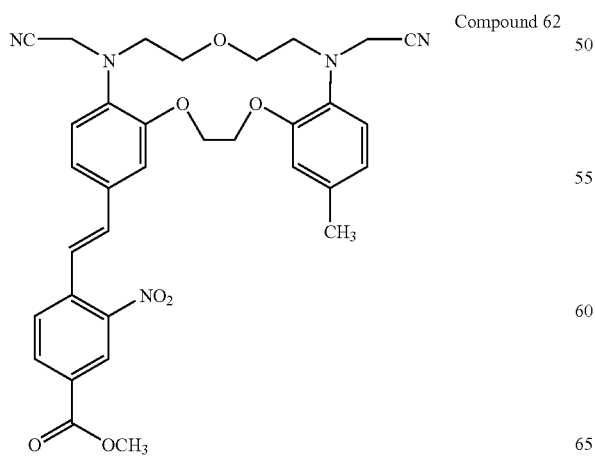

Compound 62

Example 59

Preparation of Compound 64

A mixture of aldehyde 20 (100 mg, 0.21 mmol), 3-dimethylaminophenol (55 mg, 0.40 mmol), and p-toluenesulphonic acid (5 mg, catalyst) in propionic acid (2 mL) was stirred overnight at 60° C., then cooled to room temperature and poured into 3 M NaOAc (40 mL). Precipitated solid was filtered, washed with H₂O and dried to give Compound 64, 140 mg (93%) as a rose-colored solid. Compound 64 was unstable to oxidation and was used in next step without additional purification.

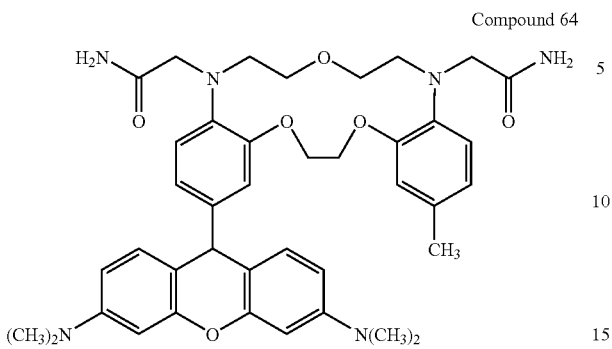

Compound 64

Example 60

Preparation of Compound 65

A mixture of Compound 64 (138 mg, 0.20 mmol) and chloranil (84 mg, 0.34 mmol) in MeOH (5 mL) and CHCl₃ (5 mL) was stirred for 4 h, and evaporated. The residue was purified by chromatography on SiO₂ using a gradient of 7–9% MeOH and 0.5–1% AcOH in CHCl₃ as eluant to give Compound 65, 118 mg (86%) as a dark red solid.

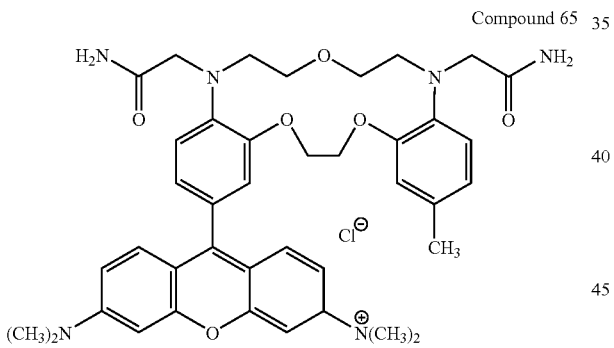

Compound 65

Example 61

Preparation of Compound 66

To a 0.5 M solution of arene 12 in sulfuric acid is added one equivalent of potassium nitrate. The resulting solution is stirred until TLC analysis of reaction aliquots, treated with water and ether, shows full conversion to nitroarene 66. The reaction mixture is poured into excess aqueous sodium acetate, followed by extraction with ether. The extract is washed with aqueous sodium bicarbonate and brine, dried over magnesium sulfate and then concentrated to a reddish-brown oil, which is purified by trituration with ether-hexanes to give Compound 66 as a yellow powder.

Compound 66

Exampl 62

Preparation of Compound 67

A 0.5 M solution of Compound 66 in methanol is treated with 10% palladium on charcaol, at 10 wt % of Compound 66. The resulting mixture is shaken under 40 psi hydrogen until TLC analysis shows full conversion to aniline 67. The reaction mixture is filtered through diatomaceous earth, followed by concentration in vacuo. The residue is triturated with ether-hexanes to give pure Compound 67 as an off-white powder.

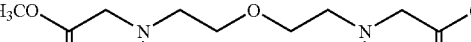

Compound 67

Example 63

Preparation of Compound 68

A mixed anhydride of 6-carboxytetramethylrhodamine is prepared according to the procedure given in U.S. Pat. No. 5,453,517 to Kuhn et al. To a solution of the mixed anhydride and one equivalent of diisopropylethylamine in anhydrous THF under nitrogen is added slowly a 0.3 M solution of Compound 67. The resulting mixture is stirred until TLC analysis indicates consumption of Compound 67. The reaction mixture is concentrated in vacuo, and the residue partitioned between chloroform and water. The chloroform layer is washed with brine and dried over magnesium sulfate, then concentrated in vacuo. The residue is purified by flash chromatography on silica gel using increasing amounts of methanol in chloroform as eluant to give pure Compound 68 as a red powder.

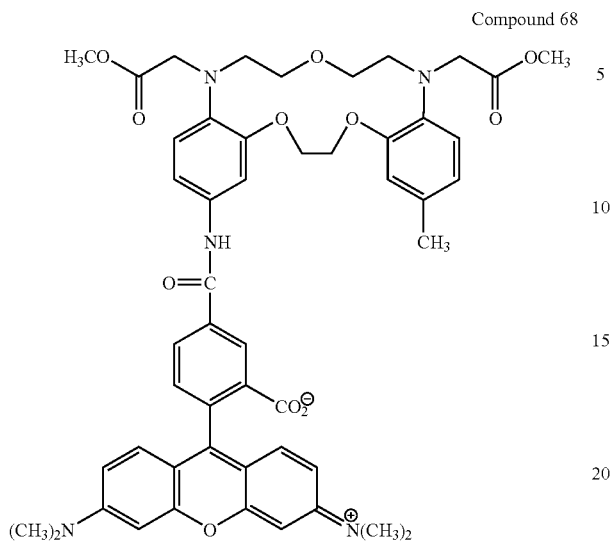

Compound 68

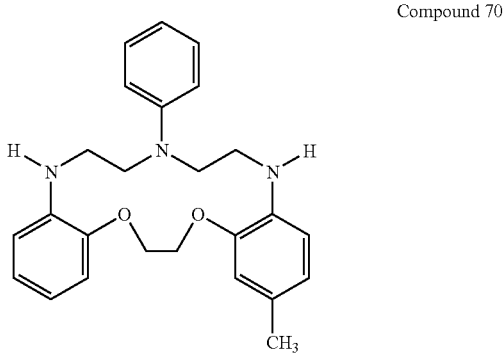

Compound 70

Example 66

Preparation of Compound 71

The bisaniline 70 is alkylated to give Compound 71, as described for Compound 12.

Example 64

Preparation of a Tris-Aza Crown Ether (69)

To a dilute solution (0.1 M) of diamine 9 and two equivalents of DIPEA in anhydrous THF is slowly added at room temperature a dilute solution (0.1 M) of N,N-bis (chlorocarbonylmethyl)-aniline. After stirring overnight, the volatiles are removed by evaporation, and the residue is partitioned between 5% hydrochloric acid and ethyl acetate. The organic layer is washed with brine, dried, and concentrated. The resulting residue is purified by column chromatography on silica gel using increasing amounts of methanol in chloroform to give pure Compound 69.

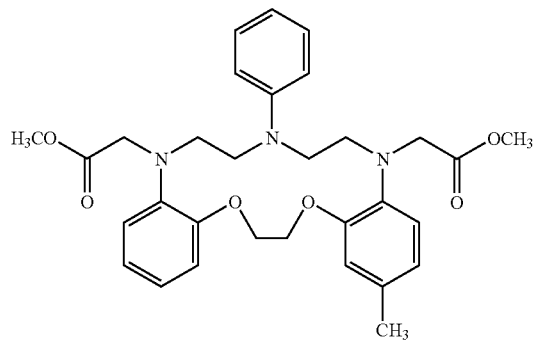

Compound 71

Example 67

Preparation of Compound 72

The bisester 71 is formylated to give the aldehyde Compound 72, as described for Compound 13.

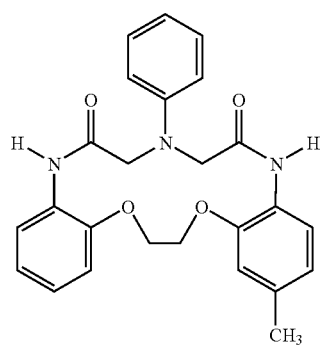

Compound 69

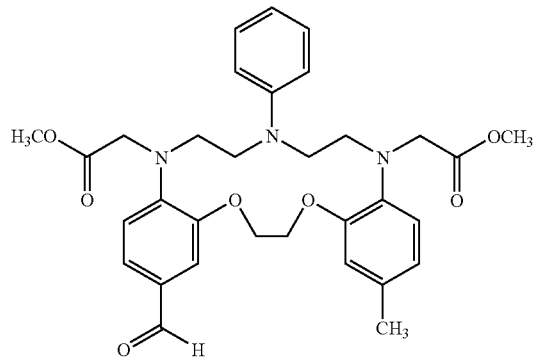

Compound 72

Example 65

Preparation of Compound 70

The bisamide 69 is reduced to bisaniline 70 as described for Compound 11.

Example 68

Preparation of Compound 73

The aldehyde 72 is condensed with two equivalent of 3-(dimethylamino)phenol as described for Compound 26 to give Compound 73.

Compound 73

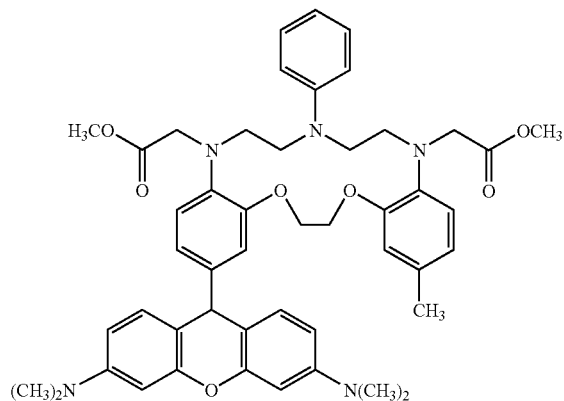

Example 69

Preparation of Compound 74

Compound 73 is oxidized with chloranil to give the chloride salt 74 as a red powder, as described for Compound 27.

Compound 74

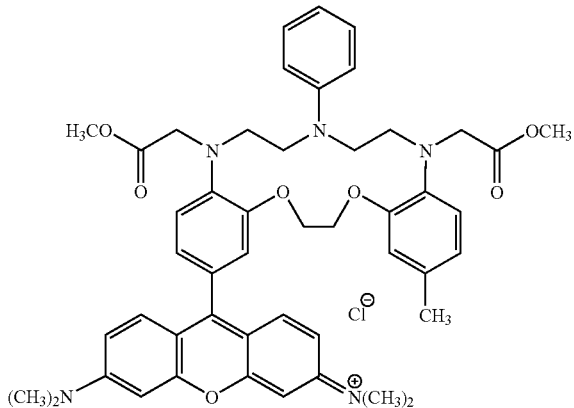

Example 70

Preparation of a Thia-Substituted Crown Ether (75)

A bis-aza crown ether that incorporates a sulfur atom in the crown is prepared using the procedures of Examples 64–69, except that in place of N,N-bis(chlorocarbonylmethyl)-aniline, the bis-acid chloride of thiodiglycolic acid is used (Cl(C=O)CH$_2$—S—CH$_2$(C=O)Cl). After preparation of the crown ether itself, condensation with 3-(N,N-dimethylamino)phenol, and oxidation, the chloride salt of the thia-crown ether, Compound 75, is isolated as a red powder.

Compound 75

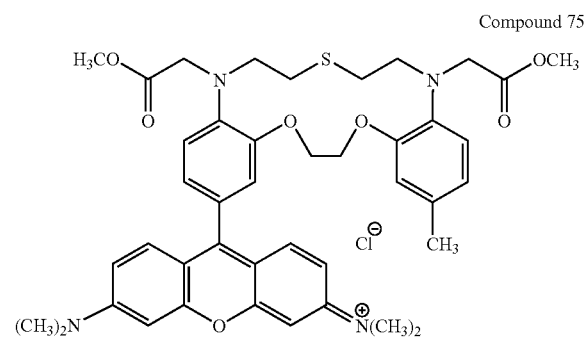

Example 71

Determination of Na+, K+, Li+ and Tb+ Indicator Fluorescence Response

The fluorescence response of a selected compound of the invention as a function of ion concentration was determined by dissolving a sample of the pure compound in 3 mL of each of two solutions: solution 1 ("high") consists of 200 mM NaCl (or other appropriate ion) and 10 mM MOPS buffer at pH 7.05; solution 2 ("zero") consists of 10 mM MOPS buffer at pH 7.05 in deionized water. A series of curves are generated by cross dilution between the two solutions to arrive at intermediate concentrations of Na+, K+, Li+ and Tb+. The emission of a selected indicator in solution 2 was scanned and then was repeated to cover the entire range from zero to 200 mM Na$^+$. For example, the fluorescence emission of the chosen indicator was scanned while the sample was excited at that indicator's absorption maximum wavelength, and then $\frac{1}{100}$ of the sample was removed and replaced with $\frac{1}{100}$ of solution 1 to arrive at a Na$^+$ concentration of 2 mM. This dilution was repeated to cover the entire range from zero to 1 M Na$^+$ and the resulting emission intensities were plotted versus the ion concentrations. A least-squares fit was used to arrive at the concentration where the selected indicator was maximally sensitive to changes in Na$^+$ concentration. This corresponded to the dissociation constant of that indicator for Na$^+$ and was expressed as a concentration.

Figure 4A:
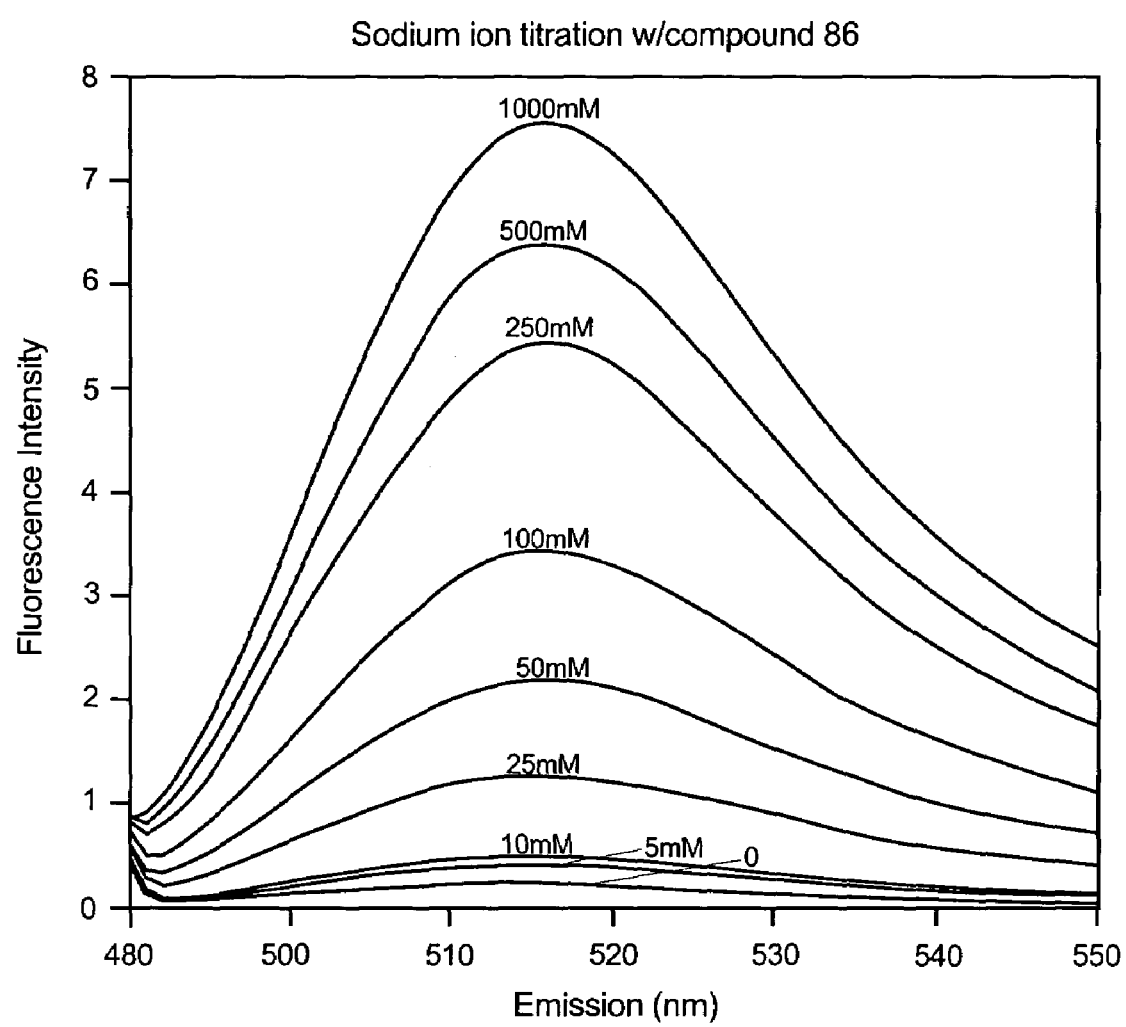
FIG. 4: Shows the Na+ (FIG. 4A) and K+ (FIG. 4B)-*dependent* fluorescent emission spectra of Compound 86 in a series of solutions containing 0 to 1000 mM free Na+ and 0 to 5M of free K+ ions, with excitation at 488 nm. See, Example 71.
Figure 4B:
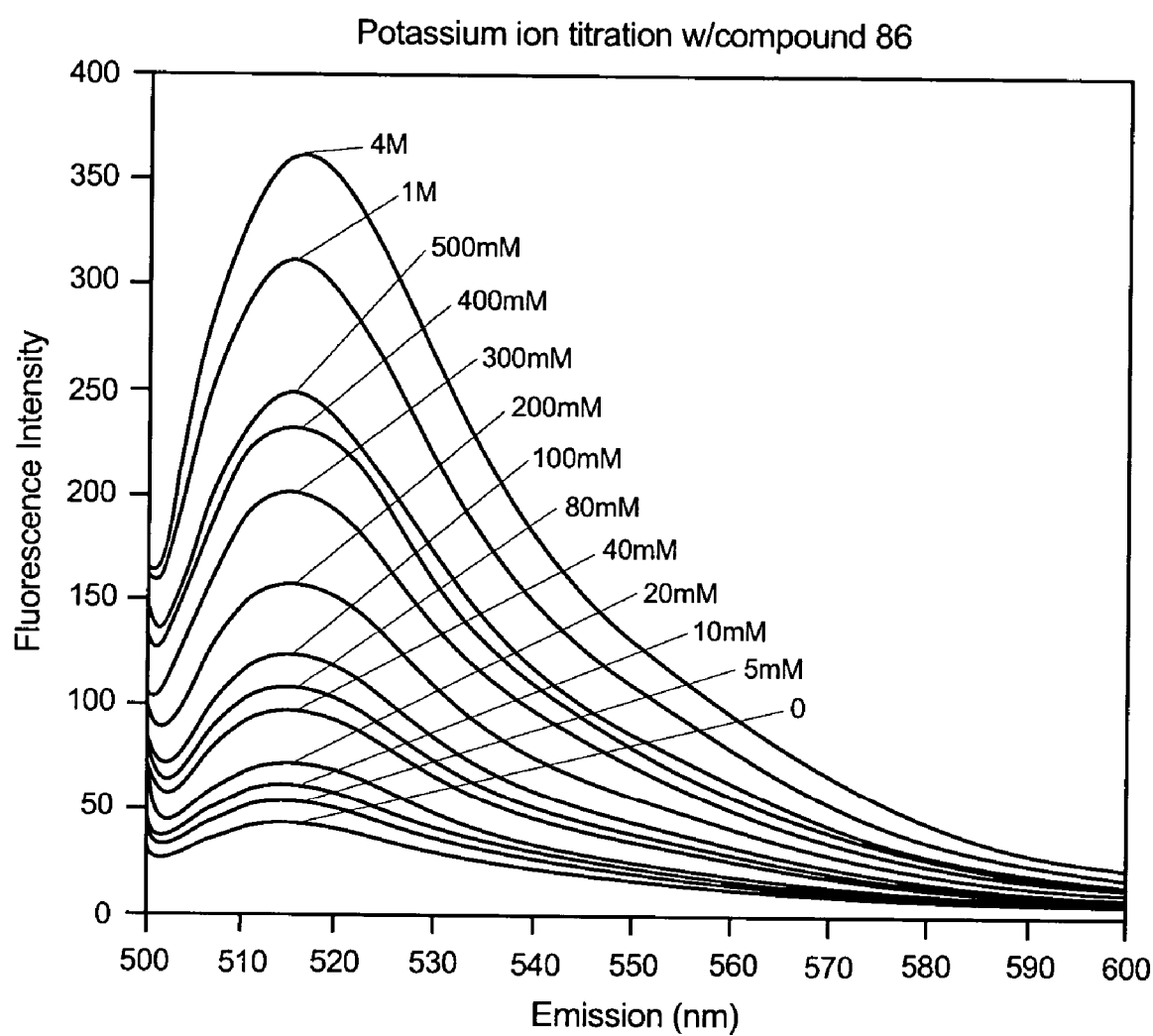
Figure 5:
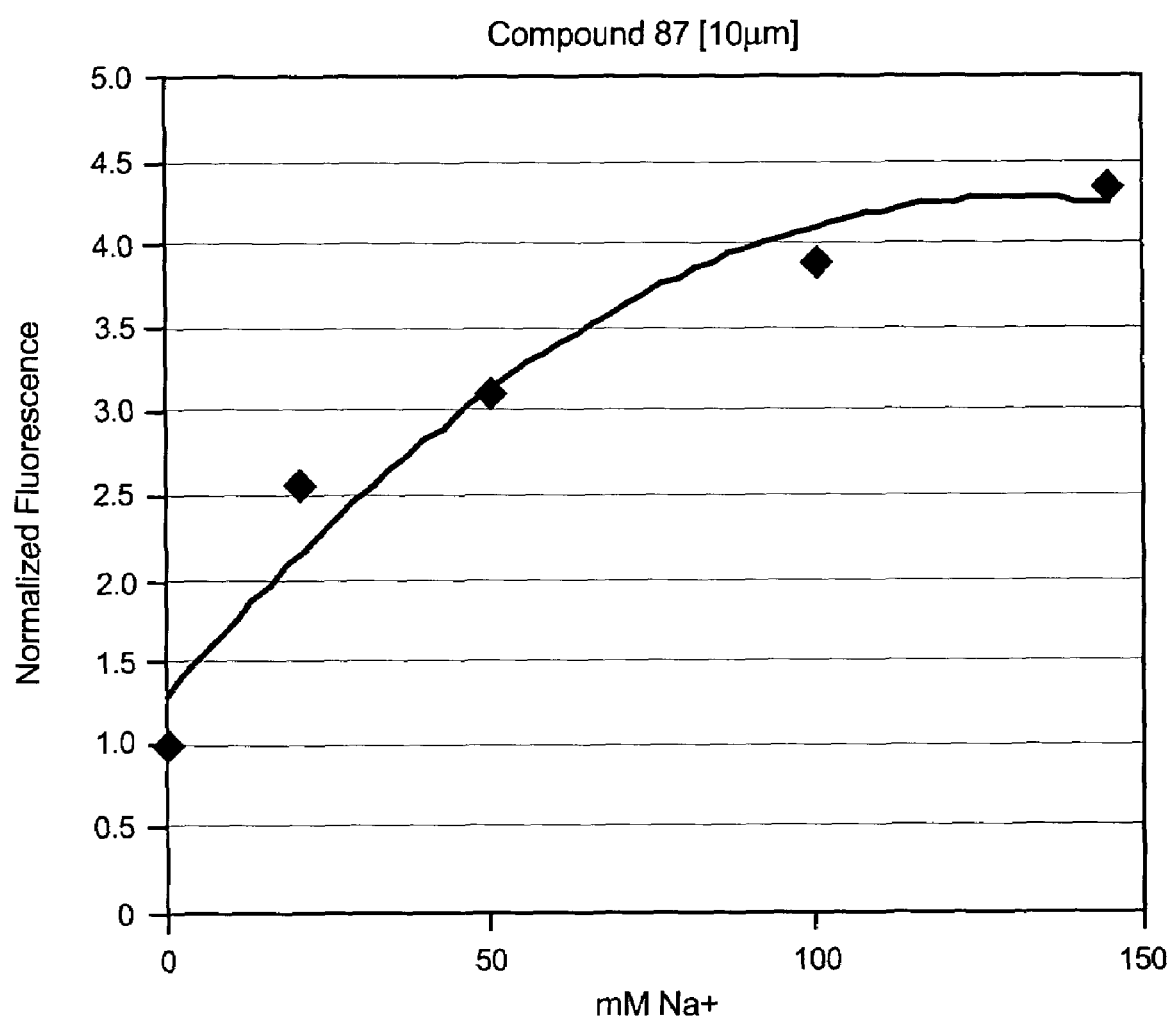
FIG. 5: Shows intracellular detection of Na+ ions with Compound 87. See, Example 72.

This methodology was repeated for K+, Li+ and Tb+ to obtain emission spectra and to calculate the Kd values. See, Table 2 and FIG. 4

For visible wavelength probes such as Compound 22 (Example 17), Compound 27 (Example 22) and Compound 86 (Example 79) the indicator's fluorescence emission was typically scanned from 450–650 nm while the sample was excited at the absorption maximum wavelength. For UV-excitable ratiometric probes such as Compound 51 (Example 46), the excitation wavelengths of the dye in solution 2 were scanned from 260 to 450 nm while monitoring constant fluorescence emission at 510 nm (as in FIG. 1).

The binding affinity of a selected indicator for sodium ions, in the presence of potassium ions, is determined using the process above, except in the presence of 100 mM K$^+$ concentrations.

Example 72

Calibration of Sodium Indicator Fluorescence Response in Cells

Figure 3:
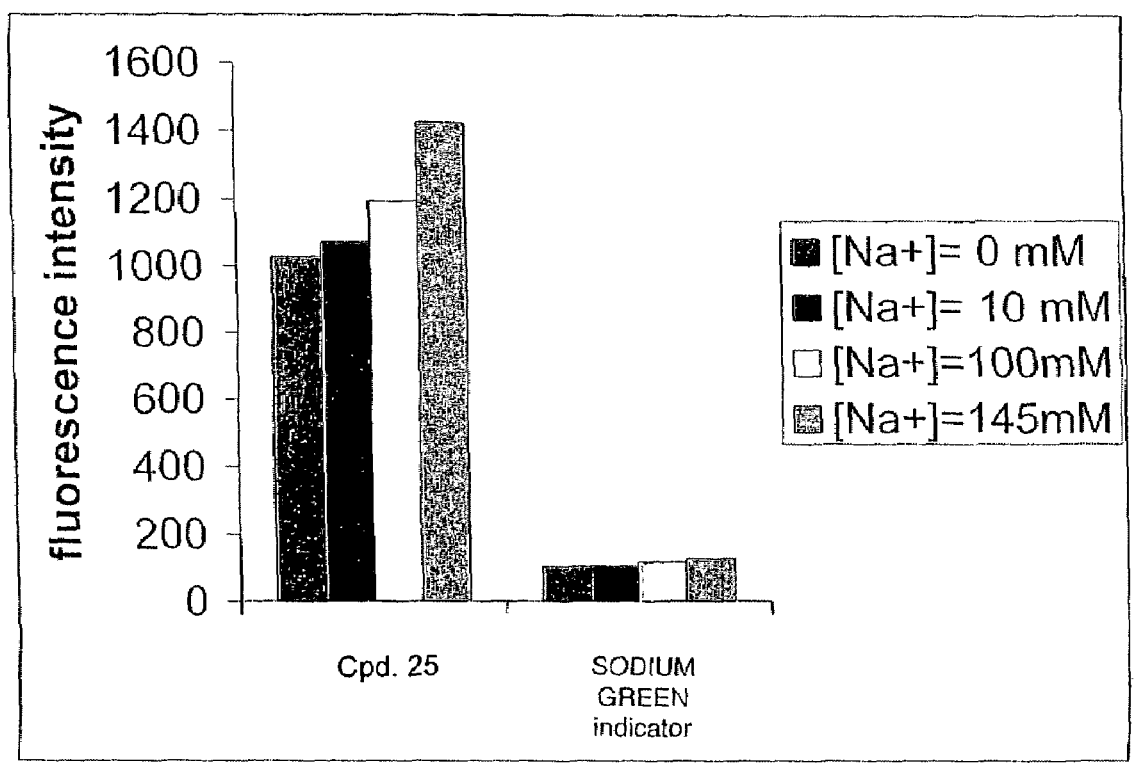
FIG. 3: Shows a comparison of the intracellular sodium response of SODIUM GREEN tetraacetate indicator (Molecular Probes, Inc.) or Compound 25. At every intracellular $Na^+$ concentration, Compound 25 demonstrates stronger fluorescence intensity than SODIUM GREEN sodium indicator at the same concentration (as described in Example 72).

Jurkat cells were loaded with a 5 µM solution of either Compound 25 (Example 20), or commercially available SODIUM GREEN tetraacetate indicator (Molecular Probes, Inc., Eugene, Oreg.) and 10 µM for Compound 87 (Example 80) for 30 minutes at 37° C. The use of PLURONIC dispersing agent helped dissolve the selected indicator. Intracellular sodium concentrations were then established by varying the sodium concentration of the extracellular buffer in the presence of 2 µM gramicidin (a sodium-pore forming antibiotic). The extracellular buffer was set at 0 mM, 10 mM, 20 mM, 50 mM, 100 mM, and 145 mM, respectively. Intracellular fluorescence response of the selected indicators was measured using a FACSCAN flow cytometer and associated software, with fluorescence excitation at 488 nm. Compound 25 exhibits substantially brighter intracellular fluorescence intensity than the SODIUM GREEN indicator at comparable $Na^+$ concentrations, as shown in FIG. 3. Similarly, as intracellular $Na^+$ concentration was increased, Compound 25 exhibits a consistent increase in fluorescence intensity. Compound 87 demonstrated an increased fluorescent signal with increasing concentrations of sodium ions.

Example 73

Preparation of a Biotinylated Indicator (Compound 76)

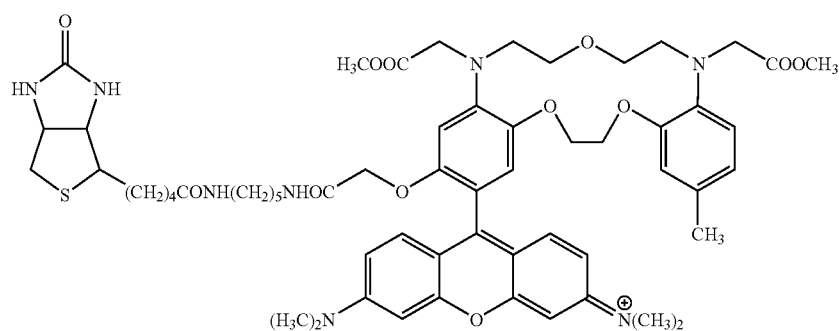

Compound 76

To a stirred solution of succinimidyl ester 41 prepared as in Example 36 from compound 39 (81 mg, 0.1 mmol) in DMF (2 mL) was added $Et_3N$ (0.27 mL, 2 mmol) followed by biotin-cadaverin trifluoracetate (66 mg, 02 mmol). The mixture was stirred for 16 h, diluted with $CHCl_3$ (100 mL), washed 1% AcOH (3×50 mL), $H_2O$ (100 mL) dried over $MgSO_4$ and evaporated. The residue was purified by preparative TLC on four C18 reverse-phase plates using 50% aqueous 2-PrOH with 0.2% TFA as eluant to give Compound 76, 25 mg (22%) as an orange solid.

Example 74

Avidin-Labeling with a Biotinylated Fluorescent Crown Ether

A 5 mg/mL solution of streptavidin in phosphate-buffered saline (PBS, pH 7.0) is treated with a 1 mg/mL solution of biotinylated indicator (e.g., Compound 212, Example 73) in 2% DMSO/PBS at a molar ratio such that two equivalents of biotinylated indicator are present for every streptavidin molecule. The resulting solution is incubated at 37° C. for 4 hours and then centrifuged. The supernatant is applied to a Sephadex G-25 gel filtration column (2 mL bed volume/mg protein) and eluted with PBS. The streptavidin-indicator complex elutes first. Fractions are analyzed by TLC to ensure that no free indicator is present in the complex. Pure product fractions are pooled and lyophilized. The complex is useful as a bridging method to apply the indicator to any biotinylated surface or substance.

Example 75

Preparation of 1-Aza-benzo-15-crown-5 ether (82)

To a solution of 2-aminophenol 81 (1.322 g, 12 mmol) in MeCN (1 L), powdered CsF (7.300 g, 48 mmol) is added. The mixture is stirred vigorously for 1 h and then tetraethyleneglycole ditosylate (6.100 g, 12 mmol) in MeCN (50 mL) is introduced. The mixture is refluxed under $N_2$ atmosphere for 24h and evaporated. The residue is dissolved in $CHCl_3$ (800 mL), washed with $H_2O$, sat. $NaHCO_3$, $H_2O$, sat. NaCl (200 mL each), filtered through paper, and evaporated. The crude product is purified by column chromatography on silica gel (12×60 cm bed column, made in $CHCl_3$) using $CHCl_3$ as eluant to give compound 82, 1.995 g (62% yield) as a low melting solid.

Example 76

Preparation of 1-Methoxycarbonylmethyl-1-aza-benzo-15-crown-5-ether (83)

The mixture of compound 82 (1.380 g, 5.17 mmol), DIEA (2.4 mL, 25.84 mmol), methyl bromoacetate (1.8 mL, 10.34 mmol), and NaI (0.750 g, 5.00 mmol) in MeCN (100 mL) is refluxed under $N_2$ atmosphere for 24 h, then cooled and evaporated. The residue is re-dissolved in in $CHCl_3$ (400 mL), washed with 1% AcOH (2×200 mL), $H_2O$ (200 mL). The chloroform solution is dried over $MgSO_4$, filtered through paper, and evaporated. The crude product is purified by column chromatography on silica gel (3×30 cm bed column, made in $CHCl_3$) using 0–2.5% MeOH gradient in $CHCl_3$ as eluant to give compound 83, 1.102 g (63% yield) as a yellow oil.

Example 77

Preparation of 15-Formyl-1-methoxycarbonylmethyl-1-aza-benzo-15-crown-5-ether (84)

To a solution of the Vilsmeier reagent prepared from POCl$_3$ (1.0 mL, 11.0 mmol) in 5 mL DMF, compound 83 (0.750 g, 2.20 mmol) in DMF (2 mL) is introduced. The mixture is stirred under a N$_2$ atmosphere for 16 h, then poured into ice (20 g)/sat. K$_2$CO$_3$ (50 mL) mixture. The mixture is extracted with CHCl$_3$ (50+5×10 mL), and the extract is dried over MagSO$_4$ and evaporated. The crude product is purified by column chromatography on silica gel (1.5×30 cm bed column, made in CHCl$_3$) using CHCl$_3$ as eluant to give aldehyde 84, 0.632 g (78% yield) as an off-white low-melting solid.

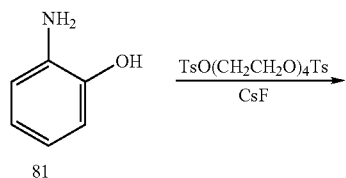

81

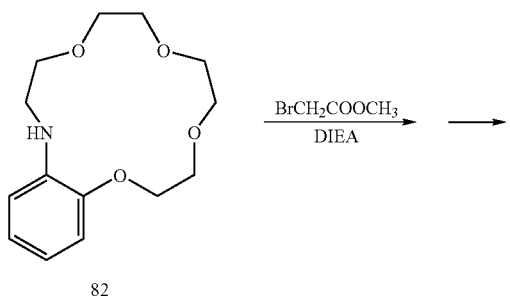

82

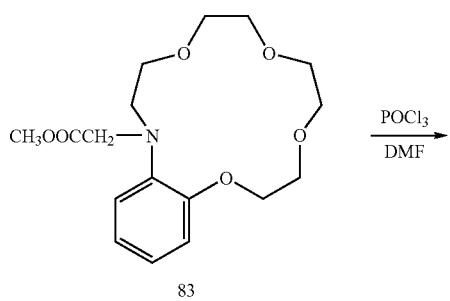

83

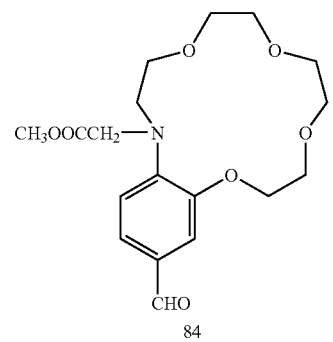

84

Example 78

Preparation of Compound 85 with a Fluorinated Xanthene as a DYE

A mixture of the aldehyde 84 (0.212 g, 0.58 mmol) and 4-fluororesorcinol (0.163 g, 1.27 mmol) in methanesulfonic acid (7 mL) is stirred for 24 h, then poured into 3N NaOAc (100 mL). The precipitated solid is filtered off, washed generously with water, and dried under vacuum to give compound 85 (0.229 g, 67%) as an off-white solid. Crude compound 85 is used in the next step without purification.

Example 79

Preparation of a Cell-Impermeable Metal Chelating Compound (Compound 86) with a Fluorinated Xanthene as a DYE A mixture of the dihydro compound 85 (0.117 g, 0.20 mmol) and freshly powdered chloranil (0.246 g, 1.00 mmol) in CHCl$_3$/MeOH 1:1 (10 mL) is vigorously stirred upon reflux for 3 h, then cooled down, filtered from the excess oxidizer and evaporated. The residue is purified by preparative TLC on silica gel, using MeOH/AcOH 5%:2% in CHCl$_3$ as eluant to give the compound 86 (0.046 g, 39%) as an orange solid.

Example 80

Preparation of a Cell-Permeable Metal Chelating Compound (Compound 87) with a Fluorinated Xanthene as a DYE To a solution of compound 86 (12 mg, 0.02 mmol) and DIEA (75 µL, 0.4 mmol) in DMF (1 mL), bromomethyl acetate (20 µL, 0.2 mmol) is added. The mixture is stirred for 3 h and evaporated at 1 mm Hg vacuum. The residue is purified by preparative TLC on silica gel, using MeOH/AcOH 7%:1% in CHCl$_3$ as eluant to give the compound 87 (12 mg, 96%) as an orange solid.

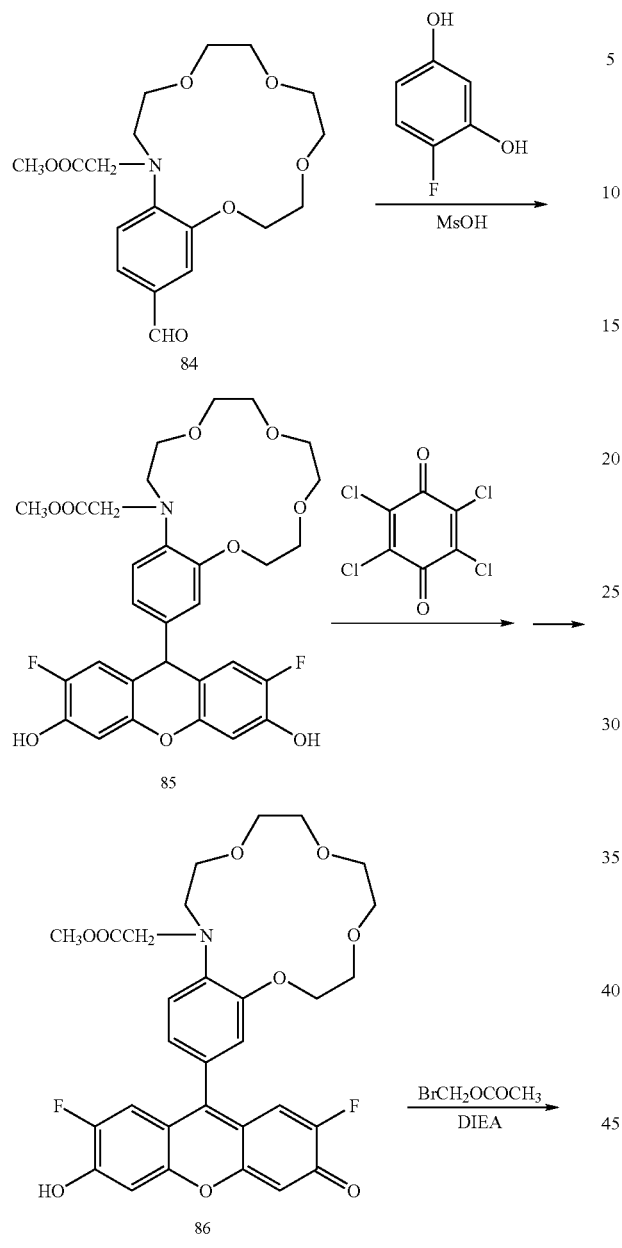

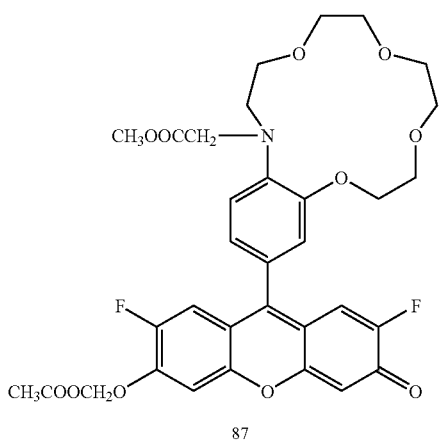

Example 81

Preparation of Metal Chelating Compound (Compound 89) with Tetramethylrosamine as DYE A mixture of aldehyde 844 (0.410 g, 1.11 mmol), and 3-(N,N-dimethylamino)phenol (0.337 g, 2.46 mmol), and TsOH (22 mg) in EtCOOH (11 mL) is stirred for 16 h at 65° C. The mixture is cooled down and poured into 3N NaOAc (100 mL). The resulting suspension is extracted with CHCl₃ (100+7×20 mL). The chloroform extract is filtered through paper and evaporated. The crude dihydro compound 88 is re-dissolved in MeOH/CHCl₃ 1:1 mixture (10 mL) and treated with chloranil (0.246 g, 1.00 mmol). The oxidation is continued upon vigorous stirring for 2 h, then the solvents are evaporated, the residue is re-dissolved in CHCl₃, and purified by column chromatography on silica gel (4×60 cm bed column, made with 5% MeOH+1% AcOH in CHCl₃) using (5–12.5%)MeOH/(1.0–1.3%) AcOH gradient as eluant to give the crude product, which is purified further by preparative TLC on silica gel, using 12% MeOH/3% ACOH in CHCl₃ as eluant to give compound 89 (0.038 g, 6%) as a dark red solid.

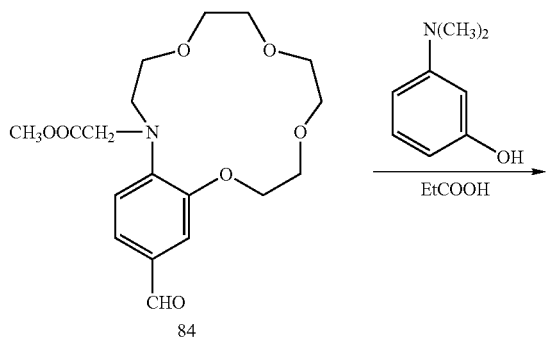

-continued

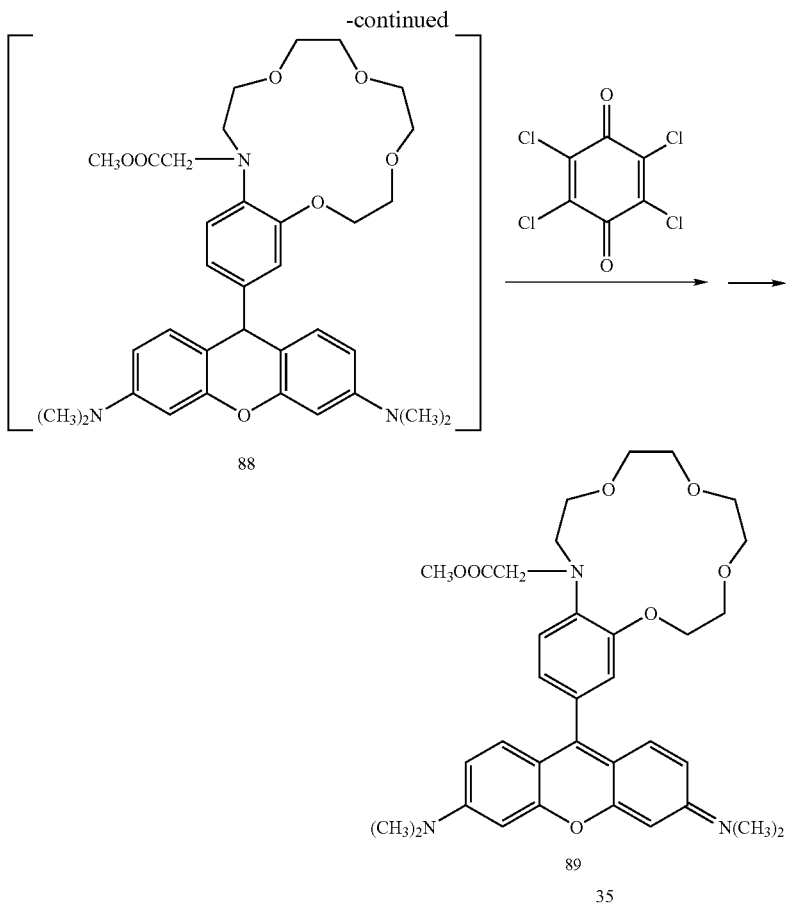

Example 82

Preparation of a Metal Chelating Compound (Compound 90) with a Borapolyazaindacene as a DYE To a stirred solution of aldehyde 84 (0.367 g, 1.0 mmol) in CH$_2$Cl$_2$ (40 ml) 2,4-dimethylpyrrole (0.25 mL, 2.4 mmol) is added, followed by TFA (0.09 mL, 1.2 mmol). The mixture is stirred for 20 h, diluted with CHCl$_3$ (200 mL) and washed with 2% Me$_4$NOH (2×200 mL), H$_2$O (200 mL). Tye chloroform layer is separated, filtered through paper filter and evaporated. The residue is co-evaporated with toluene (50 mL), re-dissolved in toluene (40 mL) and stirred 2 h with chloranil (0.296 g, 1.2 mmol). DIEA (1.7 mL, 10 mmol) is added, followed by BF$_3$OEt$_2$ (1.04 mL, 8 mmol) and the mixture is stirred for 20 h, filtered through Cellite, and evaporated. The residue is purified by column chromatography on silica gel (4×40 cm bed, made in 2% MeOH+1% AcOH in CHCl$_3$), using the same mixture as eluant to give compound 90 (0.169 g, 30%) as an orange solid.

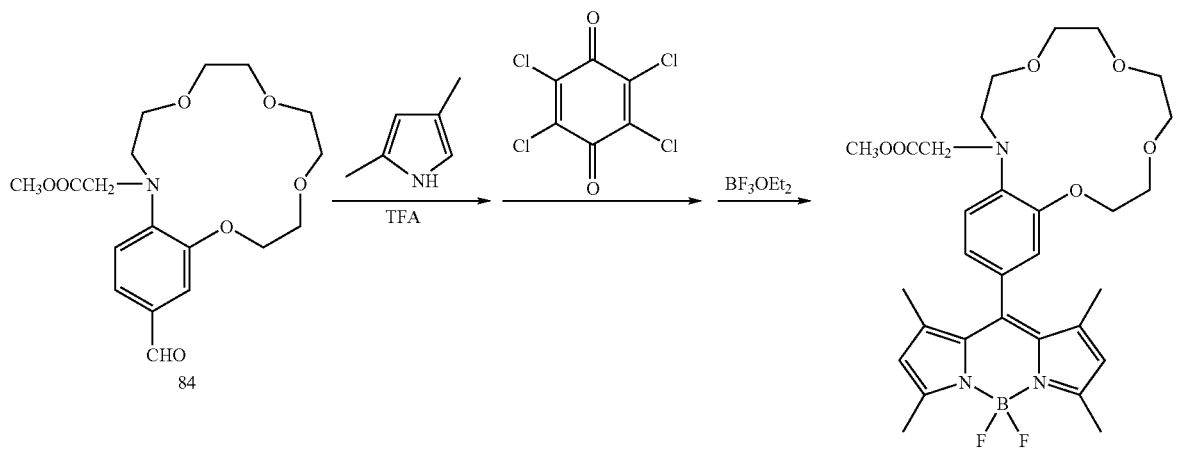

Example 83

Synthesis of an α-Nitrostilbene (Compound 92)

A mixture of aldehyde 84 (0.367 g, 1.0 mmol), Wittig salt 91 (0.804 g, 1.5 mmol), and $K_2CO_3$ (0.690 g, 5.0 mmol) in DMF (6 mL) is stirred for 7 h at 90° C., then left overnight at rt. The mixture is poured into $H_2O$ (200 mL), and the resulting suspension is extracted with $CHCl_3$ (200+10×20 mL). The extract is evaporated to dryness at 3 mm Hg and the residue is purified by column chromatography on silica gel (4×60 cm bed column, prepared in 4% MeOH in $CHCl_3$) using the same mixture of solvents as eluant to give stilbene 92 (0.530 g, 97%) as a dark red low-melting solid.

Example 84

Preparation of a Metal Chelating Compound (Compound 93) with Indole as a DYE

A solution of stilbene 92 (0.530 g, 0.97 mmol) in $P(OEt)_3$ (5 mL) is heated at 125° C. for 4 h, then evaporated. The residue is purified by column chromatography on silica gel (4×50 cm bed column, prepared in 5% MeOH in $CHCl_3$) using the same mixture of solvents as eluant to give compound 93 (0.171 g, 34%).

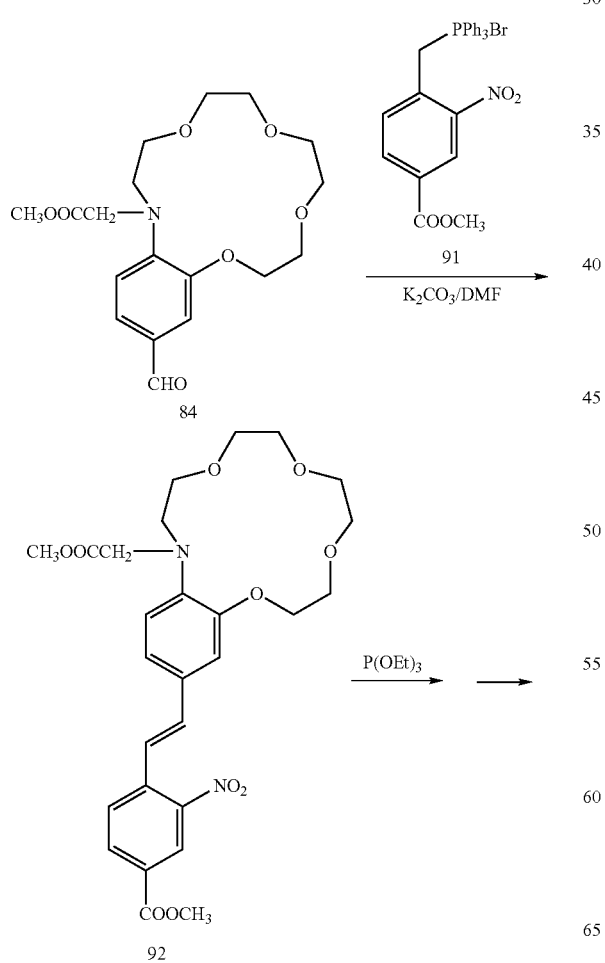

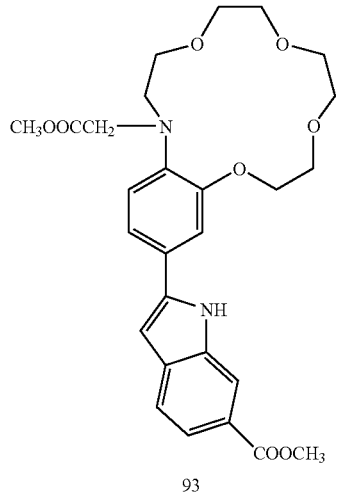

Example 85

Preparation of 15-Nitro-1-methoxycarbonylmethyl-1-aza-benzo-15-crown-5-ether (Compound 94)

To a stirred solution of crown ether 83 (0.420 g, 1.24 mmol) in $Ac_2O$ (10 mL), 65% $HNO_3$ (0.10 mL, 1.5 mmol) is introduced at 0° C. The mixture is stirred for 2 h at 0° C. and then poured into sat. $K_2CO_3$ (100 mL), and stirred for 1 h. The resulting solution is extracted with $CHCl_3$ (100+7×20 mL), the extract is filtered through paper and evaporated. The residue is purified by column chromatography on silica gel (4×60 cm bed column, prepared in $CHCl_3$) using $CHCl_3$ as eluant to give nitro derivative 94 (0.272 g, 57%) as a yellow-orange solid.

Example 86

Preparation of Azo-Dye Metal Chelating Compound (Compound 96)

A solution of crown ether 83 (0.339 g, 1.0 mmol) in dioxane (1 mL) and AcOH (1 mL) is treated with a solution of diazo compound 95, prepared from sulfanilic acid (0.190 g, 1.1 mmol) in 6 mL $H_2O$. The mixture is stirred for 3 h, poured into $H_2O$ (100 mL) and extracted with $CHCl_3$ (100+25×20 mL). The chloroform extract is evaporated, and the residue is purified by column chromatography on Sephadex LH-20 (3×35 cm bed column, prepared in $H_2O$) using $H_2O$ as eluant to give azo compound 96 (0.029 g, 7%) as a dark red solid.

Example 87

Preparation of 15-Amino-1-methoxycarbonylmethyl-1-aza-benzo-15-crown-5-ether (Compound 97)

A) A sample of nitro compound 94 (0.220 g, 0.57 mmol) is hydrogenated at 50 psi in DMF (25 mL) over 10% Pc/C (40 mg, catalyst) for 7 h. The mixture is filtered, and evaporated at 1 mm Hg. The residue is purified by preparative TLC on silica gel, using 20% MeOH in $CHCl_3$ as eluant to give the amine 97 (128 mg, 63%).

B) A sample of azo compound 96 (4 mg, 0.01 mmoL) in 0.5 ml ethanol is treated with sodium dithionite (10 mg, 0.06 mmol) in 0.2 ml water. The solvents are evaporated and the residue is washed with water to give amine 97 (3 mg, 85%), identical to that prepared in the above example.

Example 88

Preparation of Cell-Permeable Compound 98

To a stirred solution of the amine 97 (25 mg, 0.07 mmol) and DIEA (0.17 ml, 1 mmol) in $CH_2Cl_2$ (3 mL) an acid chloride, prepared from fluorinated xanthene acid (55 mg, 0.11 mmol) in $CH_2Cl_2$ (2 mL) is added dropwise. The mixture is stirred for 2 h and evaporated. The residue is purified by preparative TLC on silica gel, using 5% MeOH and 1% AcOH in $CHCl_3$ as eluant to give the compound 98 (32 mg, 63%) as an off-white solid.

Example 89

Preparation of Cell-Impermeable Compound 99

To a solution of the compound 98 (10 mg, 0.012 mmol) in MeOH (2 mL) an aqueous solution of $NH_3$ (0.5 mL) is added. The mixture is stirred for 30 min, evaporated to dryness, and the residue is suspended in water (2 mL), and centrifuged. The supernatant is discarded, and the solid is purified with preparative TLC on reverse-phase C18 plates, using 50% 2-PrOH and 0.2% TFA in $H_2O$ as eluant to give compound 99 (4 mg, 48%), as an orange solid.

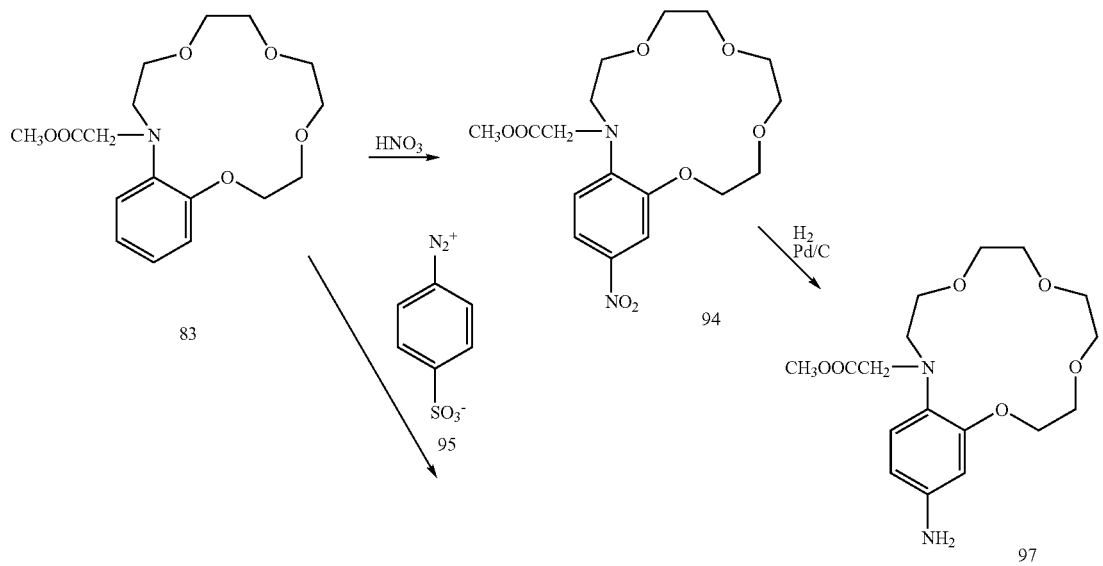

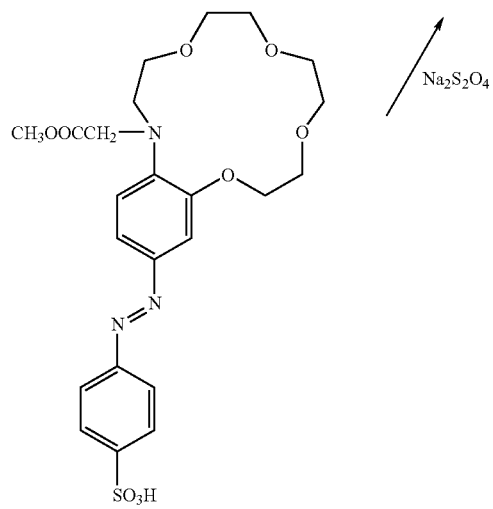

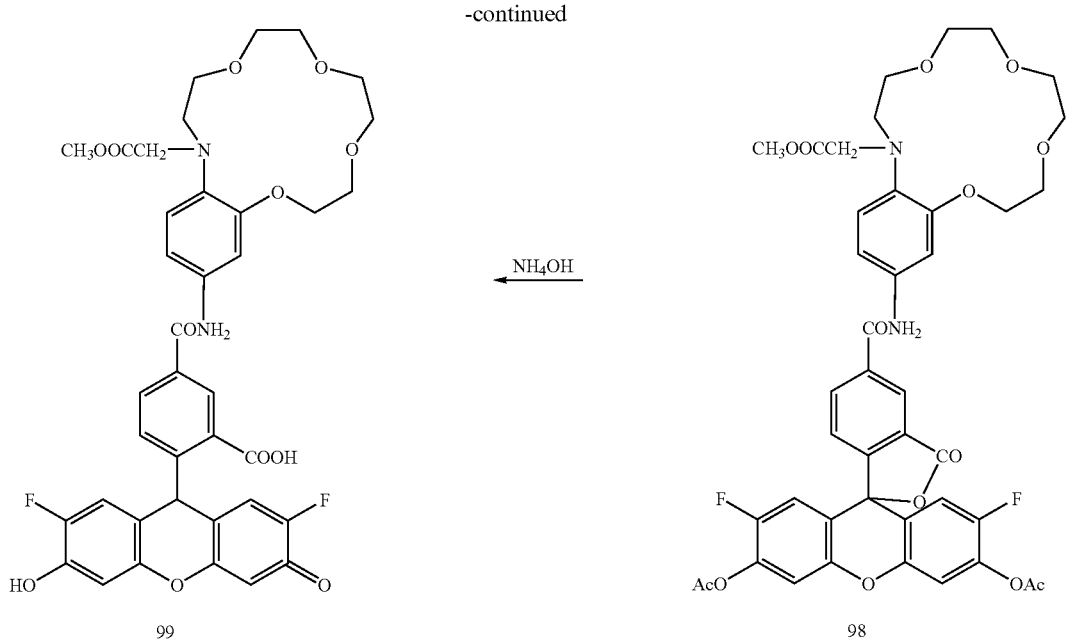

Example 90

Preparation of 1-Aza-benzo-14-crown-4 ether (Compound 100)

To a solution of 2-aminophenol 81 (1.322 g, 12 mmol) in MeCN (1 L), powdered CsF (7.300 g, 48 mmol) is added. The mixture is stirred vigorously for 1 h and then triethyleneglycol ditosylate (5.503 g, 12 mmol) in MeCN (50 mL) is introduced. The mixture is refluxed under $N_2$ atmosphere for 16 h and then evaporated. The residue is dissolved in $CHCl_3$ (500 mL), washed with $H_2O$, sat. $NaHCO_3$, $H_2O$, sat. NaCl (200 mL each), filtered trough paper, and evaporated. The residue is purified by column chromatography on silica gel (12×60 cm bed column, made in $CHCl_3$) using $CHCl_3$ as eluant to give crude product, which is purified by column chromatography on silica gel (12×60 cm bed column, made in 25% EtOAc in hexanes) using the same mixture of solvents as eluant to give compound 100, 0.370 g (14% yield) as an off-white solid.

Example 91

Preparation of 1-Methoxycarbonylmethyl-1-aza-benzo-12-crown-4-ether (Compound 101)

The mixture of compound 100 (0.360 g, 1.61 mmol), DIEA (0.56 mL, 3.22 mmol), methyl bromoacetate (0.76 mL, 8.05 mmol), and NaI (0.241 g, 1.61 mmol; catalyst) in MeCN (30 mL) is refluxed under $N_2$ atmosphere for 16 h, then cooled down and evaporated. The residue is redissolved in $CHCl_3$ (200 mL), washed with 1% AcOH (2×200 mL), $H_2O$ (200 mL). The chloroform solution is dried over $MgSO_4$, filtered through paper, and evaporated. The residue (TLC-pure crude product) is used in the next step without purification, considering it to be a 1.6 mmol quantity.

Example 92

Preparation of 13-Formyl-1-methoxycarbonylmethyl-1-aza-benzo-12-crown4-ether (Compound 102)

To a solution of the Vilsmeier reagent prepared from $POCl_3$ (0.75 mL, 8.0 mmol) in 8 mL DMF compound 101 (1.60 mmol) in DMF (2 mL) is introduced. The mixture is stirred under a $N_2$ atmosphere for 16 h, then poured into ice (20 g)/ sat. $K_2CO_3$ (50 mL) mixture. The mixture is extracted with $CHCl_3$ (100+6×10 mL); the extract is dried over $MagSO_4$, and evaporated. The crude product is purified by column chromatography on silica gel (1.5×30 cm bed column, made in $CHCl_3$) using $CHCl_3$ as eluant to give aldehyde 102, 0.285 g (55% yield on two steps) as an off-white solid.

Example 93

Preparation of Compound 103

A mixture of the aldehyde 102 (0.272 g, 0.88 mmol) and 4-fluoro resorcinol (0.248 g, 1.94 mmol) in MsOH (13 mL) is stirred for 24 h and then poured into 3N NaOAc (100 mL). The mixture is centrifuged, and the supernatant is discarded. The solid is washed with water, and dried in vacuum to give compound 103 (0.087 g, 18%) as an off-white solid. Crude compound 104 is used in the next step without purification.

Example 94

Preparation of Cell-Impermeable Compound 104

A mixture of the dihydro compound 85 (0.085 g, 0.16 mmol), and freshly powdered chloranil (0.197 g, 0.80 mmol) in $CHCl_3$/MeOH 1:1 mixture (6 mL) is vigorously stirred during reflux for 4 h, then cooled down, filtered from the excess oxidizer and evaporated. The residue is purified by preparative TLC on silica gel, using MeOH/AcOH 5%:2% in CHCl$_3$ as eluant to give the compound 104 (0.031 g, 36%) as an orange solid.

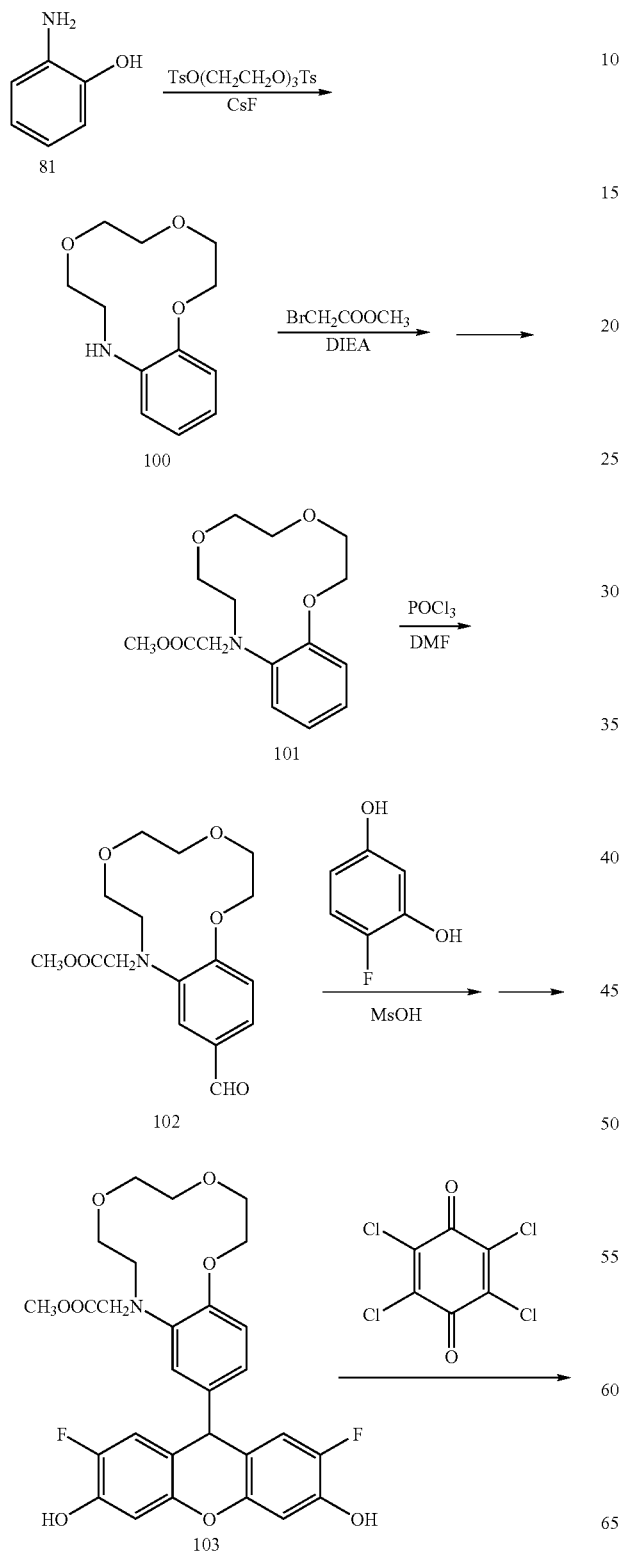

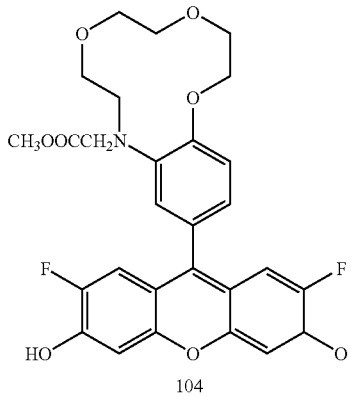

104

Example 95

Preparation of 1-Aza-benzo-18-crown-6 ether (Compound 105)

To a solution of 2-aminophenol 81 (1.090 g, 10 mmol) in MeCN (1 L), powdered CsF (6.080 g, 40 mmol) is added. The mixture is stirred vigorously for 1 h and then pentaethylene glycol ditosylate (5.500 g, 11 mmol) in MeCN (50 mL) is introduced. The mixture is refluxed under N$_2$ atmosphere for 70 h and then evaporated. The residue is dissolved in CHCl$_3$ (600 mL), washed with H$_2$O, sat. NaHCO$_3$, H$_2$O, and sat. NaCl (200 mL each). The chloroform solution is dried over MgSO$_4$, filtered trough paper, and evaporated. The residue is purified by column chromatography on silica gel (8×45 cm bed column, made in CHCl$_3$) using 0–1.2% MeOH gradient in CHCl$_3$ as eluant to give compound 105, 0.681 g (22% yield) as a off-white solid.

Example 96

Preparation of 1-Methoxycarbonylmethyl-1-azabenzo-18-crown-6-ether (Compound 126)

A mixture of compound 105 (0.670 g, 2.15 mmol), DIEA (0.72 mL, 4.15 mmol), methyl bromoacetate (1.01 mL, 10.75 mmol), and NaI (0.322 g, 2.15 mmol; catalyst) in MeCN (40 mL) is refluxed under a N$_2$ atmosphere for 16 h, then cooled down and evaporated. The residue is redissolved in CHCl$_3$ (200 mL), washed with 1% ACOH (2×200 mL), H$_2$O (200 mL). Chloroform solution is dried over MgSO$_4$, filtered trough paper, and evaporated. The residue is purified by column chromatography on silica gel (3×30 cm bed column, made in CHCl$_3$) using 2.5–4% MeOH gradient in CHCl$_3$ as eluant to give compound 106, 0.430 g (52% yield) as an off-white solid.

Example 97

Preparation of 18-Formyl-1-methoxycarbonylmethyl-1-aza-benzo-18-crown-6-ether (Compound 107)

To a solution of the Vilsmeier reagent prepared from POCl$_3$ (1.23 mL, 13.2 mmol) in 6 mL DMF compound 106

(0.410 g, 1.32 mmol) in DMF (2 mL) is introduced. The mixture is stirred under a N₂ atmosphere for 16 h, then poured into ice (40 g)/sat. K₂CO₃ (100 mL) mixture. The mixture is extracted with CHCl₃ (5×100 mL), the extract is dried over MagSO₄, and evaporated. The crude product is treated with cold ether (10 mL), and the precipitated solid is collected to give aldehyde 107, 0.246 g (45% yield) as a white solid.

Example 98

Preparation of Compound 108

A mixture of the aldehyde 107 (0.236 g, 0.57 mmol) and 4-fluoro resorcinol (0.186 g, 1.45 mmol) in MsOH (8 mL) is stirred for 16 h, then poured into 3N NaOAc (100 mL). The precipitate is filtered, washed with water, and dried in vacuum to give compound 108 (0.350 g, 97%) as an off-white solid. Crude compound 108 is used in the next step without purification.

Example 99

Preparation of Cell-Impermeable Compound 109

A mixture of the dihydro compound 108 (0.350 g, 0.56 mmol), and freshly powdered chloranil (0.701 g, 2.85 mmol) in CHCl₃/MeOH 1:1 mixture (25 mL) is vigorously stirred upon reflux for 4 h, then cooled down, filtered from the excess oxidizer and evaporated. The residue is purified by column chromatography on silica gel, (4×40 cm bed column, made in 10% MeOH+1% ACOH in CHCl₃) using the same mixture of solvents as eluant to give the compound 109 (0.088 g, 25%) as an orange solid.

Example 100

Preparation of Cell-Permeable Compound 110

To a solution of compound 109 (32 mg, 0.05 mmol) and DIEA (0.17 mL, 1.0 mmol) in DMF (2 mL), bromomethyl acetate (50 □L, 0.5 mmol) is added. The mixture is stirred for 3 h and evaporated at 1 mm Hg vacuum. The residue is purified by preparative TLC on silica gel, using MeOH/AcOH 15%:1% in CHCl₃ as eluant to give the compound 110 (20 mg, 57%) as an orange solid.

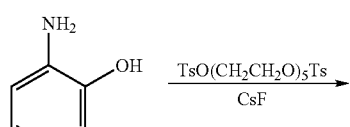

81

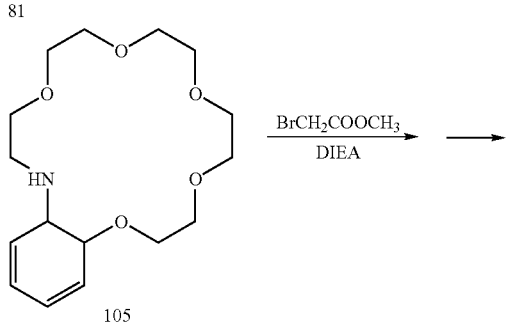

105

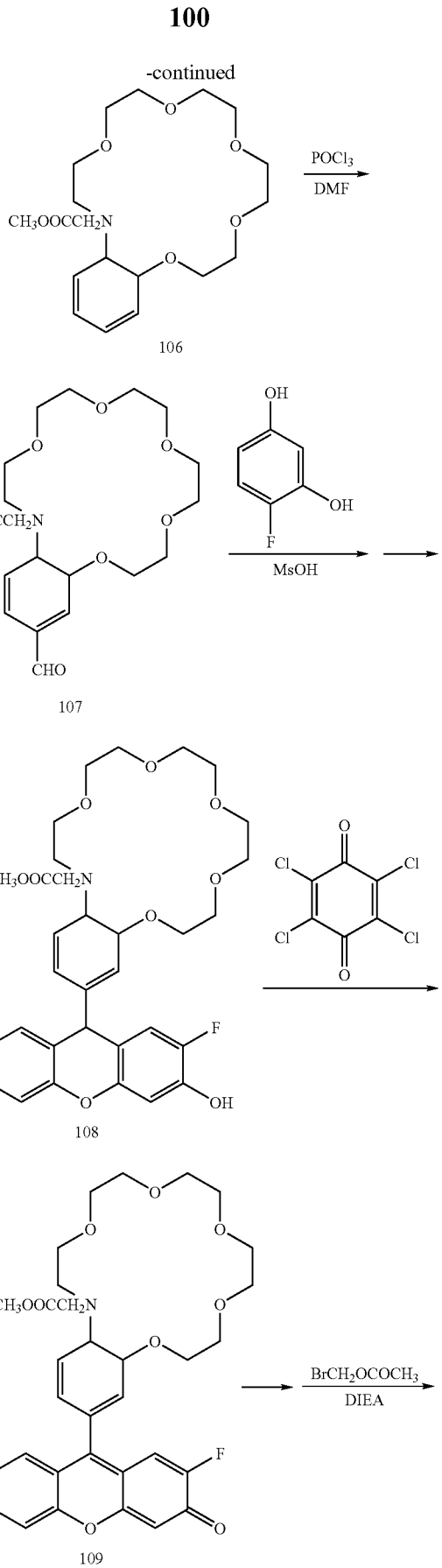

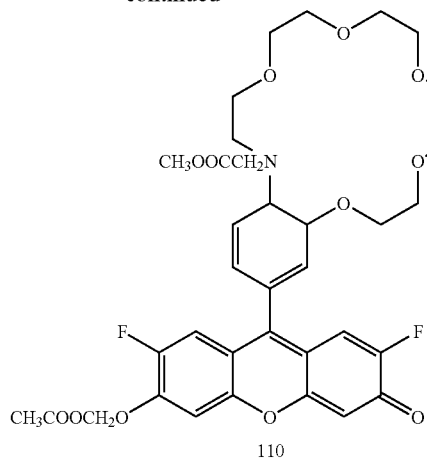

110

Example 101

Preparation of 1-(2'-Methoxyacetyl)-1-aza-benzo-15-crown-5 ether (Compound 111)

To a stirred solution of the crown ether 82 (6.20 g, 23 mmol) and Et$_3$N (9.3 mL, 70 mmol) in CH$_2$Cl$_2$ (250 mL) a methoxyacetyl chloride (3.2 mL, 35 mml) in CH$_2$Cl$_2$ (15 mL) is introduced within 15 min. The mixture is stirred for 3 h, diluted with CHCl$_3$ (150 mL), and washed with H$_2$O, 1% ACOH, H$_2$O, sat. NaHCO$_3$, H$_2$O (200 mL each), filtered through paper filter and evaporated. The residue is purified by column chromatography on silica gel (6×45 cm bed column, made in CHCl$_3$), using 2.5% MeOH in CHCl$_3$ as eluant to give compound 111 (4.25 g, 55%) as a yellow oil.

Example 102

Preparation of 1-(2'-Methoxyethyl)-1-aza-benzo-15-crown-5 ether (Compound 112)

A) To a stirred solution of compound 111 (4.25 g, 12.5 mmol) in dry THF (50 mL) a 1 N diborane in THF (50 mL, 50 mmol) is added. The mixture is stirred under reflux for 20 h, decomposed by dropwise addition of MeOH (50 mL), and evaporated. The residue is co-eveporated with MeOH (5×100 mL) to remove boron complexes, and dried in vacuo to give compound 112 (4.05 g, 99%) as a colorless oil.

B) A mixture of compound 82 (1.20 g, 4.50 mmol), DEIA (1.6 mL, 9.0 mmol), 2-bromoethylmethyl ether (4.2 mL, 45 mmol), NaI (0.68 g, 4.50 mmo, catalyst) in MeCN (200 mL) is stirred under reflux for 70 h. More DIEA (1.6 mL, 9.0 mmol) and 2-bromoethylmethyl ether (4.2 mL, 45 mmol) are added and heating continued for another 40 h. The reaction mixture is evaporated, the residue is re-dissolved in CHCl$_3$ (300 mL), washed with 1% AcOH (3×200 mL), H$_2$O (200 mL), filtered through paper filter and evaporated. The residue is purified by column chromatography on silica gel (3×40 cm bed column, made in 2.5% MeOH in CHCl$_3$), using the same mixture of solvents as eluant to give compound 112 (0.080 g, 5%), identical to that prepared section A of this example.

Example 103

Preparation of 1-(2'-Methoxyethyl)-15-formyl-1-aza-benzo-15-crown-5 ether (Compound 113)

To a solution of the Vilsmeier reagent prepared from POCl$_3$ (12 mL, 125 mmol) in 70 mL DMF compound 112 (4.05 g, 12.5 mmol) in DMF (10 mL) is introduced. The mixture is stirred under N$_2$ atmosphere for 16 h at 40° C., then more Vilsmeier reagent from POCl$_3$ (12 mL, 125 mmol) in 70 mL DMF is added and the stirring continued for another 24 h. The mixture is poured into ice (400 g)/sat. K$_2$CO$_3$ (400 mL) mixture. The mixture is extracted with CHCl$_3$ (300+6×50 mL), the extract is dried over MagSO$_4$, and evaporated. The crude product is purified by column chromatography on silica gel (6×50 cm bed column, made in CHCl$_3$) using 1.5% MeOH in CHCl$_3$ as eluant to give aldehyde 113, 1.613 g (36% or, 58% based on recovery), then eluant is changed to 10% to recover starting material (1.49 g, 37%).

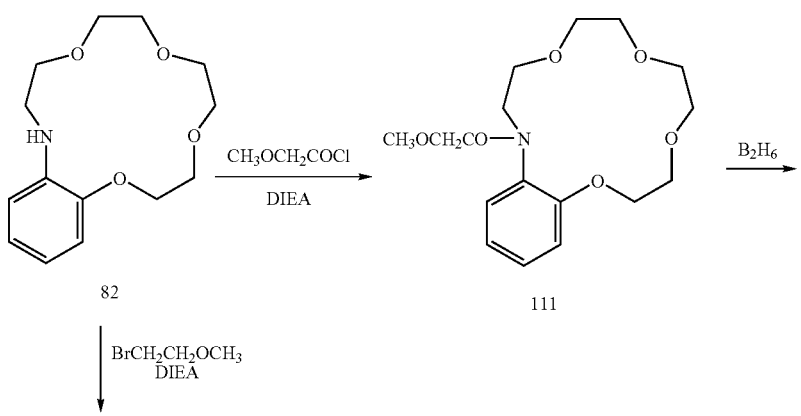

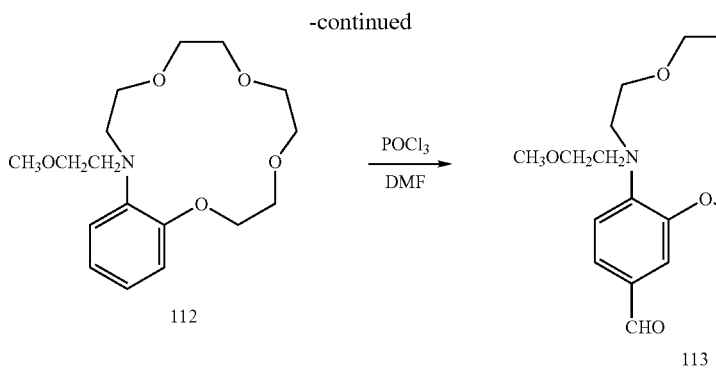

Example 104

Preparation of Compound 114

A mixture of the aldehyde 113 (0.700 g, 1.98 mmol) and 4-fluororesorcinol (0.558 g, 4.36 mmol) in methanesulfonic acid (30 mL) is stirred for 24 h and poured into 3N NaOAc (300 mL). The mixture is extracted with n-BuOH (7×50 mL). The extract is evaporated to give the crude dihydro derivative 114. Crude compound 114 is used in the next step without purification, considering it as 1.8 mmol.

Example 105

Preparation of Cell-Impermeable Compound 115

A mixture of the dihydro compound 114 (1.8 mmol), and freshly powdered chloranil (2.210 g, 9.00 mmol) in CHCl$_3$MeOH 1:1 mixture (100 mL) is vigorously stirred upon reflux for 4 h, then cooled down, filtered from the excess oxidizer and evaporated. The residue is purified by column chromatography on silica gel (6×55 cm bed column, made in 10% MeOH+1% AcOH in CHCl$_3$), using 10–15% MeOH gradient in CHCl$_3$+1% ACOH as eluant to give the compound 115 (0.189 g, 18% for two steps) as a brown solid.

Example 106

Preparation of Cell-Permeable Compound 116

To a solution of compound 115 (28 mg, 0.05 mmol) and DIEA (0.17, 1.0 mmol) in DMF (2 mL), bromomethyl acetate (50 μL, 0.5 mmol) is added. The mixture is stirred for 1 h and evaporated at 1 mm Hg vacuum. The residue is purified by preparative TLC on silica gel, using MeOH/AcOH 10%:2% in CHCl$_3$ as eluant to give the compound 116 (4 mg, 12%) as an orange solid.

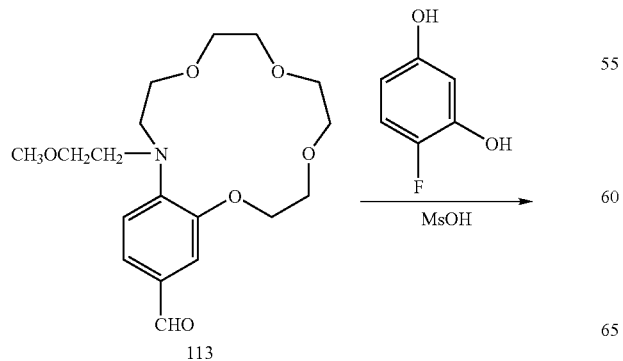

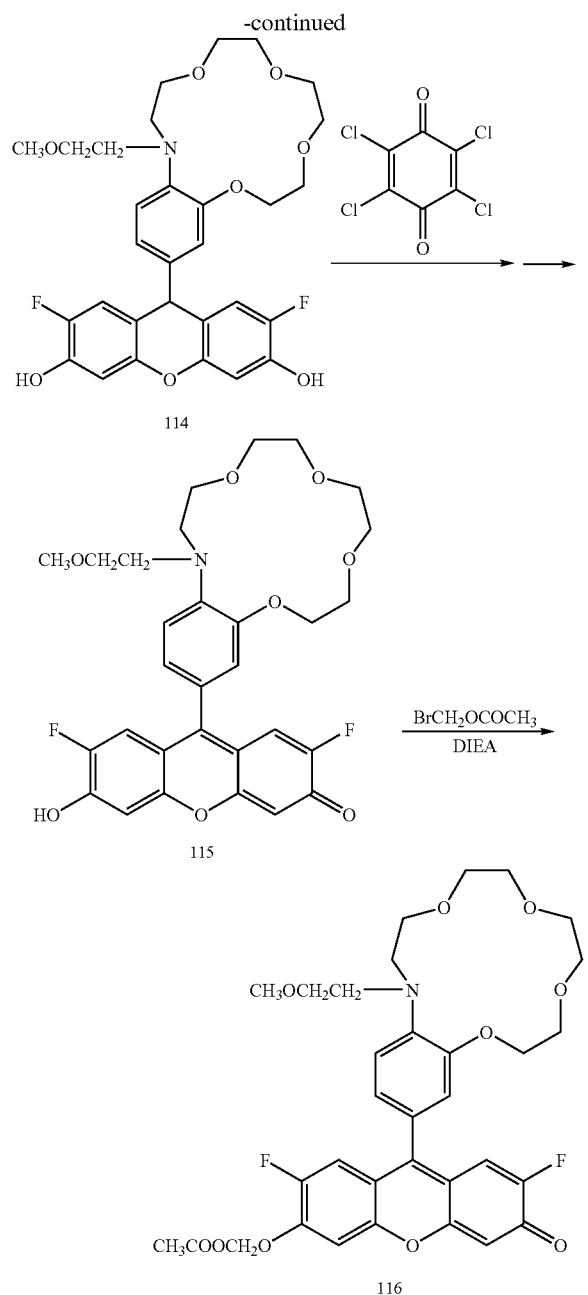

Example 107

Preparation of Tetramethylrosamine Compound 118

A mixture of aldehyde 113 (0.900 g, 2.55 mmol), and 3-(N,N-dimethylamino)phenol (0.769 g, 5.61 mmol), and TsOH (50 mg, catalyst) in EtCOOH (25 mL) is stirred for 16 h at 65° C. The mixture is cooled down and poured into 3N NaOAc (500 mL). The resulting suspension is extracted with CHCl₃ (200+7×30 mL). The extract is filtered through paper and evaporated. The resulting crude dihydro compound 117 is re-dissolved in MeOH/CHCl₃ 1:1 mixture (100 mL) and treated with chloranil (0.541 g, 2.20 mmol). The oxidation is continued upon vigorous stirring for 2 h, then the solvents are evaporated, the residue is re-dissolved in CHCl₃, and purified by column chromatography on silica gel (8×50 cm bed column, made with 5% MeOH+1% ACOH in CHCl₃) using 5–20% MeOH gradient in CHCl₃+1.0% ACOH as eluant to give compound 118 (0.236 g, 16% on two steps) as a dark red solid.

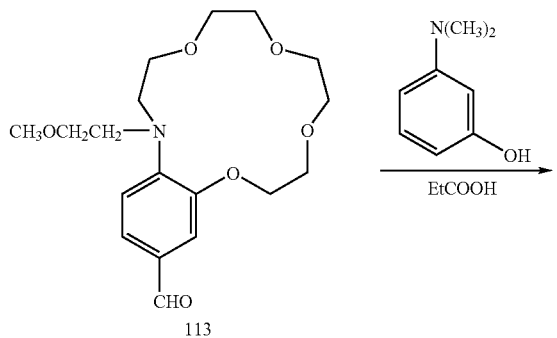

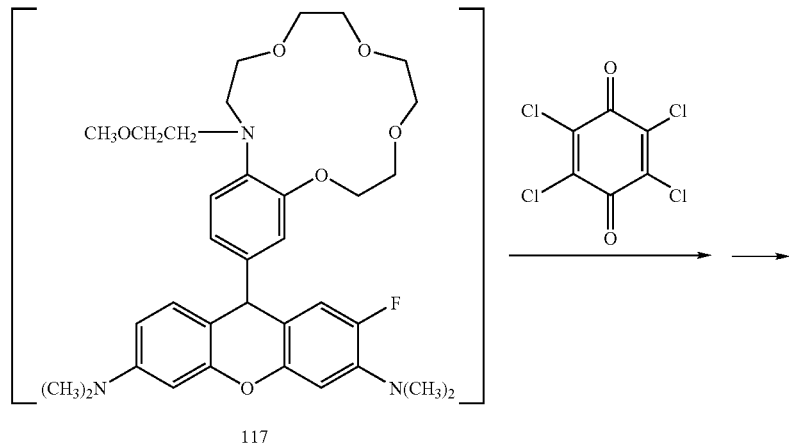

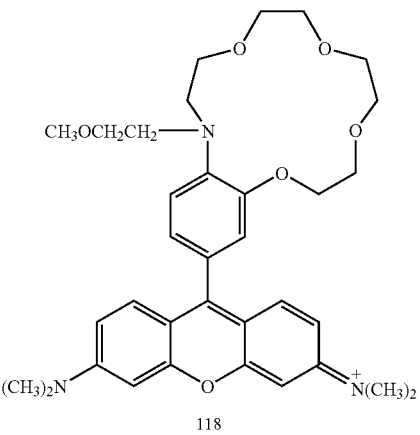

Example 108

Synthesis of an α-Nitrostilbene (Compound 119)

A mixture of aldehyde 113 (0.172 g, 0.49 mmol), Wittig salt 91 (0.392 g, 0.73 mmol), and K$_2$CO$_3$ (0.338 g, 2.45 mmol) in DMF (3 mL) is stirred for 6 h at 90° C., then left overnight at rt. The mixture is poured into H$_2$O (200 mL), and the resulting suspension is extracted with CHCl$_3$ (50+ 7×20 mL). The extract is evaporated to dryness at 3 mm Hg and the residue is purified by column chromatography on silica gel (2.5×30 cm bed column, prepared in 3% MeOH in CHCl$_3$) using the same mixture of solvents as eluant to give stilbene 119 (0.195 g, 75%) as a dark red low-melting solid.

Example 109

Preparation of Compound 120

A solution of stilbene 119 (0.190 g, 0.36 mmol) in P(OEt)$_3$ (3 mL) is heated at 125° C. for 4 h, then evaporated. The residue is purified by column chromatography on silica gel (2.5×50 cm bed column, prepared in 5% MeOH and 1% ACOH in CHCl$_3$) using the same mixture of solvents as eluant to give compound 120 (0.099 g, 55%) as an off-white solid.

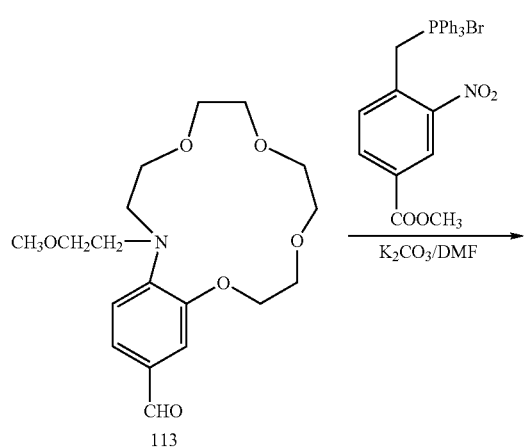

113

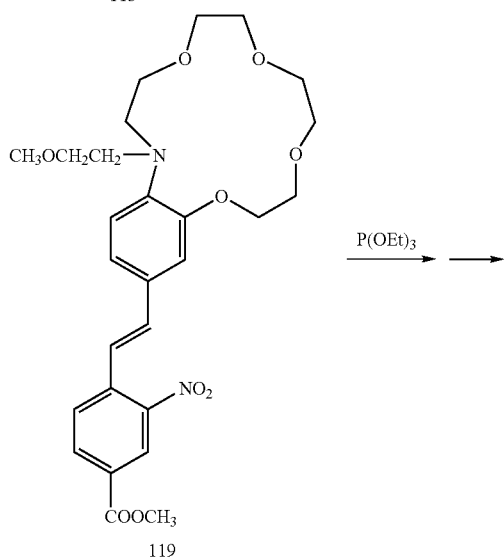

119

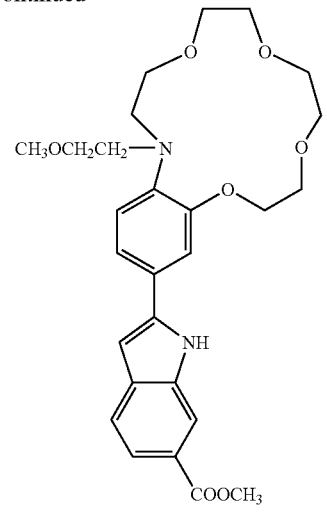

120

Example 110

Preparation of 1-Ethoxyoxalyl-1-aza-benzo-15-crown-5-ether (Compound 121)

To a mixture of compound 82 (1.345 g, 5.00 mmol) and Et$_3$N (1.4 mL, 10.00 mmol) in CH$_2$Cl$_2$ (30 mL), ethyl oxalylchloride (0.84 mL, 7.50 mmol) in CH$_2$Cl$_2$ (5 mL) is added dropwise. The mixture is stirred for 1 h, diluted with CHCl$_3$ (200 mL), washed with 1% ACOH (3×100 mL), H$_2$O (100 mL), sat. NaHCO$_3$ (2×100 mL), sat. NaCl (200 mL). The chloroform fraction is dried over MgSO$_4$ and evaporated. The residue is purified by column chromatography on silica gel (4×30 cm bed, made in 30% EtOAc in hexanes), using 30–60% EtOAc gradient in hexanes as eluant to give compound 121 (1.170 g, 65% yield) as a yellow oil.

Example 111

Preparation of 1-(N,N-Dimethylaminooxalyl)-1-aza-benzo-15-crown-5-ether (Compound 122)

To a solution of the compound 121 (0.734 g, 2.00 mmol) in MeOH (15 mL), a solution of dimethylamine (2 mL, 40 mmol) in cold MeOH (15 mL) is added upon cooling to 0° C. The mixture is heated to 30° C. for 16 h, then cooled to 0° C. and a new portion of dimethylamine (2 mL, 40 mmol) is introduced. The mixture is stirred for 3 h at 30° C. and then evaporated and the residue is treated with cold ether. The precipitated solid is filtered off, and washed with ether to give compound 122 (0.542 g, 74% yield) as a white solid.

Example 112

Preparation of 1-(2'-N,N-Dimethylaminoethyl)-1-aza-benzo-15-crown-5-ether (Compound 123)

To the solution of compound 122 (0.440 g, 1.20 mmol) in THF (10 ml) a solution of 1 N diborane in THF (12 mL, 12 mml) is added. The mixture is refluxed for 16 h, then decomposed by careful addition of MeOH (30 mL), evaporated, and co-evaporated with MeOH (5×50 mL) to remove boron complexes. The crystalline residue of the compound 123 (0.405 g, 100% yield) is used in next step without purification.

Example 113

Preparation of 1-(2'-N,N-Dimethylaminoethyl)-15-formyl-1-aza-benzo-15crown-5-ether (Compound 124)

To a solution of the Vilsmeier reagent prepared from $POCl_3$ (1.5 mL, 16.0 mmol) in 5 mL DMF, compound 123 (0.550 g, 1.62 mmol) in DMF (2 mL) is introduced. The mixture is stirred under $N_2$ atmosphere for 16 h, then poured into ice (20 g)/sat. $K_2CO_3$ (50 mL) mixture. The mixture is extracted with $CHCl_3$ (100+7×25 mL), the extract is dried over $MagSO_4$, and evaporated. The crude product is purified by column chromatography on silica gel (3×35 cm bed column, made with 3% MeOH in $CHCl_3$) using the same mixture of solvents as eluant to give aldehyde 124, (0.175 g 30% yield) as a yellow low-melting solid.

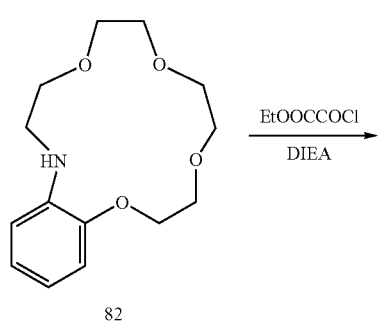

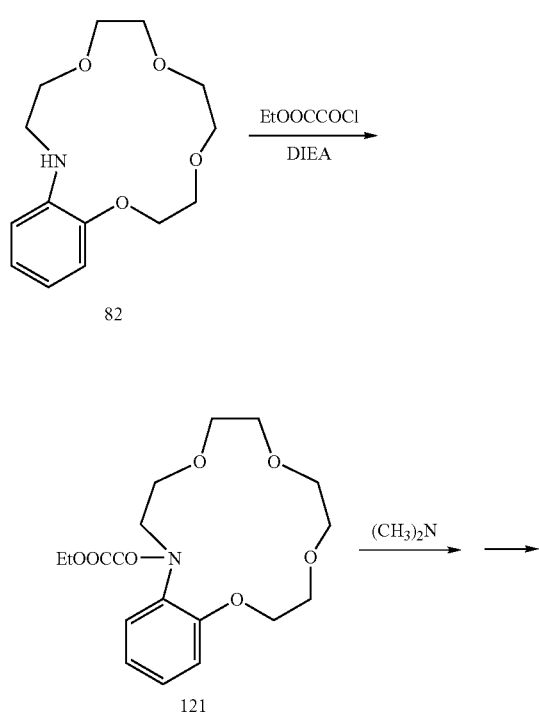

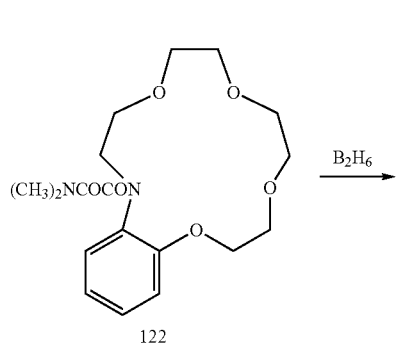

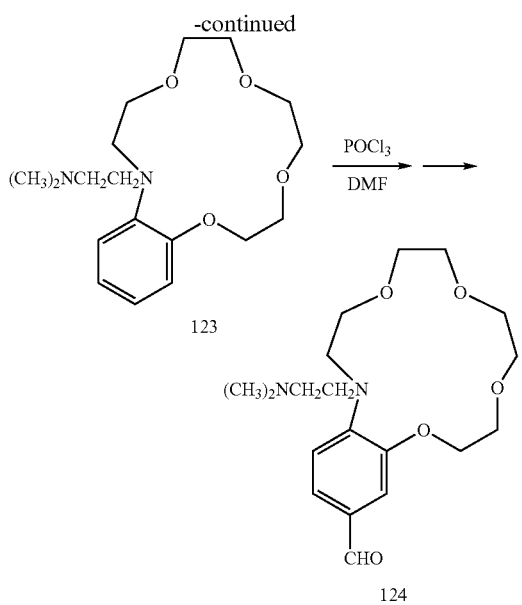

Example 114

Synthesis of α-Nitrostilbene (Compound 125)

A mixture of aldehyde 124 (0.070 g, 0.19 mmol), Wittig salt 91 (0.154 g, 0.29 mmol), and $K_2CO_3$ (0.131 g, 0.95 mmol) in DMF (2 mL) is stirred for 16 h at 90° C. The mixture is diluted with $CHCl_3$ (10 mL), filtered from inorganic materials and evaporated to dryness at 3 mm Hg. The residue is purified by preparative TLC on silica gel using 20% MeOH and 5% ACOH in $CHCl_3$ as eluant to give stilbene 125 (0.060 g, 58%) as a dark red solid.

Example 115

Preparation of Compound 126

A solution of stilbene 119 (0.055 g, 0.01 mmol) in $P(OEt)_3$ (2 mL) is heated at 125° C. for 14 h, then evaporated. The residue is purified by preparative TLC on silica gel using 25% MeOH and 5% AcOH in $CHCl_3$ as eluant to give compound 126 (0.029 g, 57%) as an off-white solid.

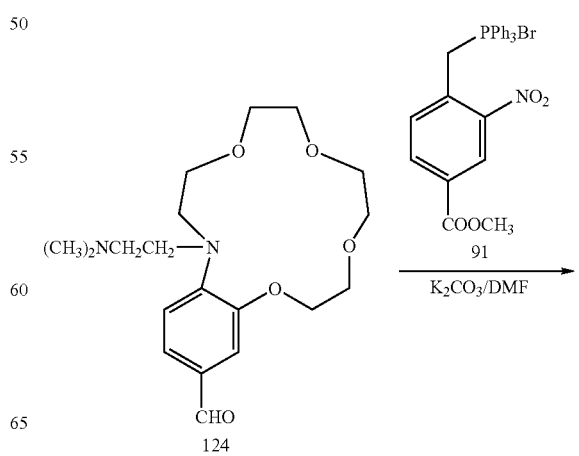

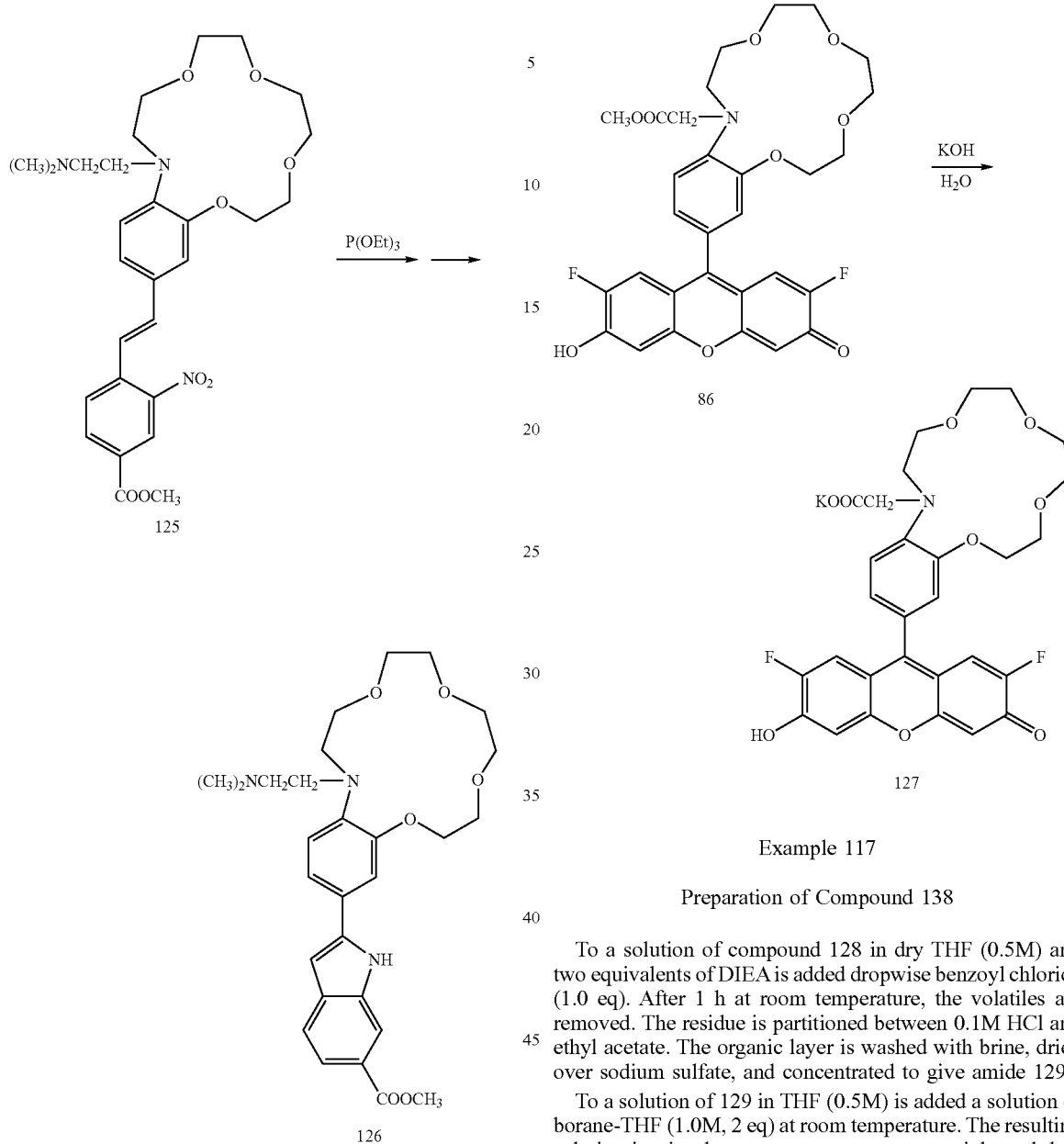

Example 116

Hydrolysis of Compound 86

To a solution of the compound 86 (0.032 g, 0.055 mmol) in 50% MeOH (2 mL), 1N KOH (0.16 mL, 16 mml) is added. The mixture is stirred for 16 h, diluted with H₂O, and 0.2 N HCl is added to achieve pH=8.0. The resulting solution is filtered through a nylon membrane filter and evaporated. The crude product is purified by column chromatography on Sephadex LH-20 (2.6×50 cm bed column, made with $H_2O$), using $H_2O$ as eluant to give compound 127 (0.021 mg, 59% yield) as a brown solid.

Example 117

Preparation of Compound 138

To a solution of compound 128 in dry THF (0.5M) and two equivalents of DIEA is added dropwise benzoyl chloride (1.0 eq). After 1 h at room temperature, the volatiles are removed. The residue is partitioned between 0.1M HCl and ethyl acetate. The organic layer is washed with brine, dried over sodium sulfate, and concentrated to give amide 129.

To a solution of 129 in THF (0.5M) is added a solution of borane-THF (1.0M, 2 eq) at room temperature. The resulting solution is stirred at room temperature over night and then methanol (2 eq) is carefully added. The volatiles are removed in vacuo, and the residue partitioned between water and ethyl acetate. The organic layer is dried over sodium sulfate and concentrated to give aniline 130, which is purified further if necessary by flash chromatography on silica gel using ethyl acetate in hexanes.

To a solution of 130 (0.05M) in dry THF with 2 eq DIEA is slowly added a 0.1M solution of diglycolyl chloride in dry THF with rapid stirring. After 2 h, the reaction solution is concentrated in vacuo. The residue is partitioned between 0.1M HCl and ethyl acetate. The organic layer is washed with brine, dried over sodium sulfate, and concentrated to give bisamide 131.

To a 0.1M solution of 131 in dry THF is slowly added borane-THF (1.0M, 5 eq). The resulting solution is stirred at room temperature overnight and then methanol (5 eq) is added. The resulting mixture is concentrated in vacuo, and the residue partitioned between water and ethyl acetate. The organic phase is washed with brine and dried over sodium sulfate, and concentrated in vacuo to give the diol 132, which is purified further if necessary by flash chromatography on silica gel using methanol in chloroform.

A solution of 132 is dissolved in dry acetonitrile to 0.5M. The resulting solution is treated with methanesulfonyl chloride (1.2 eq) and cesium carbonate (2 eq). The resulting mixture is stirred at reflux for 6 hours, then cooled and filtered and concentrated in vacuo. The desired azacrown ether 133 is formed as a minor product, isolated from the residue by flash chromatography on silica gel using ethyl acetate in hexanes.

The crown 133 is stirred in ethyl acetate (0.5M) with 10 wt % Pd/C (cat.) under 30 psi hydrogen gas for 6 hours. After filtration, the reaction solution is concentrated in vacuo to give aniline 134.

To a solution of 134 in DMF (0.5M) is added methyl bromoacetate (5 eq) and DIEA (3 eq). The resulting solution is stirred at 90° C. overnight, then cooled and concentrated. The residue is partitioned between 0.1M HCl and ethyl acetate. The organic layer is washed with brine and dried over sodium sulfate, then concentrated in vacuo to give crown 135, which is purified further if necessary by flash chromatography on silica gel using ethyl acetate in hexanes.

To a solution of Vilsmeyer reagent made from 2 eq phosphorous oxychloride in DMF is added a solution of 135 in DMF. The resulting solution is stirred at room temperature overnight, then poured into aq. sodium bicarbonate. The resulting mixture is extracted with ethyl acetate. The extract is washed with water and brine, dried over sodium sulfate, and concentrated in vacuo to give aldehyde 136, which is purified further if necessary by crystallization from methanol.

To a solution of 136 in methanesulfonic acid (0.5M) is added 4-fluororesorcinol (2 eq). The resulting solution is stirred at room temperature 15 minutes, then poured carefully into 3M aqueous NaOAc. The resulting precipitate is collected by suction filtration, rinsed with water, and dried in vacuo to give dihydro compound 137 as a pale brown powder.

A solution of 137 in methanol/chloroform (1:1, 0.5M) is treated with 2 eq of para-chloranil. The resulting mixture is stirred at room temperature overnight, then filtered and concentrated. The residue is purified by chromatography on silica gel using methanol in chloroform to give indicator 138 as a dark orange powder.

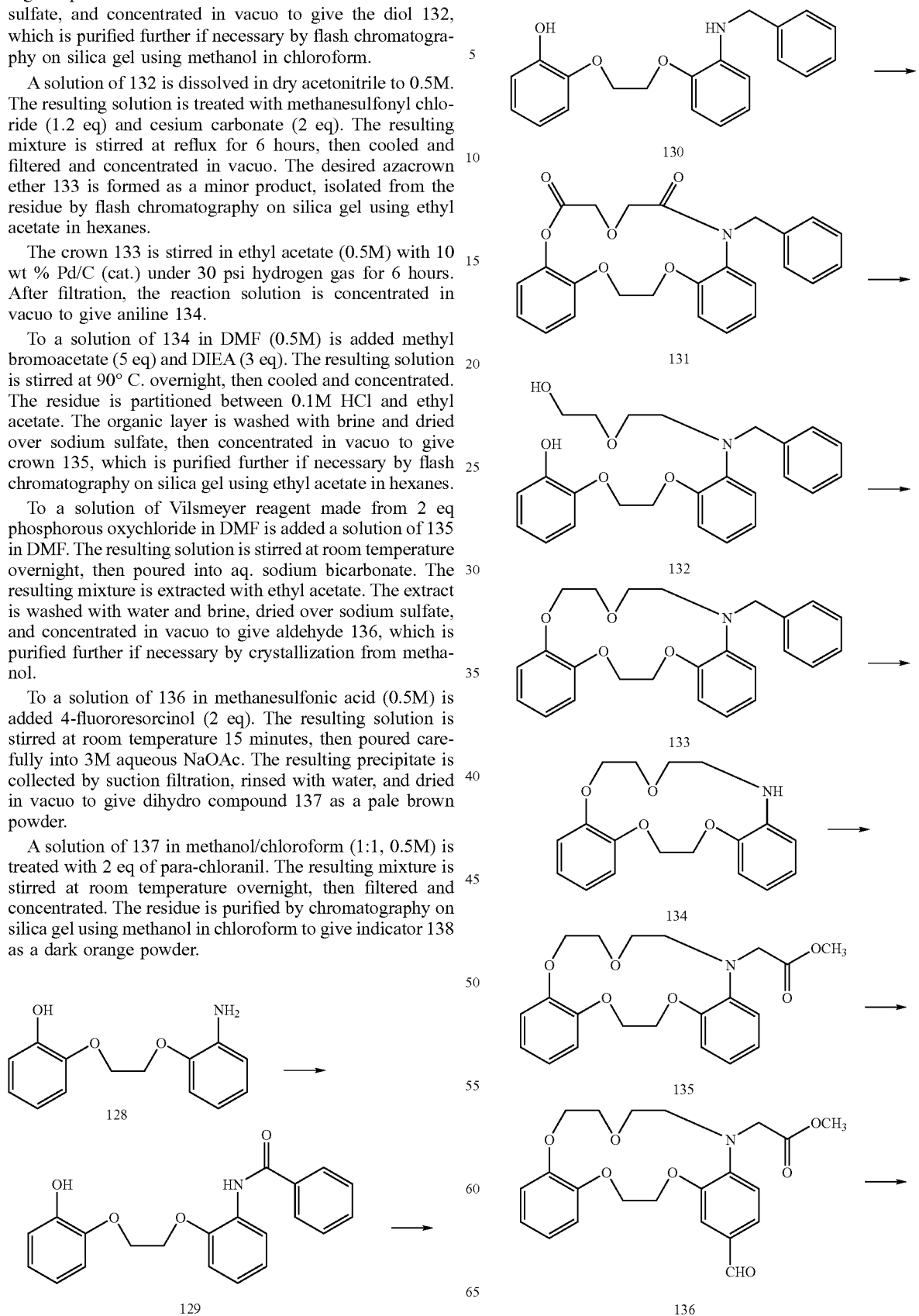

-continued

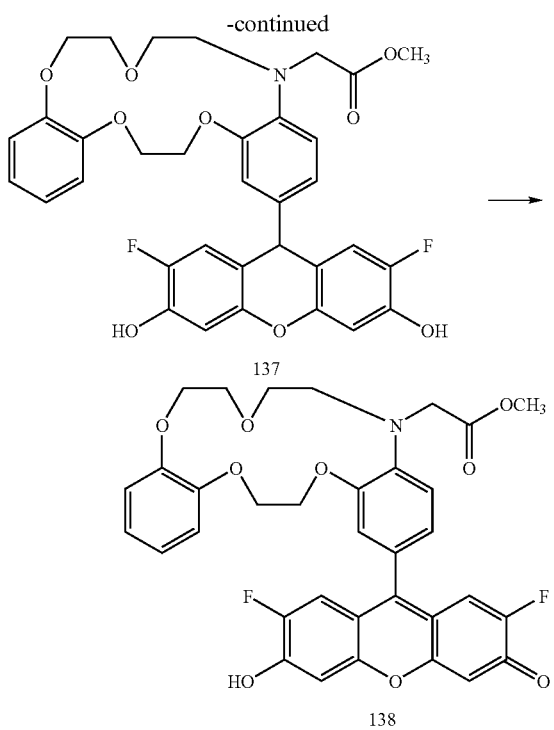

137

138

Example 118

Synthesis of Compound 140

A 0.5M solution of compound 86 in 1:1 methanol/dioxane is treated at room temperature with 5 equivalents of tetrabutylammonium hydroxide. After 2 hours the volatiles are removed in vacuo and the residue is dissolved in water. The pH is lowered to 2.0 by dropwise addition of aqueous HCl. The resulting precipitate is collected by filtration and dried in vacuo to give carboxylic acid 139. A 0.5M solution of compound 139 in dry DMF is treated with 1.5 equivalents of O—(N-succinimidyl)-N,N,N',N'-tetramethyluronium tetrafluoroborate. After 2 hours the reaction soluted is diluted 10× with diethyl ether. The resulting precipitate is collected by filtration to give reactive succinimidyl ester compound 140.

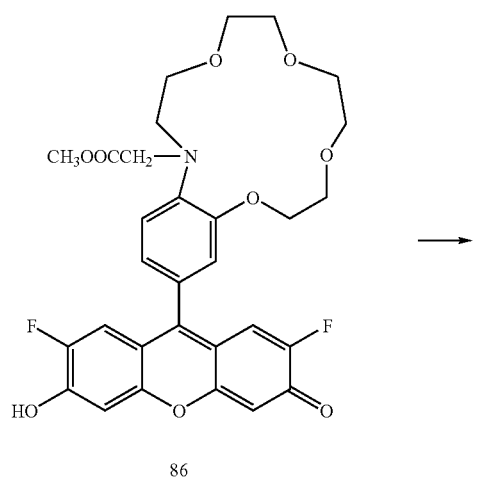

86

-continued

140

Example 119

Synthesis of Compound 141

A 0.1M solution of compound 140 in DMSO is added to a 0.1M solution of an equivalent mass of aminodextran (average MW 10000) in 0.3M sodium bicarbonate solution. The resulting solution is stirred at rt overnight, then slowly diluted with 10× methanol. The resulting precipitate is collected by centrifugation to give conjugated substance 141, which can be purified further if necessary by gel filtration chromatography using water and Sephadex G-15.

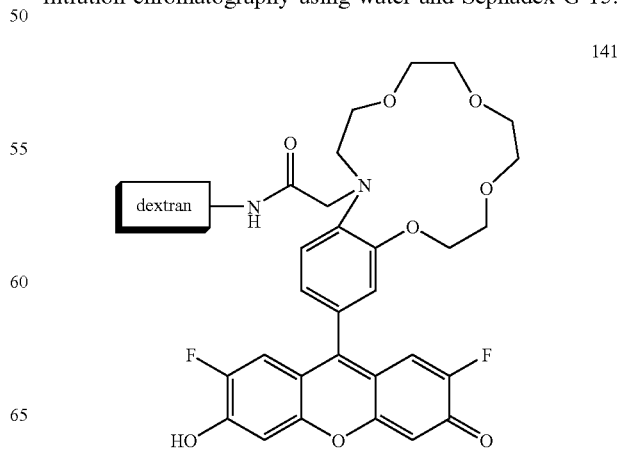

141

All publications, patents and patent applications referred to within this document are incorporated by reference to the same extent as if each individual publication, patent or patent application was specifically and individually indicated to be incorporated by reference.

The reagents employed in the examples are commercially available or can be prepared using commercially available instrumentation, methods, or reagents known in the art. The foregoing examples illustrate various aspects of the invention and practice of the methods of the invention. The examples are not intended to provide an exhaustive description of the many different embodiments of the invention. Thus, although the forgoing invention has been described in some detail by way of illustration and example for purposes of clarity of understanding, those of ordinary skill in the art will realize readily that many changes and modifications can be made thereto without departing from the spirit or scope of the appended claims.

What is claimed is:

1. A crown ether chelating compound having formula:

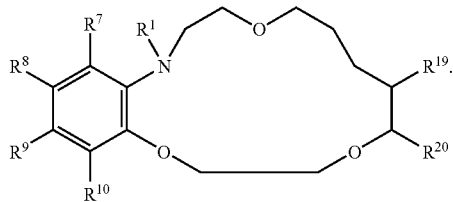

wherein

R$^1$ is selected from the group consisting of -L-R$_X$, -L-S$_C$, -L-DYE, C$_1$–C$_{18}$ alkyl and C$_7$–C$_{18}$ arylalkyl, each of which is optionally substituted by halogen, azido, nitro, nitroso, amino, hydroxy, cyano, C$_1$–C$_6$ alkoxy, an aryl or heteroaryl ring system, —(SO$_2$)—R$^{15}$, —(SO$_2$)—O—R$^{15}$, —(C=O)—R$^{15}$, —(C=O)—O—R$^{16}$, —(C=O)—NR$^{17}$R$^{18}$, C$_1$–C$_6$ alkylamino, C$_2$–C$_{12}$ dialkylamino, C$_1$–C$_6$ alkyl or C$_1$–C$_6$ alkoxy, each of which is itself optionally substituted by halogen, amino (—NR$^{17}$R$^{18}$), hydroxy, —(SO$_2$)—R$^{15}$, —(SO$_2$)—O—R$^{15}$, —(C=O)—R$^{15}$, —(C=O)—O—R$^{16}$ or —(C=O)—NR$^{17}$R$^{18}$;

R$^{15}$ is selected from the group consisting of H, C$_1$–C$_6$ alky, -L-R$_X$, -L-S$_c$ and -L-DYE;

R$^{16}$ is selected from the group consisting of H, C$_1$–C$_8$ alkyl, benzyl, a biologically compatible esterifying group, a biologically compatible salt, -L-R$_X$, -L-S$_C$, and -L-DYE;

R$^{17}$ and R$^{18}$ are independently selected from the group consisting of H, C$_1$–C$_8$ alkyl, C$_1$–C$_6$ carboxyalkyl, alpha-acyloxyalkyl, trialkylsilyl, a biologically compatible salt, -L-R$_X$, -L-S$_C$, and -L-DYE; or R$^{17}$ and R$^{18}$ taken in combination from a 5- or 6-membered aliphatic ring that optionally incorporates an oxygen atom;

each L is independently a covalent linkage;

each DYE is independently a reported molecule;

each Rx is independently an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a halotriazine, a hydrazine, an imido ester, an isocyanate, an isothiocyanate, a maleimide, a phosphoramidite, a reactive platinum complex, a silyl halide, a sulfonyl halide, a thiol and a photo-activatable group;

each Sc is independently an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell or a virus;

R$^{19}$ and R$^{20}$ are independently selected from the group consisting of H, halogen, azido, nitro, nitroso, amino, cyano, -L-R$_X$, -L-S$_C$, -L-DYE, C$_1$–C$_6$ alkyl and C$_1$–C$_6$ alkoxy, each of which is itself optionally substituted by halogen, amino, hydroxy, —(SO$_2$)—R$^{15}$, —(SO$_2$)—O—R$^{15}$, —(C=O)—R$^{15}$, —(C=O)—O—R$^{16}$, or —(C=O)—NR$^{17}$R$^{18}$;

or R$^{19}$ and R$^{20}$ taken in combination form a fused six-membered benzo moiety that is optionally substituted by halogen, azido, nitro, nitroso, amino, cyano, -L-R$_X$, -L-S$_C$, -L-DYE, C$_1$–C$_6$ alkyl or C$_1$–C$_6$ alkoxy, each of which is itself optionally substituted by halogen, amino, hydroxy, —(SO$_2$)—R$^{15}$, —(SO$_2$)—O—R$^{15}$, —(C=O)—R$^{15}$, —(C=O)—O—R$^{16}$, or —(C=O)—NR$^{17}$R$^{18}$;

R$^7$, R$^8$, R$^9$ and R$^{10}$ are independently selected from the group consisting of H, halogen, azido, nitro, nitroso, amino, cyano, -L-R$_X$, -L-S$_C$, -L-DYE, C$_1$–C$_6$ alkyl or C$_1$–C$_6$ alkoxy, each of which is itself optionally substituted by halogen, amino, hydroxy, —(SO$_2$)—R$^{15}$, —(SO$_2$)—O—R$^{15}$, —(C=O)—R$^{15}$, —(C=O)—O—R$^{16}$, or —(C=O)—NR$^{17}$R$^{18}$;

or any two adjacent substituents R$^7$–R$^{10}$, taken in combination, form a fused six-membered benzo moiety, which is optionally substituted by halogen, azido, nitro, nitroso, amino, cyano, -L-R$_X$, -L-S$_C$, -L-DYE, c$_1$–C$_6$ alkyl or C$_1$–C$_6$ alkoxy, each of which is optionally substituted by halogen, amino, hydroxy, —(C=O)—R$^{15}$, —(C=O)—O—R$^{16}$, or —(C=O)—NR$^{17}$R$^{18}$;

or any two adjacent substituents R$^7$–R$^{10}$, or R$^{19}$ and R$^{20}$, taken in combination with each other, form a fused DYE.

2. The compound according to claim 1, wherein at least one of said R$^1$, R$^7$, R$^8$, R$^9$, R$^{10}$, R$^{19}$ or R$^{20}$ is -L-Rx, -L-Sc or -L-DYE or R$^8$ in combination with R$^9$ form a fused DYE.

3. The compound according to claim 1, wherein said L is a single covalent bond, or a covalent linkage that is linear or branched, cyclic or heterocyclic, saturated or unsaturated, having 1–20 nonhydrogen atoms selected from the group consisting of C, N, P, O and S; and are composed of any combination of ether, thioether, amine, ester, carboxamide, sulfonamide, hydrazide bonds and aromatic or heteroaromatic bonds.

4. The compound according to claim 1, wherein said—Rx is selected from the group consisting of carboxylic acid, succinimidyl ester of a carboxylic acid, hydrazide, amine and a maleimide.

5. The compound according to claim 1, wherein said—Sc is selected from the group consisting of an antibody or fragment thereof, an avidin or streptavidin, a biotin, a blood component protein, a dextran, an enzyme, an enzyme inhibitor, a hormone, an IgG binding protein, a fluorescent protein, a growth factor, a lectin, a lipopolysaccharide, a microorganism, a metal binding protein, a metal chelating moiety, a non-biological microparticle, a peptide toxin, a phosphotidylserine-binding protein, a structural protein, a small-molecule drug, or a tyramide.

6. The compound according to claim 1, wherein said—DYE is selected from the group consisting of xanthene, borapolyazaindacene, carbocyanine, benzofuran, quinazolinone, indole, a benzazole, oxazine, and coumarin.

7. The compound according to claim 6, wherein said—DYE moiety is independently substituted by a lipophilic group.

8. The compound according to claim 7, wherein said lipophilic group is an AM or acetate ester.

9. The compound according to claim 1, wherein said compound is selected from the group consisting of Formula (II)(a),

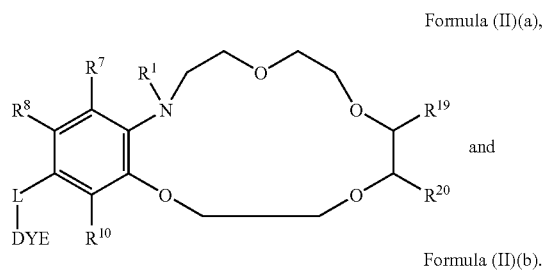

and

Formula (II)(b).

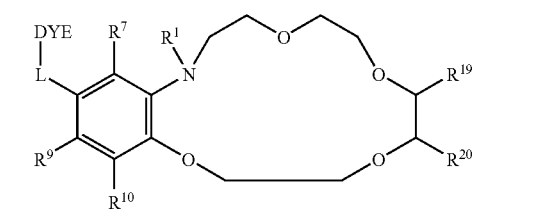

10. The compound according to claim 9, wherein said DYE is selected from the group consisting of borapolyazaindacene, xanthene and indole.

11. The compound according to claim 9, wherein said DYE moiety is independently substituted by a lipophilic group.

12. The compound according to claim 11, wherein said lipophilic group is an AM or acetate ester.

13. The compound according to claim 9, wherein $R^7$, $R^8$, $R^9$, $R^{10}$, $R^{19}$ and $R^{20}$, when present, are H.

14. The compound according to claim 13, wherein $R^1$ is $C_1$–$C_6$ alkyl that is substituted one or more times by amino (—$NR^{17}R^{18}$), —(C=O)—O—$R^{16}$ or —(C=O)—$NR^{17}R^{18}$.

15. The compound according to claim 14, wherein said $R^1$ is methyl or ethyl.

16. The compound according to claim 15 wherein said $R^{16}$ is selected from the group consisting of H, $C_1$–$C_6$ alkyl, benzyl, a biologically compatible esterifying group, and a biologically compatible salt.

17. The compound according to claim 16 wherein said $R^{16}$ is methyl.

18. The compound according to claim 14 wherein said $R^{17}$ and $R^{18}$ are each methyl.

19. A compound having formula:

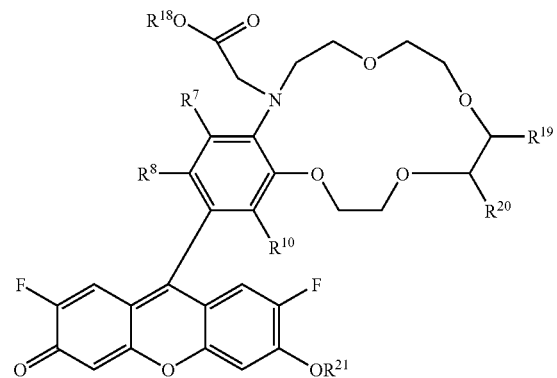

wherein $R^{16}$ is selected from the group consisting of H, $C_1$–$C_6$ alkyl, benzyl, a biologically compatible esterifying group, and a biologically compatible salt;

$R^{19}$ and $R^{20}$ are selected from the group consisting of H, halogen, azido, nitro, nitroso, amino, cyano, -L-$R_X$, -L-$S_C$, -L-DYE, $C_1$–$C_6$ alkyl and $C_1$–$C_6$ alkoxy, each of which is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$ and —(C=O)—$NR^{17}R^{18}$;

or $R^{19}$ and $R^{20}$ taken in combination form a fused six-membered benzo moiety that is optionally substituted by halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$;

$R^{15}$ is selected from the group consisting of H, $C_1$–$C_6$ alkyl, -L-$R_X$, -L-$S_C$ and -L-DYE;

$R^{16}$ is selected from the group consisting of H, $C_1$–$C_6$ alkyl, benzyl, a biologically compatible esterifying group, a biologically compatible salt, -L-$R_X$, -L-$S_C$ and -L-DYE;

$R^{17}$ and $R^{18}$ are independently selected from the group consisting of H, $C_1$–$C_6$ alkyl, $C_1$–$C_6$ carboxyalkyl, alpha-acyloxyalkyl, trialkylsilyl, a biologically compatible salt, -L-$R_X$, -L-$S_C$ and -L-DYE; or $R^{17}$ and $R^{18}$ taken in combination form a 5- or 6-membered aliphatic ring that optionally incorporates an oxygen atom;

each L is independently a covalent linkage;

each $R_X$ is independently an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a halotriazine, a hydrazine, an imido ester, an isocyanate, an isothiocyanate, a maleimide, a phosphoramidite, a reactive platinum complex, a silyl halide, a sulfonyl halide, a thiol and a photoactivatable group;

each $S_C$ is independently an amino acid, a peptide, a protein, a polysaccharide, a nucleoside, a nucleotide, an oligonucleotide, a nucleic acid, a hapten, apsoralen, a drug, a hormone, a lipid, a lipid assembly, a synthetic polymer, a polymeric microparticle, a biological cell or a virus;

each DYE is independently a reporter molecule;

$R^7$, $R^8$, and $R^{10}$ are independently selected from the group consisting of H, halogen, azido, nitro, nitroso, amino, cyano, -L-$R_X$, -L-$S_C$, -L-DYE, $C_1$–$C_6$ alkyl and $C_1$–$C_6$ alkoxy, each of which is optionally substituted by halogen, amino, hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$;

or $R^7$ taken in combination with $R^8$ form a fused six-membered benzo moiety, which is optionally substituted by halogen, azido, nitro, nitroso, amino, cyano, -L-$R_X$, -L-$S_C$, -L-DYE, $C_1$–$C_6$ alkyl or $C_1$–$C_6$ alkoxy, each of which is optionally substituted by halogen, amino, hydroxy, —(C=O)—$R^{15}$, —(C=O)—O—$R^{16}$, or —(C=O)—$NR^{17}R^{18}$; and, $R^{21}$ is selected from the group consisting of H, $C_1$–$C_{18}$ alkyl, $C_7$–$C_{18}$ arylalkyl and a lipophilic group each alkyl is optionally substituted by —(C=O)—$R^{15}$, —(C=O)—O—$R^{16}$, or $C_1$–$C_6$ alkoxy.

20. The compound according to claim 19, wherein said $R^7$, $R^8$, and $R^{10}$ are H.

21. The compound according to claim 20, wherein said $R^{19}$ and $R^{20}$ are H.

22. The compound according to claim 21, wherein said $R^{16}$ is methyl or a biologically compatible esterifying group.

23. The compound according to claim 19 wherein said $R^{16}$, $R^{19}$ or $R^{20}$ is —L-Sc.

24. A composition comprising:

a) a compound having the formula

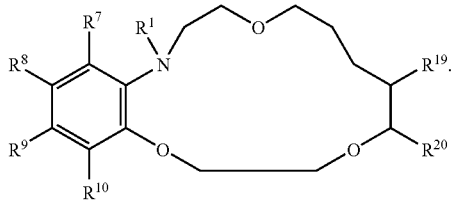

wherein $R^1$ is selected from the group consisting of -L-$R_X$, -L-$S_C$, -L-DYE, $C_1$–$C_{18}$ alkyl and $C_7$–$C_{18}$ arylalkyl, each of which is optionally substituted by halogen, azido, nitro, nitroso, amino, hydroxy, cyano, $C_1$–$C_6$ alkoxy, an aryl or heteroaryl ring system, —($SO_2$)—$R^{15}$, —($SO_2$)—O—$R^{15}$, —(C=O)—$R^{15}$, —(C=O)—O—$R^{16}$, —(C=O)—$NR^{17}R^{18}$, $C_1$–$C_6$ alkylamino, $C_2$–$C_{12}$ dialkylamino, $C_1$–$C_6$ alkyl or $C_1$–$C_6$ alkoxy, each of which is itself optionally substituted by halogen, amino (—$NR^{17}R^{18}$), hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$;

$R^{15}$ is selected from the group consisting of H, $C_1$–$C_6$ alkyl, -L-$R_X$, -L-$S_C$, -L-DYE;

$R^{16}$ is selected from the group consisting of H, $C_1$–$C_6$ alkyl, benzyl, a biologically compatible esterifying group, a biologically compatible salt, -L-$R_X$, -L-$S_C$, -L-DYE;

$R^{17}$ and $R^{18}$ are independently selected from the group consisting of H, $C_1$–$C_6$ alkyl, $C_1$–$C_6$ carboxyalkyl, alpha-acyloxyalkyl, trialkylsilyl, a biologically compatible salt, -L-$R_X$, -L-$S_C$ and -L-DYE; or $R^{17}$ and $R^{18}$ taken in combination form a 5- or 6-membered aliphatic ring that optionally incorporates an oxygen atom;

each L is independently a covalent linkage;

each DYE is independently a reporter molecule;

each Rx is independently an acrylamide, an activated ester of a carboxylic acid, a carboxylic ester, an acyl azide, an acyl nitrile, an aldehyde, and alkyl halide, an anhydride, an aniline, an amine, an aryl halide, an azide, an aziridine, a boronate, a diazoalkane, a haloacetamide, a halotriazine, a hydrazine, an imido ester, an isocyanate, an isothiocyanate, a maleimide, a phosphoramidite, a reactive platinum complex, a silyl halide, a sulfonyl halide, athiol and a photoactivatable group;

each Sc independently an amino acid, a peptide, a protein, a polysaccharide, a nucleoside, a nucleotide, an oligonucleotide, a nucleic acid, a hapten, a psoralen, a drug, a hormone, a lipid assembly, a synthetic polymer, a polymeric microparticle, a biological cell or a virus;

$R^{19}$ and $R^{20}$ are independently selected from the group consisting of H, halogen, azido nitro, nitroso, amino, cyano, -L-$R_X$, -L-$S_C$, -L-DYE, $C_1$–$C_6$ alkoxy, each of which is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$;

or $R^{19}$ and $R^{20}$ taken in combination form a fused six-membered benzo moiety that is optionally substituted by halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$;

$R^7$, $R^8$, $R^9$ and $R^{10}$ are independently selected from the group consisting of H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy; —($SO_2$)—$R^{15}$, —($SO_2$)—O—$R^{15}$, —(C=O)—$R^{15}$, —(C=O)—O—$R^{16}$, or —(C=O)—$NR^{17}R^{18}$;

or any two adjacent substituents $R^7$–$R^{10}$, taken in combination, form a fused six-membered benzo moiety, which is optionally substituted by halogen, azido, nitro, nitroso, amino, cyano, -L-$R_X$, -L-$S_C$, -L-DYE, $C_1$–$C_6$ alkyl or $C_1$–$C_6$ alkoxy, each of which is optionally substituted by halogen, amino, hydroxy, —(C=O)—$R^{15}$, —(C=O)—O—$R^{16}$, or —(C=O)—$NR^{17}R^{18}$;

or any two adjacent substituents $R^7$–$R^{10}$, or $R^{19}$ and $R^{20}$, taken in combination with each other, form a fused DYE; and, b) a metal ion that is capable of being chelated by said compound.

25. The composition according to claim 24, wherein said metal ion is selected from the group consisting of $Na^+$, $Li^+$, $K^+$, $Ca^+$, $Zn^+$ and $Rb^+$.

26. A method for binding a target metal ion in a sample, comprising steps of:

a) contacting said sample with a metal chelating compound having the formula

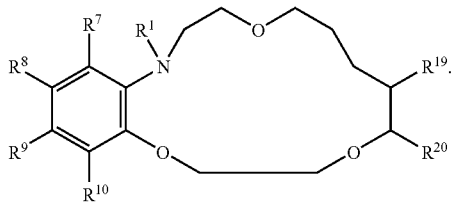

wherein $R^1$ is selected from the group consisting of -L-$R_X$, -L-$S_C$, -L-DYE, $C_1$–$C_{18}$ alkyl and $C_7$–$C_{18}$ arylalkyl, each of which is optionally substituted by halogen, azido, nitro, nitroso, amino, hydroxy, cyano, $C_1$–$C_6$ alkoxy, an aryl or heteroaryl ring system, —($SO_2$)—$R^{15}$, —($SO_2$)—O—$R^{15}$, —(C=O)—$R^{15}$, —(C=O)—O—$R^{16}$, —(C=O)—$NR^{17}R^{18}$, $C_1$–$C_6$ alkylamino, $C_2$–$C_{12}$ dialkylamino, $C_1$–$C_6$ alkyl or $C_1$–$C_6$ alkoxy, each of which is itself optionally substituted by halogen, amino (—$NR^{17}R^{18}$), hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$;

$R^{15}$ is selected from the group consisting of H, $C_1$–$C_6$ alkyl, -L-$R_X$, -L-$S_C$, -L-DYE;

$R^{16}$ is selected from the group consisting of H, $C_1$–$C_6$ alkyl, benzyl, a biologically compatible esterifying group, a biologically compatible salt, -L-$R_X$, -L-$S_C$, -L-DYE;

$R^{17}$ and $R^{18}$ are independently selected from the group consisting of H, $C_1$–$C_6$ alkyl, $C_1$–$C_6$ carboxyalkyl, alpha-acyloxyalkyl, trialkylsilyl, a biologically compatible salt, -L-$R_X$, -L-$S_C$ and -L-DYE; or $R^{17}$ and $R^{18}$ taken in combination form a 5- or 6-membered aliphatic ring that optionally incorporates an oxygen atom;

each L is independently a covalent linkage;

each DYE is independently a reporter molecule;

each Rx is independently an acrylamide, an activated ester of a carboxylie acid, a carboxylic ester, an acyl azide, an acyl nitrile, an aldehyde, and alkyl halide, an anhydride, an aniline, an amine, an aryl halide, an azide, an aziridine, a boronate, a diazoalkane, a haloacetamide, a halotriazine, a hydrazine, an imido ester, an isocyanate, an isothiocyanate, a maleimide, a phosphoramidite, a reactive platinum complex, a silyl halide, a sulfonyl halide, athiol and a photoactivatable group;

each Sc is independently an amino acid, a peptide, a protein, a polysaccharide, a nucleoside, a nucleotide, an loiqonucleotide, a nucleic acid, a hapten, a psoralen, a drug, a hormone, a lipid, a lipid assembly, a synthetic polymer, a polymeric microparticle, a biological cell or a virus;

$R^{19}$ and $R^{20}$ are independently selected from the group consisting of H, halogen, azido, nitro, nitroso, amino, cyano, -L-$R_X$, -L-$S_C$, -L-DYE, $C_1$–$C_6$ alkoxy, each of which is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$;

or $R^{19}$ and $R^{20}$ taken in combination form a fused six-membered benzo moiety that is optionally substituted by halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$;

$R^7 R^8$, $R^9$ and $R^{10}$ are independently selected from the group consisting of H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy; —($SO_2$)—$R^{15}$, —($SO_2$)—O—$R^{15}$, —(C=O)—$R^{15}$, —(C=O)—O—$R^{16}$, or —(C=O)—$NR^{17}R^{18}$;

or any two adjacent substituents $R^7$–$R^{10}$, taken in combination, form a fused six-membered benzo moiety, which is optionally substituted by halogen, azido, nitro, nitroso, amino, cyano, -L-$R_X$, -L-$S_C$, -L-DYE, $C_1$–$C_6$ alkyl or $C_1$–$C_6$ alkoxy, each of which is optionally substituted by halogen, amino, hydroxy, —(C=O)—$R^{15}$, —(C=O)—O—$R^{16}$, or —(C=O)—$NR^{17}R^{18}$;

or any two adjacent substituents $R^7$–$R^{10}$, or $R^{19}$ and $R^{20}$, taken in combination with each other, form a fused DYE; and, b) incubating said sample and said metal chelating compound for sufficient time to allow said compound to chelate said target metal ion whereby said metal ion is bound.

27. The method according to claim 26, wherein said method further comprises illuminating said metal chelating compound with a suitable light source whereby said target ion is detected with the proviso that at least one of $R^1$, $R^4$, $R^7$, $R^8$, $R^9$, $R^{10}$, $R^{19}$ or $R^{20}$ is —L-DYE or at least two of $R^7$–$R^{10}$ or $R^{19}$ and $R^{20}$, taken in combination, form a fused DYE.

28. The method according to claim 27, wherein said target metal ion is selected from the group consisting of $Na^+$, $Li^+$, $K^+$, $Ca^+$, $Zn^+$ and $Rb^+$.

29. The method according to claim 28, wherein said target metal ion is $Na^+$.

30. The method according to claim 28, wherein said sample comprises living cells, cellular components, proteins, peptides, buffer solutions or biological fluids.

31. A method for binding and detecting target ions in a live cell, said method comprises:

a) contacting a sample of live cells with a crown ether compound with the proviso that said compound comprise a DYE moiety and at least one lipohilic group, wherein the crown ether compounds has the formula

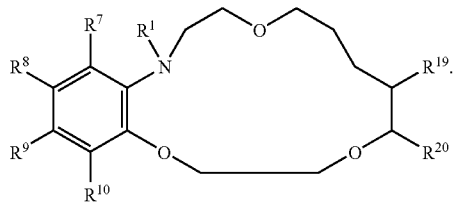

wherein $R^1$ is selected from the group consisting of -L-$R_X$, -L-$S_C$, -L-DYE, $C_1$–$C_{18}$ alkyl and $C_7$–$C_{18}$ arylalkyl, each of which is optionally substituted by halogen, azido, nitro, nitroso, amino, hydroxy, cyano, $C_1$–$C_6$ alkoxy, an aryl or heteroaryl ring system, —($SO_2$)—$R^{15}$, —($SO_2$)—O—$R^{15}$, —(C=O)—$R^{15}$, —(C=O)—O—$R^{16}$, —(C=O)—$NR^{17}R^{18}$, $C_1$–$C_6$ alkylamino, $C_2$–$C_{12}$ dialkylamino, $C_1$–$C_6$ alkyl or $C_1$–$C_6$ alkoxy, each of which is itself optionally substituted by halogen, amino (—$NR^{17}R^{18}$), hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$;

$R^{15}$ is selected from the group consisting of H, $C_1$–$C_6$ alkyl, -L-$R_X$, -L-$S_C$, -L-DYE;

$R^{16}$ is selected from the group consisting of H, $C_1$–$C_6$ alkyl, benzyl, a biologically compatible esterifying group, a biologically compatible salt, -L-$R_X$, -L-$S_C$, -L-DYE;

$R^{17}$ and $R^{18}$ are independently selected from the group consisting of H, $C_1$–$C_6$ alkyl, $C_1$–$C_6$ carboxyalkyl, alpha-acyloxyalkyl, trialkylsilyl, a biologically compatible salt, -L-$R_X$, -L-$S_C$ and -L-DYE; or $R^{17}$ and $R^{18}$ taken in combination form a 5- or 6-membered aliphatic ring that optionally incorporates an oxygen atom;

each L is independently a covalent linkage;

each DYE is independently a reporter molecule;

each Rx is independently an acrylamide, an activated ester of a carboxylic acid, a carboxylic ester, an acyl azide, an acyl nitrile, an aldehyde, and alkyl halide, an anhydride, an aniline, an amine, an aryl halide, an azide, an aziridine, a boronate, a diazoalkane, a haloacetamide, a halotriazine, a hydrazine, an imido ester, an isocyanate, an isothiocyanate, a maleimide, a phosphoramidite, a reactive platinum complex, a silyl halide, a sulfonyl halide, athiol and a photoactivatable group;

each Sc is independently an amino acid, a peptide, a protein, a polysaccharide, a nucleoside, a nucleotide, an oliqonucleotide, a nucleic acid, a hapten, a psoralen, a drug, a hormone, a lipid, a lipid assembly, a synthetic polymer, a polymeric microparticle, a biological cell or a virus;

$R^{19}$ and $R^{20}$ are independently selected from the group consisting of H, halogen, azido, nitro, nitroso, amino, cyano, -L-$R_X$, -L-$S_C$, -L-DYE, $C_1$–$C_6$ alkyl and $C_1$–$C_6$ alkoxy, each of which is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$;

or $R^{19}$ and $R^{20}$ taken in combination form a fused six-membered benzo moiety that is optionally substituted by halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy, —($SO_2$)—$R^{15}$, —($SO_2$)—O—$R^{15}$, —(C=O)—$R^{15}$, —(C=O)—O—$R^{16}$, or —(C=O)—$NR^{17}R^{18}$;

$R^7$, $R^8$, $R^9$ and $R^{10}$ are independently selected from the group consisting of H, halogen, azido, nitro, nitroso, amino, cyano, -L-$R_X$, -L-$S_C$, -L-DYE, $C_1$–$C_6$ alkyl or $C_1$–$C_6$ alkoxy, each of which is itself optionally substituted by halogen, amino, hydroxy; —($SO_2$)—$R^{15}$, —($SO_2$)—O—$R^{15}$, —(C=O)—$R^{15}$, —(C=O)—O—$R^{16}$, or —(C=O)—$NR^{17}R^{18}$;

or any two adjacent substituents $R^7$–$R^{10}$, taken in combination, form a fused six-membered benzo moiety, which is optionally substituted by halogen, azido, nitro, nitroso, amino, cyano, -L-$R_X$, -L-$S_C$, $C_1$–$C_6$ alkyl or $C_1$–$C_6$ alkoxy, each of which is optionally substituted by halogen, amino, hydroxy, —(C=O)—$R^{15}$, —(C=O)—O—$R^{16}$, or —(C=O)—$NR^{17}R^{18}$;

or any two adjacent substituents $R^7$–$R^{10}$, or $R^{19}$ and $R^{20}$, taken in combination with each other, form a fused DYE;

b) incubating said sample and said crown ether chelate compound for sufficient time to allow said compound to chelate said target metal ion; and, c) illuminate said sample with an appropriate wavelength whereby said target ion is detected in a live cell.

32. The method according to claim 31, wherein said DYE moiety is substituted by a lipophilic group.

33. The method according to claim 32 wherein said lipophilic group is an AM or acetate ester.

* * * * *